United States Patent [19]

Buist et al.

[11] Patent Number: 5,955,258
[45] Date of Patent: Sep. 21, 1999

[54] PROCESS FOR THE LYSIS OF A CULTURE OF LACTIC ACID BACTERIA BY MEANS OF A LYSIN, AND USES OF THE RESULTING LYSED CULTURE

[75] Inventors: Girbe Buist, Groningen; Gerard Venema, Haren; Jan Kok, Groningen; Adrianus Marinus Ledeboer, ML Rotterdam, all of Netherlands

[73] Assignee: Quest International B.V., Naarden, Netherlands

[21] Appl. No.: 08/737,716

[22] PCT Filed: May 12, 1995

[86] PCT No.: PCT/NL95/00170

§ 371 Date: Apr. 22, 1997

§ 102(e) Date: Apr. 22, 1997

[87] PCT Pub. No.: WO95/31561

PCT Pub. Date: Nov. 23, 1995

[30] Foreign Application Priority Data

May 12, 1994 [EP] European Pat. Off. ............. 94201353

[51] Int. Cl.$^6$ ............... C12Q 1/00; C12N 1/00; A01N 63/00; C07H 21/04
[52] U.S. Cl. ................... 435/4; 435/6; 435/69.1; 435/91.1; 435/71.2; 435/252.1; 435/320.1; 424/93.21; 424/94.61; 536/23.2; 536/23.7; 536/24.1

[58] Field of Search ............... 435/6, 69.1, 91.1, 435/228, 320.1, 325, 4, 71.2, 252.1; 536/23.7, 24.1, 23.2; 424/93.21, 94.61

[56] References Cited

U.S. PATENT DOCUMENTS 5,326,858  7/1994  Lichenstein et al. ............. 536/23.2

*Primary Examiner*—James Ketter
*Assistant Examiner*—William Sandals
*Attorney, Agent, or Firm*—Pillsbury Madison & Sutro LLP

[57] ABSTRACT

The invention provides a process for the lysis of a culture of lactic acid bacteria, or a product containing such culture e.g. cheese, by means of a lysin through the in situ production of a homologous autolysin, or a heterologous autolysin obtainable from Gram-positive bacteria esp. from lactic acid bacteria. The gene encoding said autolysin is controlled by a promoter, preferably regulated by food-grade ingredients or parameters, to achieve an enhanced lysis after induction resulting in an enhanced production of total autolysin compared with the natural production lever of the homologous autolysin during fermentation or shortly thereafter. Other uses of the invention include preparing a mixture of peptides which are modified by peptidases freed after the lysis, using the autolysin as a bactericidal agent against spoiling bacteria or pathogenic bacteria for improving the shelf life of a product containing the lysed culture.

27 Claims, 23 Drawing Sheets

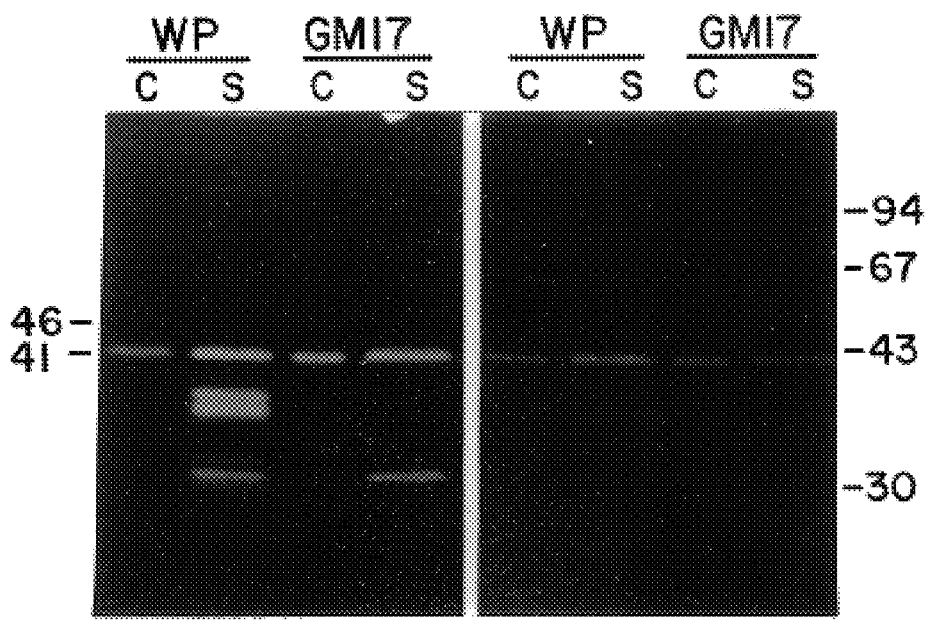
FIG. IA    FIG. IB
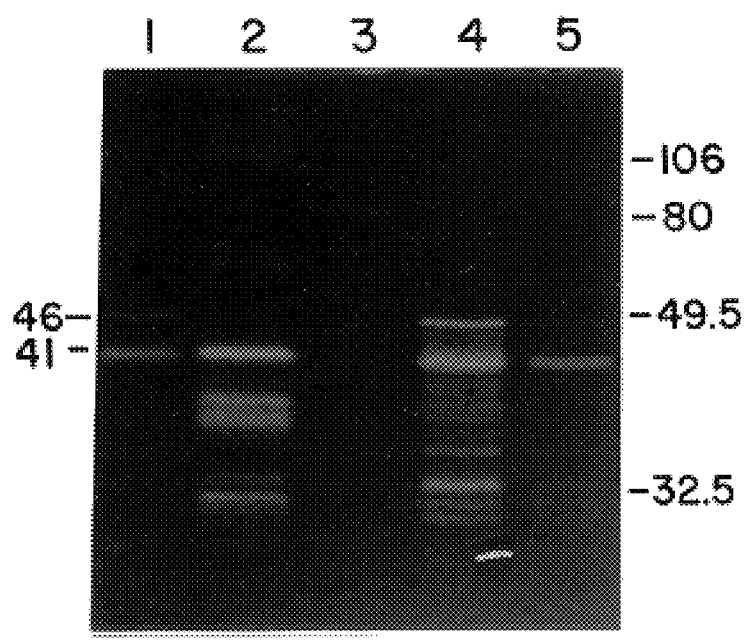
FIG. 2

FIG. 4

```
                    SspI
    1          5'-ATTTTTGTTTTAAATCAGATTTTTTAGATTAAAGGCAAAAAGTTTTTACAAATATGAATCCTTAACGGAAAAACGTTTACA
                        -35               -10        ScaI                          rbs
   82   AACCGCCACCAAATTGACATCTTTTTTTAGCTTGAGGCGTGGTAGAATAAAGATAGTACTTATTATATTTTGTAATCTTTAGaaaggTAATTATTT acmA -->
  178   ATGCCAGTATCACGTGTTAAAGTTAAAAATAGACATTTAAAAAAGAAAACTAAAAAACCACTCGCTTTTTATAAACCAGCCACAAAATTTGCTGGC
    1    M  P  V  S  R  V  K  V  K  N  R  H  L  K  K  K  T  K  K  P  L  A  F  Y  K  P  A  T  K  F  A  G PALA-4 ->
  274   GCTGTTCTTATTGCCGGAACATTGACAACCACACATGAACTTCTTCTTCAACAGACAAGTCCAATGGTTCAAGCAGCGACTAACTCATCAGAGGTT
   33    A  V  L  I  A  G  T  L  T  T  T  H  E  L  L  Q  Q  T  S  P  M  V  Q  A  A  T  N  S  S  E  V 370   TTTATTGAAAGTATTGCCGCATCAGCAAAACCTGTGGCAGATGCTAATGGCTTATATCCTTCGGTCATGATTGCCCAAGCTATTTTGGAAAGCAAC
   65    F  I  E  S  I  A  A  S  A  K  P  V  A  D  A  N  G  L  Y  P  S  V  M  I  A  Q  A  I  L  E  S  N SacI
  466   TGGGGCTCAAGTCAGCTTTCACGAGCTCCCTATTATAATTTATTTGGTATTCAAGGTACTTATCAAGGAAAGAGCGTCGTATTTAAAACTCAAGAG
   97    W  G  S  S  Q  L  S  R  A  P  Y  Y  N  L  F  G  I  Q  G  T  Y  Q  G  K  S  V  V  F  K  T  Q  E 562   TATCTCAATGGTAAATGGGTGACTAAAGATATGCCCTTTAGGGTCTATCCTTCCTTTAATCAAAGTTTTCAAGACAATGCTTATGTTCTAAAAACA
  129    Y  L  N  G  K  W  V  T  K  D  M  P  F  R  V  Y  P  S  F  N  Q  S  F  Q  D  N  A  Y  V  L  K  T 658   ACAAACTTTGGGAATGGTCCCTATTACGCTAAGGCTTGGCGGGCCAATGCTGCCACCTATCAAGACGCTACTGCTGCTTTGACGGGCAGATATGCT
  161    T  N  F  G  N  G  P  Y  Y  A  K  A  W  R  A  N  A  A  T  Y  Q  D  A  T  A  A  L  T  G  R  Y  A 754   ACCGACCCAAGTTATGGCGCTTCACTGAATCGCATTATTTCTCAATATAATTTGACTCGTTTTGACGGAGCTTCTTCAGCTGGAAATACTAATTCT
  193    T  D  P  S  Y  G  A  S  L  N  R  I  I  S  Q  Y  N  L  T  R  F  D  G  A  S  S  A  G  N  T  N  S 850   GGTGGCTCGACAACCACAATTACGAATAATAATTCTGGAACCAATAGCAGTTCAACTACTTATACCGTCAAATCTGGTGATACTCTTTGGGGAATC
  225    G  G  S  T  T  T  I  T  N  N  N  S  G  T  N  S  S  S  T  T  Y  T  V  K  S  G  D  T  L  W  G  I 946   TCACAAAGATATGGAATTAGTGTCGCTCAAATTCAAAGTGCGAATAATCTTAAAAGTACCATTATCTACATTGGTCAAAAACTTGTACTGACAGGT
  257    S  Q  R  Y  G  I  S  V  A  Q  I  Q  S  A  N  N  L  K  S  T  I  I  Y  I  G  Q  K  L  V  L  T  G 1042   TCAGCTTCTTCTACAAATTCAGGTGGTTCAAACAATTCCGCAAGCACTACTCCAACCACTTCTGTGACACCTGCAAAACCAACTTCACAAACAACT
  289    S  A  S  S  T  N  S  G  G  S  N  N  S  A  S  T  T  P  T  T  S  V  T  P  A  K  P  T  S  Q  T  T SpeI
 1138   GTTAAGGTTAAATCCGGAGATACCCTTTGGGCGCTATCAGTAAAATATAAAACTAGTATTGCTCAATTGAAAAGTTGGAATCATTTAAGTTCAGAT
  321    V  K  V  K  S  G  D  T  L  W  A  L  S  V  K  Y  K  T  S  I  A  Q  L  K  S  W  N  H  L  S  S  D 1234   ACCATTTATATTGGTCAAAATCTTATTGTTTCACAATCTGCTGCTGCTTCAAATCCTTCGACAGGTTCAGGCTCAACTGCTACCAATAACTCAAAC
  353    T  I  Y  I  G  Q  N  L  I  V  S  Q  S  A  A  A  S  N  P  S  T  G  S  G  S  T  A  T  N  N  S  N 1330   TCGACTTCTTCTAACTCAAATGCCTCAATTCATAAGGTCGTTAAAGGAGATACTCTCTGGGGACTTTCGCAAAAATCTGGCAGCCCAATTGCTTCA
  385    S  T  S  S  N  S  N  A  S  I  H  K  V  V  K  G  D  T  L  W  G  L  S  Q  K  S  G  S  P  I  A  S <- PALA-14                                       3'-TAATAATAATTACTTGAAAATCAATTATTT
 1426   ATCAAGGCTTGGAATCATTTATCTAGCGATACTATTTTAATTGGTCAGTATCTACGAATAAAATAAATTATTATTAATGAACTTTTAGTTAATAAA
  417    I  K  A  W  N  H  L  S  S  D  T  I  L  I  G  Q  Y  L  R  I  K ----------->    <----------------
 1522   TTTTCTTACTTTAAGTTAAGTAAGAAAAAAATTAAGAACATTTTGGCGAACTTCTACCTATCTTGCCCAGCCAAGACTGTAAGGTTGTCAGTAAAG
   94   AAAAGAATGAAATTCAAT-3' E  K  K  L  E  Q  L  V  A  Q  L  H  I  S  R  T  P  E  S  M  G  V  T  M  E 1618   GGTTCCTCAACAAAGAAAAAGTTCTCGGTTAAGTTCTTTTTGTGCAACTTTACTTCAATTAAGAAGTGTCAAGCAATTTATCAGTTAGAGAAAAAA
   69    W  P  T  T  E  K  E  L  A  L  E  L  F  V  R  Q  F  S  T  L  E  E  C  N  T  L  Y  D  I  E  K  K 1714   TCTCTCGTTTTAAAACAGTGCAACTTAGTGAAACAAATCCATCGCTTGGGTTTCAAGATTTAAGGTAAACCTAAAAACCCGTCGGACGTTCTCTAT
   37    S  L  L  I  K  Q  R  Q  I  V  K  N  L  Y  R  V  W  L  E  L  N  W  K  S  K  Q  A  A  Q  L  L  Y <-- ORFA            rbs                                 HindIII                HindIII
 1810   AAGTTAGGTGCAGTAACATTATtggagTCATAAAAACCTAAAAAAGCATTTATTAAAAAAATTTCGAAGAAGTGTATTCGGTTTGATATTCGAAG
    5    E  I  W  T  M         Q  L  L  R  L  I  K  P  N  K  R  L  Y  N  K  L  A  E  E  G  Y  A  L  S  Y  A  E
   35

Sau3A
 1905   ATTTTATTGGCGACCCAGACGGCTAG-5'      1930
    8    L  I  V  A  P  D  A  S <-- ORFB    1
```

FIG. 5A

```
L.lactis     MPVSRVKVKNRHLKKKTKKPLAFYKPATKfagavllagtltttHELL----------------------------------------   47
S.faecalis   MKKESMSRIERRKAQQRKKTPVQWKKSitlfssalivssvgtpvallpvtaEATEEQPTNAEVAQAPTTETGLVETPTTETTPGI   85
E.hirae      M--ENIARKERRRLNETKRFRKV-KRSaalvgtamwgcsvaapli-----------QPVQVDADQTPT----------------   54
             *  ...  .*.  ...*.     *       ...     .....                       ▲

L.lactis     --------------------------LQQTSPMVQAATNSS-----------------------------------------   62
S.faecalis   TEQPTTDSSTTTESTTESSKETPTTPSTEQPTVDSTTPVESGTTDSSVAEITPVAPSTTESEAAPAVTPDDEVKVPEARVASAQT  170
E.hirae      -------------------------------------------------------------------------------------   54

L.lactis     ----------EVFIESIAASAKPVADANGLYPSVMIAQAILESNWGSSQLSRAPYYNLFGIQGTYQGKSVVFKTQEYLNGKWVTK  137
S.faecalis   FSALSPTQSPSEFIAELARCAQPIAQANDLYASVMMAQAIVESGWGASTLSKAPNYNLFGIKGSYNGQSVYMDTWEYLNGKWLVK  255
E.hirae      --QFGARINTAAFIAEIATYAQPIAQANDLYASVMIAQAVVESGWGSSALSQAPYYNLFGIKGSYQGQTVYMDTLEYLNNKWVSK  137
                .**...*  *.*.** .**.** ***.***..**.**.*  **.**  ****** .*.*  * ****.**.  *

L.lactis     DMPFRVYPSFNQSFQDNAYVLKTTNFGNGPYY-AKAWRANAATYQDATAALTGRYATDPSYGASLNRIISQYNLTRFDGASSAGN  221
S.faecalis   KEPFRKYPSYMESFQDNAHVLKTTSFQAGVYYYAGAWKSNTSSYRDATAWLTGRYATDPSYNAKLNNVITAYNLTQYDTPSSGGN  340
E.hirae      KEPFRQYPSFAESFNDNAYVLRNTSFGNG-YYYAGTWKSNTKSYTDATACLTGRYATDPGYAGKLNNIITTYGLTKYDTPASGNA  221
              .*** ***. **.***.**..*.** *  ** *  *.*.*   * .****  ****** ..***** .*  .*.*  *...

L.lactis     T---------NSGGSTTTITNNNSGTNSSSTTYTVKSGDTLWGISQRYGISVAQIQSANNLKSTIIYIGQKLVLTG--SASS    292
S.faecalis   TGGGTV-NPGTGGSNNQSG-----------TNTYYTVKSGDTLNKIAAQYGVSVANLRSWNGISGDLIFVGQKLIVKKGAS---   409
E.hirae      GGGVTIGNGGNTGNTSNSGSTSGNSGGSATTTGTTYTVKSGDSVWGISHSFGITMAQLIEWNNIKNNFIYPGQKLTIKGGQSAGS  306
                .                 ...*.       ..* *******..  *.   *.**...   * ......*. ****... *

L.lactis     TNSGGSNNSASTTPTTSVTPAKPTSQTTVK---VKSGDTLWALSVKYKTSIAQLKSWNHLSSDTIYIGQNLIVSQSAAASNPSTG  374
S.faecalis   -----GNTGGSGNGGSNNNQSG-----TNTYYTVKSGDTLNKIAAQYGVTVANLRSWNGISGDLIFVGQKLIVKKGTSGNTGGSS  484
E.hirae      STTNTGNNASSGNTSGNTNTSGSTGQATGAKYTVKSGDSVWKIANDHGISMNQLIEWNNIKNNFVYPGQQLVVSKGSSSASGSTS  391
               .*...*.                   *      *****..  *. .   * **  ..   * **. .  .** .*.

L.lactis     SGSTATNNSNS--TSSNSNASIHKVVKGDTLWGLSQKSGSPIASIKAWNHLSSDTILIGQYLRIK                      437
S.faecalis   NGGSNNNQSGTN--------TYYTIKSGDTLNKIAAQYGVSVANLRSWNGISGDLIFAGQKIIVKKGTSGNTGGSSNGGSNNNQS  561
E.hirae      NTSTGNTSSNTANTGSTTSGSTYTVKAGESVWSVSNKFGISMNQLIQWNNIKNNFIYPGQKLIVKGGSSSSNASTSTANNKNTAS  476
              ...... *.       .... *...  ...*  ...  ** ....  * **  .* **....+.+.....+.....+..+

S.faecalis   GTNTY-------YTIKSGDTLNKISAQFGVSVANLRSWNGIKGDLIFAGQTIIVKKGAS--------------AGGNASSTNSAS  625
E.hirae      SNTSSTATGQATYTVKAGESVWGVANKNGISMNQLIEWNNIKNNFIYPGQKLIVKGGSSKASATATIKPTASTPASTTPTASSTG  561
             ....         ++.+.+.++.....     +..... .+.....+.. ++ ++..

S.faecalis   GKRHTVKSGDSLWGLSMQYGISIQKIKQLNGLSGDTIYIGQTLKVG                                          671
E.hirae      DTKYTVKAGESVWGVANKHHITMDQLIEWNNIKNNFIYPGQEVIVKKGTAQSTPAKSDEKTYTVKAGESVWGVADSHGITMNQLI  646
                 ..+++.+.+.++..   ... +.......+......  ++ ++..

E.hirae      EWNNIKNNFIYPGQQLIVKK   666
```

FIG. 5B

```
L.lactis    ————————————————————□—□—□
S.faecalis  ——//——————————————□—□—□—□—□
E.hirae     ————————————————□—□—□—□—□—□
```

FIG.6

```
222  ----TNSGGS------TTTITNNNSGTNSSS TTYTVKSGDTLWGISQRYGISVAQTQSANNLKSTIIYIGQKLVLT
288  GSASSTNSGGSNNSASTTPTTSVTPAKPTSQ TTVKVKSGDTLWALSVKYKTSIAQLKSWMHLSSDTFYIGQNIIVS
364  QSAAASNPSTGSGSTATNNSNSTSSN--SNA SIHKVVKGDTLWGISQKSGSPIASTKAWMHLSSDTLIGQYIRIK
                                       * ***  **  **    * *        *    *   *
                                       .   .   .   .   .   .   .   .   .
```

FIG. 8
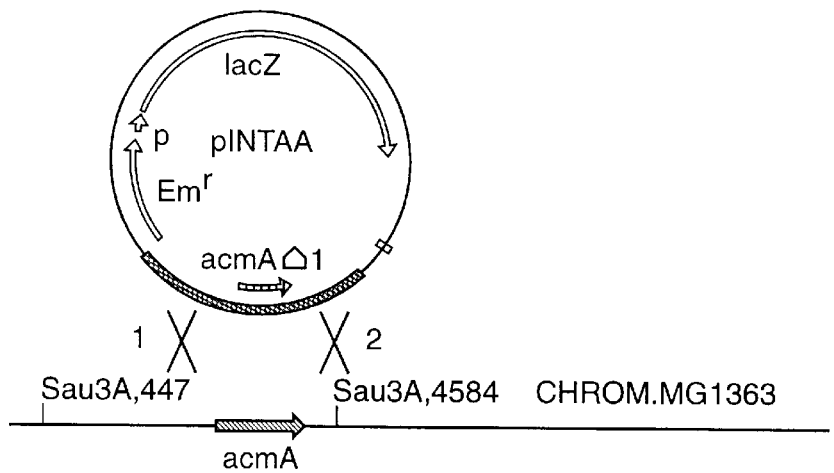
FIRST CROSSOVER:
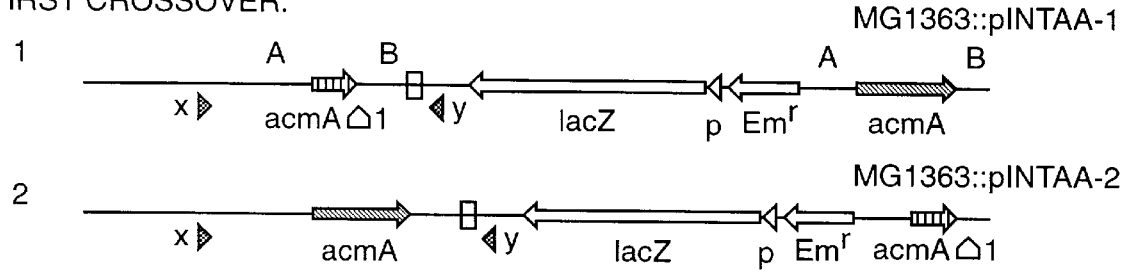
SECOND CROSSOVER IN 1
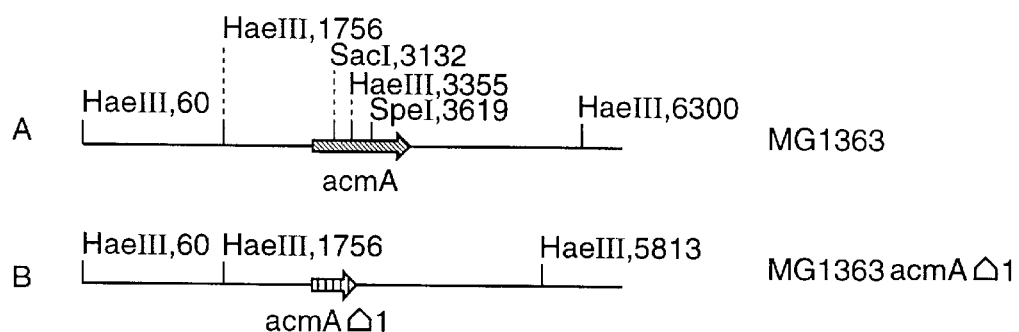

MG1363

MG1363acmAΔ1

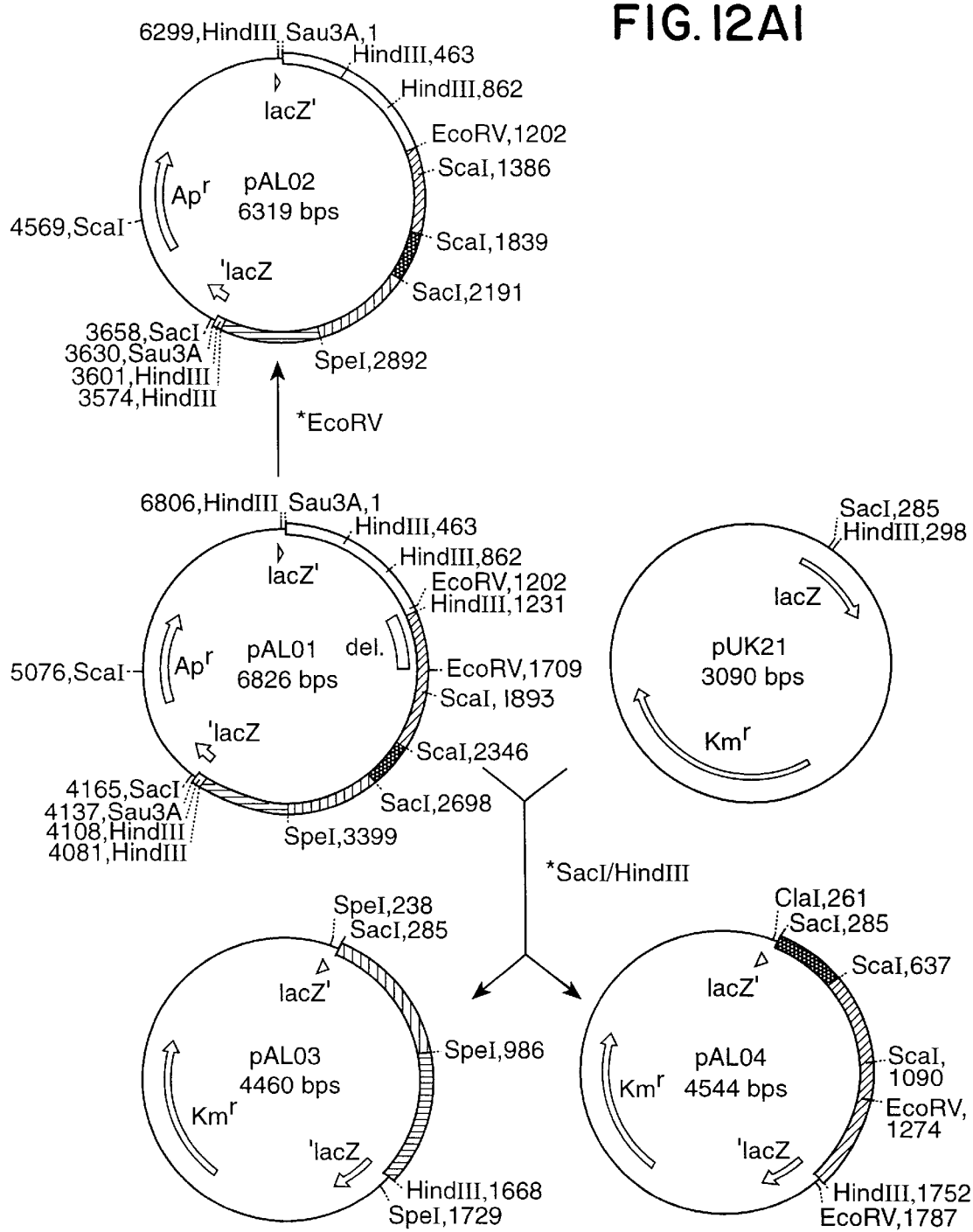
FIG. 12A1

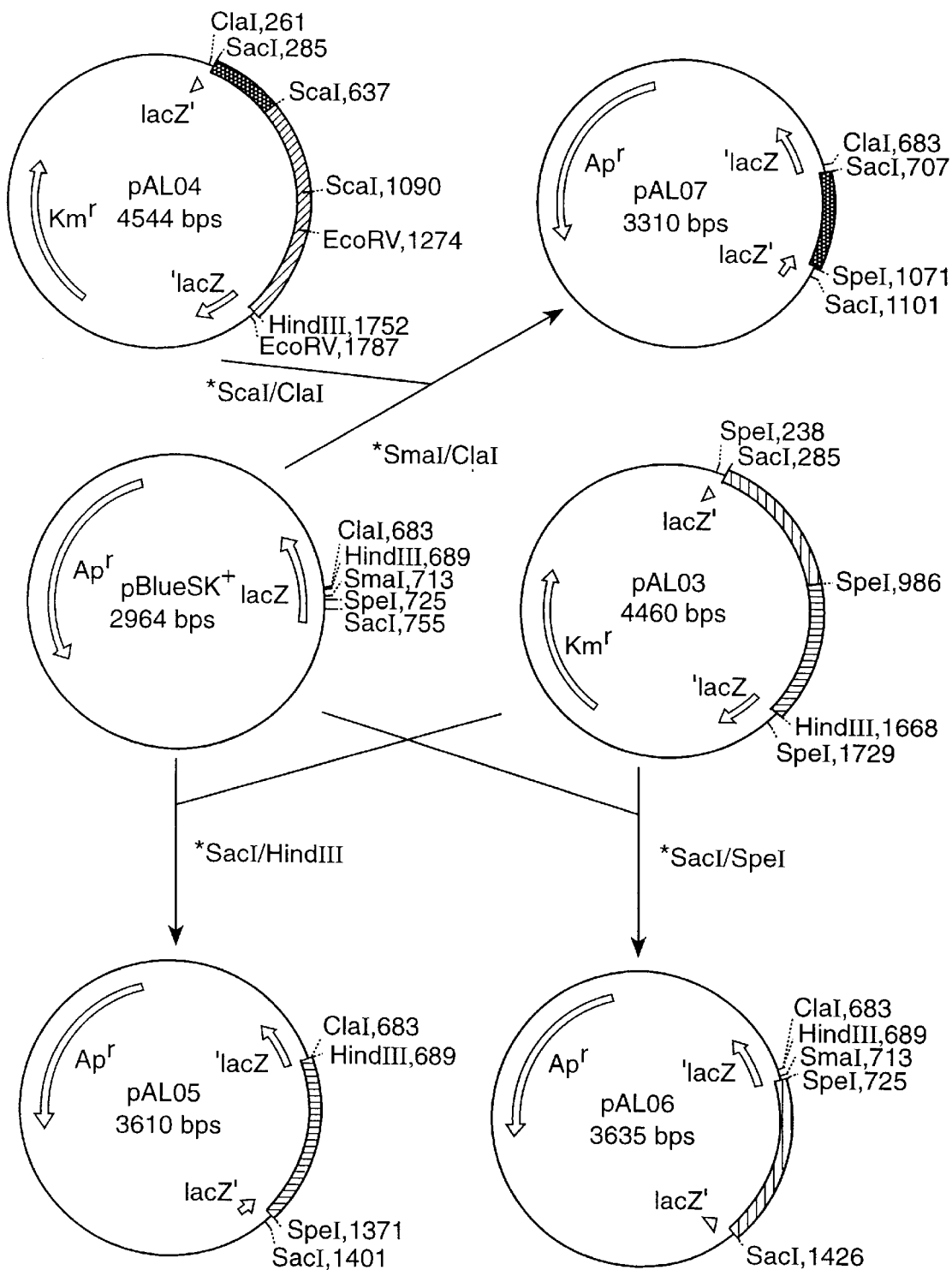
FIG.12A2

```
    SspI
5'-AATATTTTTGTTTTAAATCAGATTTTTTAGATTAAAGGCAAAAAGTTTTTACAAATATGA

-35
ATCCTTAACGGAAAAACGTTTACAAACCGCCACCAAATTGACATCTTTTTTTAGCTTGAGGCG

-10        ScaI                              rbs         acmA→
TGGTAGAATAAAGATAGTACTTATTATATTTTGTAATCTTTAGaaaggTAATTATTTATG-3
```

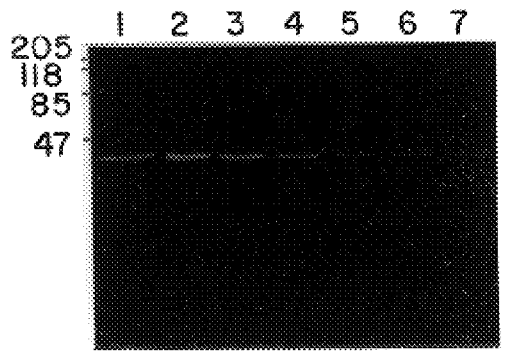
FIG. 18A1
MG1363
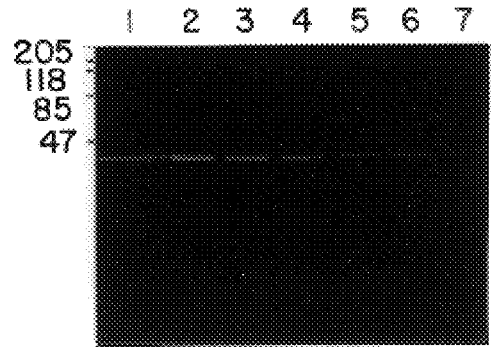
FIG. 18A2
MG1363pepT
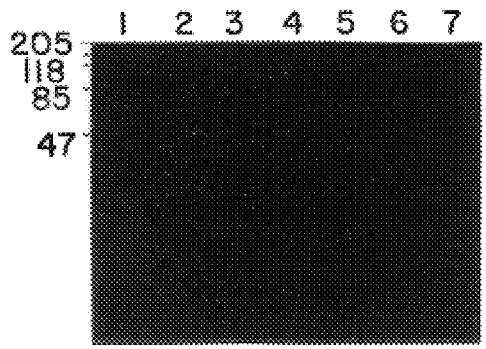
FIG. 18A3
MG1363acmAΔ1
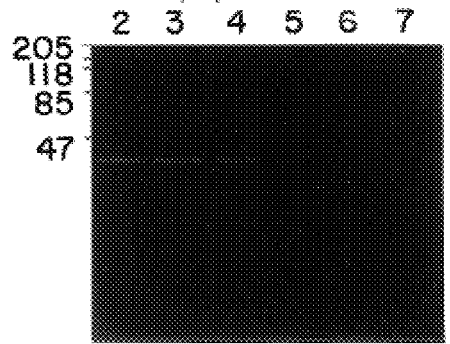
FIG. 18A4
MG1363pepT/MG1363acmAΔ1

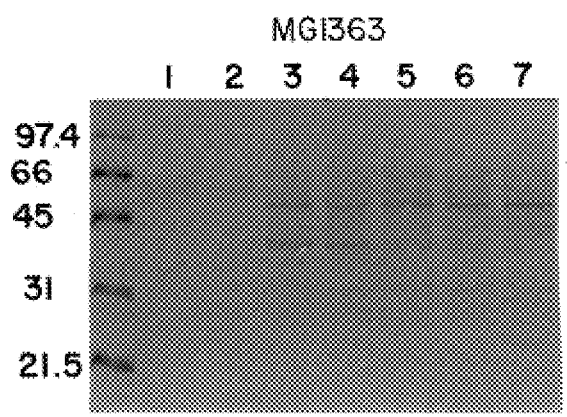
FIG. 18B1
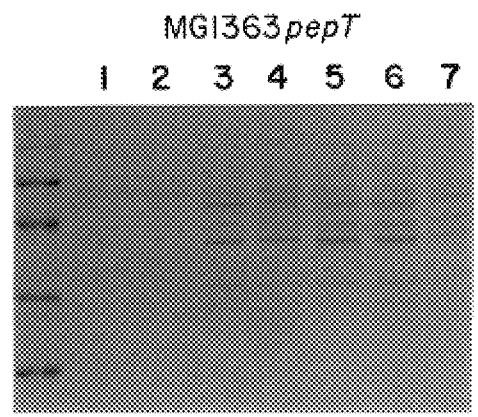
FIG. 18B2
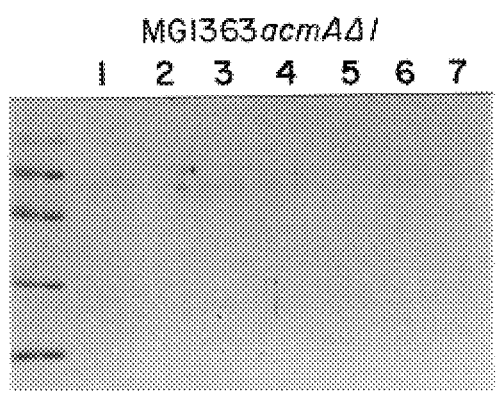
FIG. 18B3
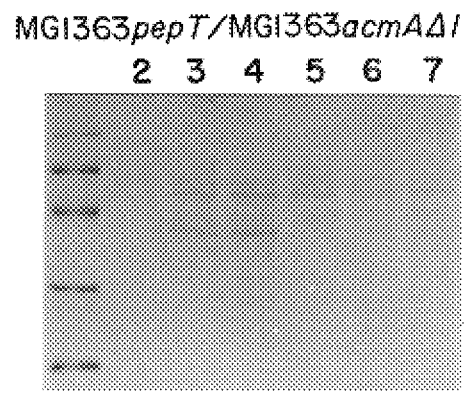
FIG. 18B4

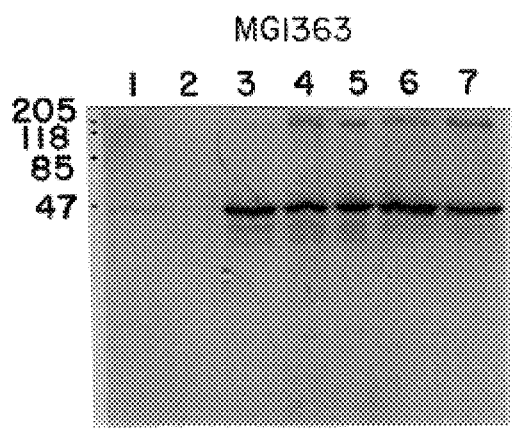
FIG. 18C1
MG1363
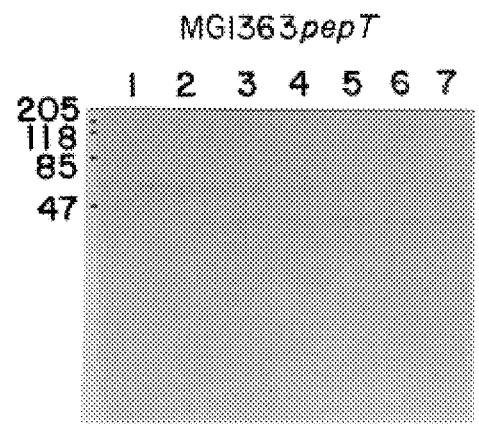
FIG. 18C2
MG1363pepT
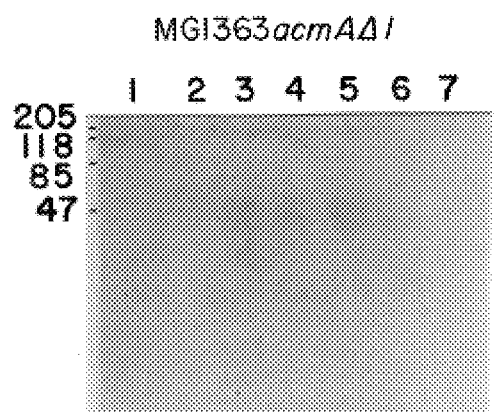
FIG. 18C3
MG1363acmAΔ1
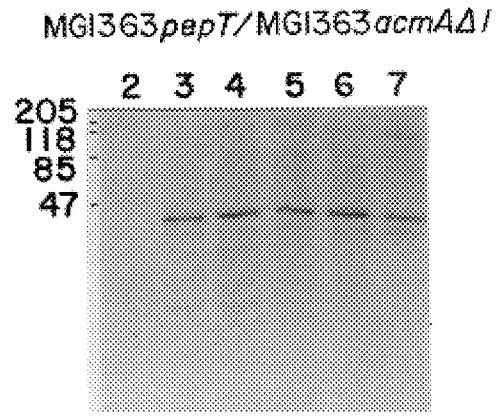
FIG. 18C4
MG1363pepT/MG1363acmAΔ1

PROCESS FOR THE LYSIS OF A CULTURE OF LACTIC ACID BACTERIA BY MEANS OF A LYSIN, AND USES OF THE RESULTING LYSED CULTURE

This application is the national phase of international application PCT/NL95/00170, filed May 12, 1995 which designated the U.S.A.

BACKGROUND OF THE INVENTION AND PRIOR ART

The invention relates to a process for the lysis of a culture of lactic acid bacteria, or a product containing such culture, by means of a lysin e.g. in producing a fermented food product, e.g. in cheese-making. Such a process is known from WO 90/00599 (AGRICULTURAL & FOOD RESEARCH COUNCIL (AFRC), M. J. Gasson, published Jan. 25, 1990, ref. 1). According to that patent specification the lysin from a Lactococcus (preferably prolate-headed) bacteriophage was used to lyse bacterial starter cultures during cheese-making. Exemplified was the lysin of the bacteriophage φvML3 of *Lactococcus lactis* ML3. In particular, the lysin can be added to a cheese product or a cheese precursor mixture, e.g. after whey removal, milling and salting. However, this solution has the disadvantage that thorough mixing of the contents of the lysed cells with the cheese product is not easily obtained. Another disadvantage is that the lysin was produced by *Escherichia coli* cells, which are not food-grade. It is explicitly stated if the cell wall of the host cell is not itself degraded by the lysin then the lysin secreting transformed host may be useful in suppressing populations of bacteria which are susceptible to lysis by the lysin. Nothing is mentioned regarding addition of a transformed host cell in improving cheese flavor, certainly not a transformed lactic acid bacterium.

As an alternative it is suggested in that patent specification "to encapsulate the lysin so that the timing of its addition is not important. The encapsulating agent dissolves after the cheese-making process is complete thus not affecting the starter bacteria before their role in acidification was complete."

This suggested alternative has the disadvantages, that (a) an encapsulating material has to be used, and (b) said material must not dissolve before the end of the cheese making process. Moreover, if the encapsulated lysin is added at the beginning of the cheese-making process, e.g. while adding the cheese starter culture to the milk, about 90% of it is removed with the whey. Thus one has to add about tenfold the required effective amount, which is economically not attractive. In a later publication C. A. Shearman, K. Jury & M. J. Gasson (Feb. 1992, ref. 2) described an autolytic *Lactococcus lactis* expressing a cloned lactococcal bacteriophaze φvML3 lysin gene. In particular they stated that "(e)xpression of the cloned lysin did not impair the ability of *Lactococcus lactis* subsp. *lactis* and *Lactococcus lactis* subsp. *cremoris* strains to metabolize lactose, to clot milk and produce acid (data not shown)".

It was suggested that during the exponential phase the lysin would not, or would insufficiently be expressed. It would only be expressed in sufficient amounts to lyse an appreciable proportion of the cells during the stationary phase, which occurs at the end of the normal fermentation process. The article illustrates that maintenance of transformed lactococcal strains could be a problem. Maintenance at a temperature below 30° C. slightly delayed the onset of lysis but at 30° C. regrowth of lysin resistant bacteria occurred. As alternative buffering in a sucrose medium with a sucrose percentage higher than 20% was given. This does not seem to be suitable in a process of fermentation like cheese making where the fermentation step occurs at 30° C. or higher and the presence of more than 20% sucrose is not acceptable.

Furthermore, at the end of that publication it was indicated that expression in the stationary phase is not completely controlled. In addition the use of osmotic buffer in a cheese maturing process is probably not very efficient timewise. This can be illustrated by the length of time required for a Gouda cheese immersed in a brine bath to achieve the desired degree of salt flavour. For this cheese type for example the osmotic effect of salt concentration is not going to be very quick. The cheddar cheese making process would probably be more suitable as the salt addition step is more efficient, however, this still has the disadvantage of requiring a mixing step.

Both disclosures described the use of a lysin originating from a lactococcal bacteriophage lysin, that means an enzyme produced in nature by an undesired substance like a bacteriophage, because bacteriophage contaminations are a major problem in large scale industrial dairy fermentation processes.

In a review article R. Young (1992, ref. 4) gives a survey of the state of the art on bacteriophage lysis, both mechanism and regulation. Especially in the section "Lysis in Phage Infections of Gram-Positive Hosts" on pages 468–472 it was indicated that the DNA sequence found by Shearman c.s. (1989, ref. 5), which DNA sequence seems to be the same as that given in ref. 1, is probably not correct and that the deduced amino acid sequence might be quite different due to a mutation causing a phase shift in the reading frame.

In a publication of Ward c.s. (1993; ref. 6) it is also suggested that the sequence of Shearman et al. (1989; ref. 5) is probably not correct. Comparison with a very similar phage lysin gene confirmed that a frame shift in the Shearman et al. (ref. 5) sequence is needed for aligning the two DNA sequences. Moreover, this comparison teaches that the real phage lysin is encoded by an ORF that is probably 45 bases longer than disclosed by Shearman et al. (ref. 5).

C. Platteeuw and W. M. de Vos (1992, ref. 3) described the location, characterization and expression in *Escherichia coli* of lytic enzyme-encoding gene, lytA, of *Lactococcus lactis* bacteriophage φUS3. It was described that the φvML3 lysin, which is active on a wide range of lactococcal strains, lacked homology with known lytic enzymes. The bacteriophage φUS3 was identified during studying bacteriophages specific for the cheese-making strain *Lactococcus lactis* SK11 (NIZO). The results showed that the deduced amino acid sequence of LytA shares similarities with that of an autolysin of *Streptococcus pneumonia*, suggesting that the bacteriophage φUS3 encodes an amidase rather than a lysozyme-type muramidase. The above illustrates the difficulties facing a person skilled in the art wishing to isolate DNA-sequences from different organisms. The lack of information regarding sequences and the lack of homology between known sequences makes use of probes and primers derived from known sequences quite unlikely to lead to successful isolation of a correct DNA sequence from different organisms.

In EP-A2-0 510 907 (AFRC, M. J. Gasson, published Oct. 28, 1992, ref. 7) the use of bacteriophages of food-contaminating or pathogenic bacteria or the lysins thereof to kill such bacteria was described. Examples included lysins from bacteriophages of *Listeria monocytogenes* (phage φLM4) and *Clostridium tyrobutyricum* (phage φP). Also tests for bacterial contamination can be made specific for specific bacteria by using the appropriate bacteriophage or lysin thereof and determining whether cells are lysed thereby. That European patent application thus describes the use of lysins obtained from phages of food-contaminating or even pathogenic bacteria, which is not desirable for food-grade applications. Moreover, the purpose of use of such lysins in that patent application is further away from the subject of this invention, which will be discussed below as it does not lie in improving flavour of food products by autolysis of lactic acid bacteria.

SUMMARY OF THE INVENTION

In contrast to these prior art developments the present invention relates to the use of a "real autolysin", i.e. a lysin obtainable from grampositive foodgrade bacteria preferably lactic acid bacteria, (i.e. not an autolysin derived or derivable from a bacteriophage) for improving food products and the processes for preparing food products. The maturation of cheese is a process of particlar relevance. In particular, the present invention is based on the identification and isolation of the gene of *Lactococcus lactis* subsp. *lactis* encoding a lysin that is capable of lysing the cell in which it is produced. During the normal fermentation process the amount of lysin should not be so large that it causes lysis of the cells in which it is produced. However, a limited constitutive production of the autolysin is needed to guarantee separation of cells and to prevent the formation of too strong cell walls.

When a natural lactic acid culture is grown without addition of (sufficient) nutritional ingredients, after the exponential phase growth will decrease due to lack of nutritional ingredients and the culture will enter the stationary phase. Then after several days starvation will occur, and this event probably causes an increase in natural autolysin. Consequently during starvation enhanced amounts of the natural autolysin will be formed and will lyse the cells of the lactic acid bacteria. In the subject case the inventors faced the problem of devising a manner of lysing the foodgrade bacterium as soon as possible after the foodgrade bacterium enters the stationary phase and with a minimum of steps, without interfering with the normal activity of the foodgrade bacterium in the fermentation process in which it is involved. This has been achieved through recombinant DNA technology on a foodgrade bacterium which leaves the foodgrade status and functionality of the bacterium intact and achieves regulatable lysis of the foodgrade bacterium in situ at any desired time.

In this specification the following abbreviations of names of micro-organisms are used:
E.=Escherichia, e.g. *E. coli,*
L.=Lactococcus, e.g. *L. lactis,*
M.=Micrococcus, e.g. *M. lysodeikticus,*
S.=Streptococcus, e.g. *S. faecalis* and *S. pneumonia.*

BRIEF DESCRIPTION OF THE DRAWINGS

FIG. 1. Cell wall hydrolase activity of *L. lactis* MG1363 in renaturing (12.5%) SDS-PAGE. (A) gel containing 0.2% (wt/vol) *M. lysodeikticus* autoclaved cells (B) gel containing 0.2% (wt/vol) cell walls from *L. lactis* MG1363. WP, fractions of cultures grown in whey-based medium and GM17, respectively; C, cell-free extract; S, supernatant fraction. The amount of sample loaded was equalized according to the optical density of the cultures. Molecular masses of standard proteins are shown on the right, and the sizes of two of the lytic bands discussed in the text are indicated on the left (all in kilodaltons (kDa)).

FIG. 2. Cell wall hydrolase activity in *E. coli* NM522 transformants by renaturing (12.5%) SDS-PAGE. The gel contained 0.2% (wt/vol) *M. lysodeikticus* autoclaved cells. 1,2: cell-free extract and supernatant of *L. lactis* MG1363 grown in whey-based medium, respectively; 3, cell-free extract of *E. coli* NM522; 4 and 5, cell-free extracts of two independent *E. coli* NM522 transformants producing a halo on TY plates containing *M. lysodeikticus* autoclaved cells. Molecular masses of standard proteins (in kDa) are shown on the right. Two lytic bands corresponding to sizes of 41 and 46 kDa are indicated on the left.

FIG. 4. Nucleotide sequence (SEQ ID NOS:1 and 11) and deduced amino acid sequences of acmA (SEQ ID NO:2), ORFA (SEQ ID NO:10) and part of ORFB (SEQ ID NO:12) of *L. lactis* MG1363. Putative ribosome binding sites (rbs and lower case), −10 and −35 sequences (shaded), startcodons (bold face), and stop codons (underlined) are indicated. A possible transcriptional terminator is indicated by horizontal arrows above the sequence. The synthetic primers PALA-4 and PALA-14 used in the PCR experiment are overlined. The possible signal peptide cleavage site is indicated by ↑. A number of relevant restriction enzyme sites are also indicated. The intergenic region between acmA and ORFA is shown double stranded.

FIG. 5. (A.) Alignment of the deduced amino acid sequences of AcmA (SEQ ID NO:2) of *L. lactis* the autolysin (SEQ ID NO:13) of *S. faecalis* (ref. 2), and muramidase-2 (SEQ ID NO:14) of *Enterococcus hirae* (ref. 6) both of which are not foodgrade. The internally repeated regions of the three proteins are underlined. Identical (*) amino acids in all three proteins, identical (+) amino acids between muramidase-2 and the autolysin of *S. faecalis* in the C-terminal of the two enzymes not present in AcmA, and similar (.) amino acids are indicated. (▲), signal peptide cleavage site in muramidase-2; (shaded and lower case), putative membrane spanning domains. (B.) Schematic presentation of the alignment shown in (A). Thick line, (putative) signal sequence. The two slashes indicate the sequence in the *S. faecalis* autolysin not present in AcmA and muramidase-2. Repeated sequences according to the consensus proposed by Joris et al. (20) are boxed.

FIG. 6. Amino acid sequence alignment of the carboxy terminal repeats of AcmA (in the box) plus the preceding and intervening sequences (SEQ ID NO:4). The consensus sequence proposed by Joris et al. (20) is shaded. (*),identical amino acids; (.), similar amino acids.

FIG. 8. Schematic representation of the construction of the chromosomal acmAΔ1 mutant of *L. lactis* using pIN-TAA. Black bar, insert of pAL09 in pORI280; acmAΔ1, deletion derivative of acmA; $Em^r$, erythromycin resistance gene; lacZ, β-galactosidase gene of *E. coli* expressed under the control of the lactococcal promoter $P_{32}(p)$; open square, origin of replication of the lactococcal plasmid pWV01; 1 and 2, possible sites for the first crossover; x and y, primers PALA-19 and BK05AL, respectively, used to distinguish between the two types of Campbell integrants; A and B, possible regions for a second crossover and their products A and B. A number of relevant restriction enzyme sites are also shown.

FIGS. 12A1/12A2. Scheme showing the construction of deletion derivatives of pAL01. Ap$^r$, ampicillin resistance gene; Km$^r$, kanamycin resistance gene; lacZ, α-lacZ; del., EcoRV deletion resulting in pAL02. Some restriction enzyme sites are given. The various subfragments of the 2850-bp HindIII fragment in pAL01 obtained in separate subclones are indicated by various modes of shading.

FIG. 12.B. Scheme showing the construction of the integration plasmid pINTAA. Ap$^r$, ampicillin resistance gene; Black bar, insert of pAL09 in pORI280; acmAΔ1(vertical lined), deletion derivative of acmA(dotted); Em$^r$, erythromycin resistance gene; lacZ, β-galactosidase gene of *E. coli* expressed under the control of the lactococcal promoter $P_{32}(P)$; ori+, origin of replication of the lactococcal plasmid pWV01. A number of relevant restriction enzyme sites are shown.

FIGS. 18A1, 18A2, 18A3, and 18A4. A Detection of AcmA activity in a renaturing SDS-12.5% PAGE containing 0.15% (wt/vol) *M. lysodeikticus* autoclaved cells. FIGS. 18B1, 18B2, 18B3, and 18B4. Analysis of released intracellular proteins on a 12.5% PAA gel stained with Coomassie. FIGS. C1, C2, C3 and C4. Detection of PepT among the released intracellular proteins by using specific antibodies. Only the results of the samples of the supernatant fractions are shown. Numbers 1 to 7, shown on top of the gels, are the time points, indicated in FIG. 17, at which the samples were taken. Molecular masses (in kilodaltons) of standard proteins are shown on the left.

TABLE 3

Figure 3:
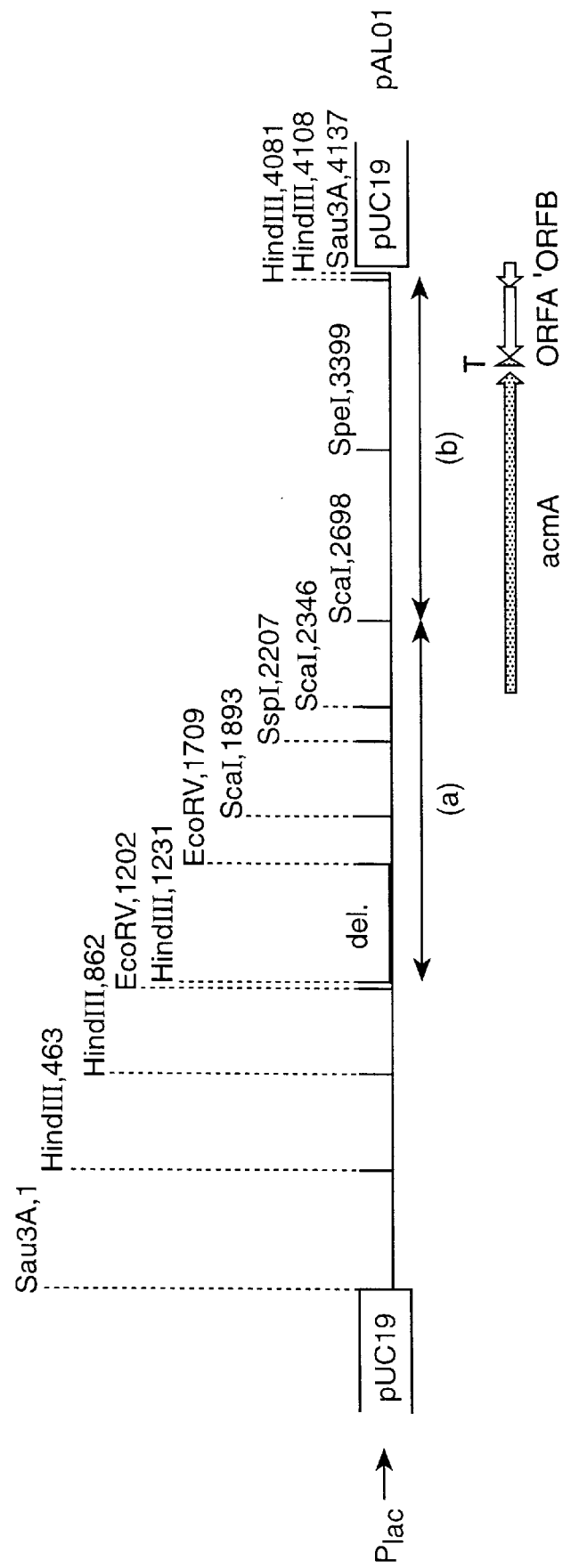
FIG. 3. Restriction enzyme map of the 4137-bp Sau3A DNA fragment of the chromosome of *L. lactis* MG1363 present in pAL01, showing the location of acmA, ORFA and ORFB. T, terminator; $P_{lac}$, lac promoter and its direction of transcription; del., EcoRV deletion made to construct pAL02. The HindIII-SacI fragments used to construct pAL04 and pAL03 are indicated with (a) and (b), respectively. The genetic analysis of the 2207-bp Sau3A-SspI fragment will be presented elsewhere (Buist et al., to be published)

| Strain | Cell fraction | | Supernatant fraction | | |
| --- | --- | --- | --- | --- | --- |
|  | AcmA | PepT | AcmA | Protrel. | PepT |
| WT | ++ | ++ | ++ | ++ | ++ |
| pepT | ++ | − | ++ | ++ | − |
| acmA | − | ++ | − | − | − |
| pepT/acmA | + | + | + | + | + |

DETAILED DESCRIPTION OF THE INVENTION

It is an object of the invention to obtain lysis some hours after the cells have reached the stationary phase, the latter often coinciding with the end of the industrial fermentation. The enhanced induction of the autolysin according to the invention is performed within some hours after the fermentation is finished, in contrast to enhanced lysis after several days as occurs naturally. Alternatively, the enhanced induction can be achieved at the end of the fermentation, with the result that the fermentation is stopped due to the lysis of the cells. The lysis is suitably achieved before 12 hours of the stationary phase have lapsed, preferably before 4 hours of the stationary phase have lapsed.

This deliberately induced production of a higher amount of autolysin at a relatively early stage is the enhanced lysis mentioned in the claims. Therefore, the gene encoding this lysin needs to be under control of a regulatable promoter, i.e. a promoter other than the promoter it is normally associated with. As stated before the presence of a low amount of constitutively produced autolysin is needed for normal cell growth. Therefore the inducible gene must be additional to the existing autolysin gene.

Thus in one aspect of the invention there is provided a process for the lysis of a culture of lactic acid bacteria by means of a lysin, which comprises the in situ production of an autolysin obtainable from Gram-positive foodgrade bacteria esp. from lactic acid bacteria, i.e. not a bacteriophage or active fragments of such autolysin still being capable of lysing the cell walls, the gene encoding said autolysin or a fragment thereof being under control of a regulatable promoter not normally associated with the autolysin gene, to achieve an enhanced lysis during fermentation or shortly thereafter after induction of said regulatable promoter due to an enhanced production of total autolysin compared with the natural production level of the homologous autolysin. Preferably, said regulatable promoter is regulatable by the use of food-grade ingredients or parameters, e.g.

by aeration to induce an oxygen-inducible promoter, by changing the ionic strength or the water activity, in particular the salt content of the culture to induce a salt-inducible promoter, by changing the pH of the culture to induce a pH-inducible promoter, or by applying a lower or higher temperature than used for the growth of the lactic acid bacteria to induce a temperature-inducible promoter. The autolysin gene can be heterologous or homologous to the bacterium strain in which it is incorporated. Preferably it will be homologous. In particular with regard to legislation regarding recombinant DNA work the use of DNA homologous to a bacterium is much sooner approved than when applying heterologous sequences.

An advantage of a process according to the invention is that no extra amount of lysin needs to be added, because during the fermentation the cells multiply and lysin is only formed at the time when it is needed as a consequence of the regulatable promoter, for example when the whey has already been removed. This is more economical in price and manpower than the state of the art processes for introducing lysin as such. Furthermore the lysin need not first be isolated or encapsulated as is needed according to the methods disclosed in WO 90/00599.

Another advantage of a process according to the invention is that the time of lysis of the culture can be controlled rather precisely by choosing an adequate promoter or regulon that can be activated by the parameters of the production process for obtaining the product containing the culture.

It should be noted that a regulon comprises a promoter and operator region, an operator region can be activated or deactivated by the action of a repressor. In this specification a regulatable promoter also comprises a regulatable regulon whereby the expression is regulated by a repressor-operator interaction. Finally this is the first foodgrade system that has been developed and thus can be applied in practice for producing products suitable for human consumption.

The culture of lactic acid bacteria can be used as such, but can also form part of a product containing such culture. The latter occurs when the lactic acid bacteria culture is used for producing a fermented food product obtainable by the fermentative action of the lactic acid bacteria and subsequently the lactic acid bacteria in the fermented food product are lysed. In particular, the fermented food product can be a cheese product. In a preferred embodiment additionally a cheese ripening step is carried out, whereby some of the constituents after leaving the lysed cells will change the composition of the cheese product.

According to another aspect of the invention a process for producing a mixture of peptides is provided, in which a mixture of peptides obtained by proteolysis of proteins is combined with a culture of lactic acid bacteria containing a lactic acid bacterium autolysin gene under control of a regulatable promoter and subsequently the promoter is induced to achieve production of the autolysin in such amount that the lactic acid bacteria are lysed and the contents of the cells containing peptidases will modify the composition of the mixture of peptides. Instead of carrying out the lysis in the peptide mixture itself, it is also possible to first carry out a process for the lysis of a culture of lactic acid bacteria by means of a lysin according to the invention, followed by adding the resulting lysed culture to a mixture of peptides obtained by proteolysis of proteins, and allowing the contents of the cells containing peptidases to modify the composition of the mixture of peptides. The starting materials for the mixture of peptides can be any protein or a mixture thereof, but preferably the proteins comprise milk proteins or vegetable proteins, or both.

According to a further aspect of the invention a process according to the invention is provided, in which first the autolysin is produced and subsequently used as a bactericidal agent against spoiling bacteria, e.g. certain Lactobacillus species that can spoil a product, or pathogenic bacteria, e.g. Gram-positive Listeria species or Gram-negative Salmonella species. To obtain improved results it is desirable that the production of autolysin is enhanced compared with the natural production level. Thus according to this aspect of the invention a process for improving the shelf life of a consumer product is also provided, in which a free autolysin-containing product obtained by a process according to the invention is incorporated into said consumer product in such amount that the growth of spoiling bacteria or pathogenic bacteria is inhibited in the resulting consumer product or that their viability is strongly reduced. The advantage is that no purification is required of the autolysin prior to use.

Such consumer products comprise edible products, cosmetic products, and products for cleaning fabrics, hard surfaces and human skin. Examples of such products may be bread and bread improvers; butter, margarine and low calorie substitutes therefor; cheeses; dressings and mayonnaise-like products; meat products; food ingredients containing peptides; shampoos; creams or lotions for treatment of the human skin; soap and soap-replacement products; washing powders or liquids; and products for cleaning food production equipment and kitchen utensils.

Another aspect of the invention covers the nucleotide sequence encoding the lysin of a lactic acid bacterium. In particular the nucleotide sequence according to sequence id. no. 1 is claimed as are functional equivalents thereof. Variants of this nucleotide sequence e.g. other nucleotide sequences encoding the amino acid sequence according to sequence id. no. 2 as encoded by the nucleotide sequence according to sequence id. no. 1 are also claimed. Fragments of such sequences which upon expression exhibit the activity of a lysin which can be determined with an activity test as illustrated in the description also fall within the scope of the invention. Nucleic acid sequences encoding an N-terminal amino acid sequence that is more than 70%, preferably more than 80%, more preferably 90% homologous with the N-terminal amino acid sequence according to sequence id no 2 and encoding a polypeptide exhibiting lytic activity of an N-acetylmuramidase as can be determined by a standard assay also fall within the scope of the invention. Nucleic acid sequences in addition encoding an overall amino acid sequence that is more than 40%, preferably more than 50%, more preferably between 60–100% homologous with the overall amino acid sequence according to sequence id no 2 and encoding a polypeptide exhibiting lytic activity of an N-acetylmuramidase as can be determined by a standard assay also fall within the scope of the invention. In particular a nucleic acid sequence according to any of the above described embodiments further comprising at least 3 direct repeats in the C-terminal part of the amino acid sequence, said direct repeats being characterised by a homology of more than 75% at amino acid level falls within the scope of the invention. Preferably an amino acid sequence encoded by a nucleic acid sequence according to the invention will comprise serine, threonine and asparagine rich intervening sequences between the direct repeats. More specifically a nucleic acid sequence according to the invention will comprise a part encoding a membrane spanning domain as illustrated in FIG. 5. A nucleic acid sequence according to any of the abovementioned embodiments further characterised by its ability to hybridize to a nucleic acid sequence according to sequence id no 1 and FIG. 4 under normal to stringent conditions common to a person skilled in the art.

Recombinant host cells comprising a sequence according to the invention in any of the abovementioned embodiments under control of a promoter other than that naturally occurring with the lysin gene, said promoter preferably being regulatable and most preferably derived from a foodgrade organism are also covered. Examples of suitable promoters are provided in the European Patent Applications EP-942013541.1 and EP-94201355.8. The details regarding promoters, expression vectors in the various embodiments disclosed in the two cited European Patent Applications are hereby enclosed by reference. In particular foodgrade gram-positive host cells such as lactic acid bacteria are suitable embodiments of host cells. A recombinant host cell according to the invention will also possess a native autolysin gene under control of it's native promoter such that the required degree of autolysin production during the exponential growth phase is ensured.

The invention is further illustrated by two draft publications, which are given below.

Draft Publication 1

MOLECULAR CLONING, NUCLEOTIDE SEQUENCE, AND FUNCTIONAL ANALYSIS OF THE GENE FOR THE MAJOR PEPTIDOGLYCAN HYDROLASE GENE OF *LACTOCOCCUS LACTIS*

SUMMARY

A gene of *L. lactis* subsp. *cremoris* MG1363 encoding a peptidoglycan hydrolase was identified in a genomic library of the strain in pUC19 by screening of *E. coli* transformants for cell wall lysis activity on a medium containing autoclaved, lyophilized *M. lysodeikticus* cells. In cell-free extracts of *L. lactis* MG1363 and several halo producing *E. coil* transformants, lytic bands of similar sizes were identified by denaturing SDS-polyacrylamide gels containing *L. lactis* or *M. lysodeikticus* cell walls. Of these clearing bands, corresponding with the presence of lytic enzymes of 46 kDa and 41 kDa, the 41 kDa band was also present in the supernatant of an *L. lactis* culture. Deletion analysis of one of the recombinant plasmids showed that the information specifying lytic activity was contained within a 2428-bp EcoRV-Sau3A fragment. Sequencing of part of this fragment revealed a gene (acmA) of 1311 bp that could encode a polypeptide of 437 amino acid residues. The calculated molecular mass of AcmA (46.564 Da) corresponded with that of one of the lytic activities detected. Presumably, the enzyme is synthesized as a precursor protein which is processed by cleavage after Ala at position 57, thus producing a mature protein of 40.264 Da, which corresponded with the size of the lytic activity present in culture supernatants of *L. lactis*. The N-terminal region of the mature protein showed 60% identity with the N-terminal region of the mature muramidase-2 of *Enterococcus hirae* and the autolysin of *S. faecalis*. Like the latter two enzymes, AcmA contains C-terminal repeated regions. In AcmA, these 3 repeats are separated by non-homologous intervening sequences highly enriched in serine, threonine, asparagine. Genes specifying identical activities were detected in various strains of *L. lactis* subsp. *lactis* and *L. lactis* subsp. *cremoris* using the SDS-PAGE detection assay and PCR experiments. Using replacement recombination, an acmA deletion mutant was constructed which grew as long chains, indicating that AcmA is required for cell separation.

INTRODUCTION

Bacteria produce several types of cell wall hydrolases, enzymes capable of hydrolysing the peptidoglycan of the cell envelope. Based on their cleavage specificity, the enzymes are classified as N-acetylmuramidases (lysozymes), N-acetylglucosaminidases, N-acetylmuramyl-L-alanine amidases, endopeptidases, and transglycosylases (44). Cell wall hydrolases are thought to be involved in cell wall turnover (11), cell separation, competence for genetic transformation, formation of flagella, sporulation, and the lytic action of some general antibiotics (for reviews see (38,51)).

Strains of the starter bacteria *L. lactis* are of eminent economic importance because of their worldwide use in cheese making. It is generally believed that during cheese maturation, autolysis of the bacteria results in release of intracellular proteolytic enzymes such as a variety of peptidases which digest casein-borne peptides and, thus, may contribute to cheese flavour development (48).

Some data are available on the biochemistry of autolysis and autolytic activity in lactococci. Thus, Mou et al. (31) and Niskasaari (33) have shown that *L. lactis* subsp. *cremoris* shows maximal autolytic activity during exponential growth in media with a neutral pH. These authors could only detect an N-acetylmuramidase, which was present in the cell wall and supernatant fraction; no endopeptidase or glucosaminidase activity was detectable. The lactococcal autolytic activity was inhibited by lipoteichoic acid and cardiolipin and activated by trypsin (33). Mou et al. (31) also showed that the cell walls of exponential-phase *L. lactis* subsp. *cremoris* cells autolyse most readily at the equatorial ring. McDonald (30) noted that in both *L. lactis* and *L. cremorts* filament formation was associated with decreased autolysin activity, an observation later confirmed by Langsrud et al. (25). These data suggest that autolytic activity in *L. lactis* is involved in cell separation.

Although data on the biochemistry of lactococcal autolysins is gradually emerging, nothing is known about the genetic components governing autolysis in *L. lactis*. In this paper we report the cloning, expression and sequence of the gene for the major peptidoglycan hydrolase from *L. lactis*. In addition, a deletion mutant was constructed in order to elucidate the function of the autolysin.

MATERIALS AND METHODS

Bacterial Strains, Plasmids, and Growth Conditions

The strains and plasmids used in this study are listed in Table 1.1. *L. Zactis* was grown in M17 broth (Difco, West Molesey, UK) or whey-based medium (9) at 30° C. as standing cultures, or on M17 agar, all supplemented with 0.5% glucose. Erythromycin (Boehringer Mannheim, GmbH, Germany) and 5-bromo-4-chloro-3-indolyl-β-D-galactopyranoside (X-gal) (Sigma Chemicals Co., St.Louis, Mo.) were added to 5 μg/ml and 0.008% respectively. *E. coli* was grown in TY (Difco laboratories, Detroit, Mich.) medium at 37° C. with vigorous agitation, or on TY medium solidified with 1.5% (wt/vol) agar, containing 100 μg/ml of ampicillin (Sigma), 50 μg/ml of kanamycin (Boehringer) or 100 μ/ml erythromycin (Boehringer), when required. Isopropyl-β-D-thiogalactopyranoside(IPTG) and X-gal (both from Sigma) were used at concentrations of 1 mM and 0.002% (wt/vol), respectively.

General DNA Techniques and Transformation

Molecular cloning techniques were performed essentially as described by Sambrook et at. (39). Restriction enzymes, Klenow enzyme, T4 DNA polymerase, T4 DNA ligase and deoxynucleotides were obtained from Boehringer Mannheim and were used according to the instructions of the supplier. Genomic DNA of *L. lactis* was isolated according to the method described by Leenhouts et al. (28) with one modification: cell pellets resuspended in lysis solution with lysozyme were incubated at 55° C. for 15 minutes (41). *E. coli* and *L. lactis* were transformed by electroporation using a Gene Pulser™ (Bio-Rad) as described by Zabarovsky and Winberg (55) and Holo and Nes (15) with the modifications suggested by Leenhouts and Venema (29), respectively.

Sample Preparation for SDS-PAGE

After overnight growth, the optical density of the *L. lactis* cultures was measured in a Philips PU8720 UV/VIS scanning spectrophotometer (Pye Unicam Ltd, Cambridge, UK) at 600 nm.

TABLE 1.1

Bacterial strains and plasmids

| Strains | Relevant phenotype or genotype | Source or reference |
|---|---|---|
| *L. lactis* subsp. *cremoris* | | |
| MG1363 | Plasmid-free strain | (13) |
| MG1363::pINTAA-1 | Em$^r$, β-GAL$^+$, derivative of MG1363 with integrated pINTAA via portion 1 | This work |
| MG1363::pINTAA-2 | Em$^r$, β-GAL$^+$, derivative of MG1363 with integrated pINTAA via portion 2 | This work |
| MG1363acmAΔ1 | Derivative of MG1363 containing a 701 bp ScaI/SpeI chromosomal deletion in the acmA gene | This work |
| AM1 | Wild-type strain | (12) |
| HP | Wild-type strain | New Zealand Dairy Research Institute (NZDRI) |
| *L. lactis* subsp. lactis | | |
| IL1403 | Plasmid-free strain | (5) |
| *L. lactis* subsp. lactis biovar diacetylactis | | |
| 18-16S | Sm$^r$ | (14) |
| *E. coli* | | |
| NM522 | supE, thi, Δ(lac-proAB), Δhsd5(r-, m--) [F', proAB, lacI$^q$ZM15] | Stratagene (La Jolla, CA.) |
| EC1000 | Km$^r$, glgB, derivative of MC1000 containing the repA gene of the lactococcal plasmid pWV01 | Laboratory collection |
| pBluescript SK+ | Ap$^r$ | Stratagene |
| pUC19 | Ap$^r$ | (53) |
| pUK21 | Km$^r$ | (47) |
| pORI280 | Em$^r$, β-GAL$^+$, ori of pWV01; integration vector which replicates in strains containing RepA | (27, 29) |

TABLE 1.1-continued

Bacterial strains and plasmids

| Strains | Relevant phenotype or genotype | Source or reference |
|---|---|---|
| pAL01 | Ap$^r$, pUC19 carrying a 4137 bp lactococcal chromosomal DNA insert with the cell-wall hydrolase gene | This work |
| pAL02 | Ap$^r$, pAL01 with a 507 bp EcoRV deletion | This work |
| pAL03 | Km$^r$, pUK21 with a 1383 bp HindIII/SacI insert of pAL01 | This work |
| pAL04 | Km$^r$, pUK21 with a 1467 bp HindIII/SacI insert of pAL01 | This work |
| pAL05 | Ap$^r$, SK+ with a 682 bp HindIII/SpeI fragment of pAL03 | This work |
| pAL06 | Ap$^r$, SK+ with a 701 bp SacI/SpeI fragment of pAL03 | This work |
| pAL07 | Ap$^r$, SK+ with a 477 bp ScaI/ClaI fragment of pAL04 | This work |
| pAL08 | Ap$^r$, pAL01 with a 16 bp SmaI/EcoRI deletion | This work |
| pAL09 | Ap$^r$, pAL08 with a 701 bp SacI/SpeI deletion | This work |
| pINTAA | Em$^r$, β-GAL$^+$, pORI280 with a 2247 bp EcoRV/HindIII fragment of pAL09 | This work |

5 milliliters of the cultures were subjected to centrifugation and the supernatant fractions were dialysed against several changes of demineralized water, lyophilized. and dissolved in 1 ml denaturation buffer (2). The cell pellets were resuspended in 1 ml denaturation buffer and cell free extracts were prepared as described by van de Guchte et al. (45). Cell free extracts of E. coli strains were made accordingly after pelleting 2 ml of overnight cultures. The samples were boiled for 5 minutes and centrifuged before loading. SDS-polyacrylamide (SDS-PAA) gel electrophoresis was carried out as described by Laemmli (24) with the Protean II Minigel System (Bio-Rad Laboratories, Richmond, Calif.). Prestained molecular weight markers were obtained from Bio-Rad and Pharmacia (Pharmacia AB. Uppsala, Sweden).

Detection of Lytic Activity in SDS-PAA Gels

Lytic activity was detected in situ by using 12.5% (wt/vol) SDS-PAA gels containing 0.2% (wt/vol) autoclaved, lyophilized M. lysodetkticus ATCC 4698 cells (Sigma), or cell walls of L. lactis MG1363. Cell walls of L. lactis MG1363 were isolated using the method of Potvin et at. (37) with the following modification: after resuspension in 4% (wt/vol) SDS, the cells were disrupted as described by van de Guchte et al. (45). After electrophoresis, the gels were gently shaken at room temperature for 24 to 48 h in 3 to 5 changes of 100 ml 25 mM Tris-HCl (pH 7) containing 1% (vol/vol) Triton X-100 to allow for protein renaturation (37). Bands of lytic activity were visualised by staining with 1% (wt/vol) Methylene Blue (Sigma) in 0.01% (wt/vol) KOH and subsequent destaining with demineralized water (17). SDS-PAA gels without cell walls were stained with Coomassie Brilliant Blue or with the Bio-Rad Silver Stain Kit (Bio-Rad).

Construction of a chromosomal gene library of L. lactis MG1363 in E. coli screening for lytic activity against M. lysodeikticus A library of L. lactis MG1363 chromosomal DNA was constructed according to Zabarovsky and Allikmets (54) with some modifications. Genomic DNA of L. lactis MG1363 was digested for 15 minutes with the appropriate amount of Sau3A to generate partial digests. After electrophoresis in ultrapure agarose (Pharmacia) of the chromosomal digest, fragments of 4 to 10 kb in size were isolated from the gel using electroelution. The isolated chromosomal DNA fragments, partially filled-in with dATP and dGTP, and pUC19 DNA linearized with SalI and partially filled-in with dTTP and dCTP, were ligated, and the ligation mixture was used to electrotransform E. coli NM522. After electroporation the cells were plated on TY plates containing 0.2% (wt/vol) autoclaved, lyophilized M. lysodeikticus cells and placed at 37° C. After 2 days the plates were placed at room temperature and examined daily for the appearance of halos around the colonies.

Molecular Cloning and DNA Sequencing.

Figure 12B:
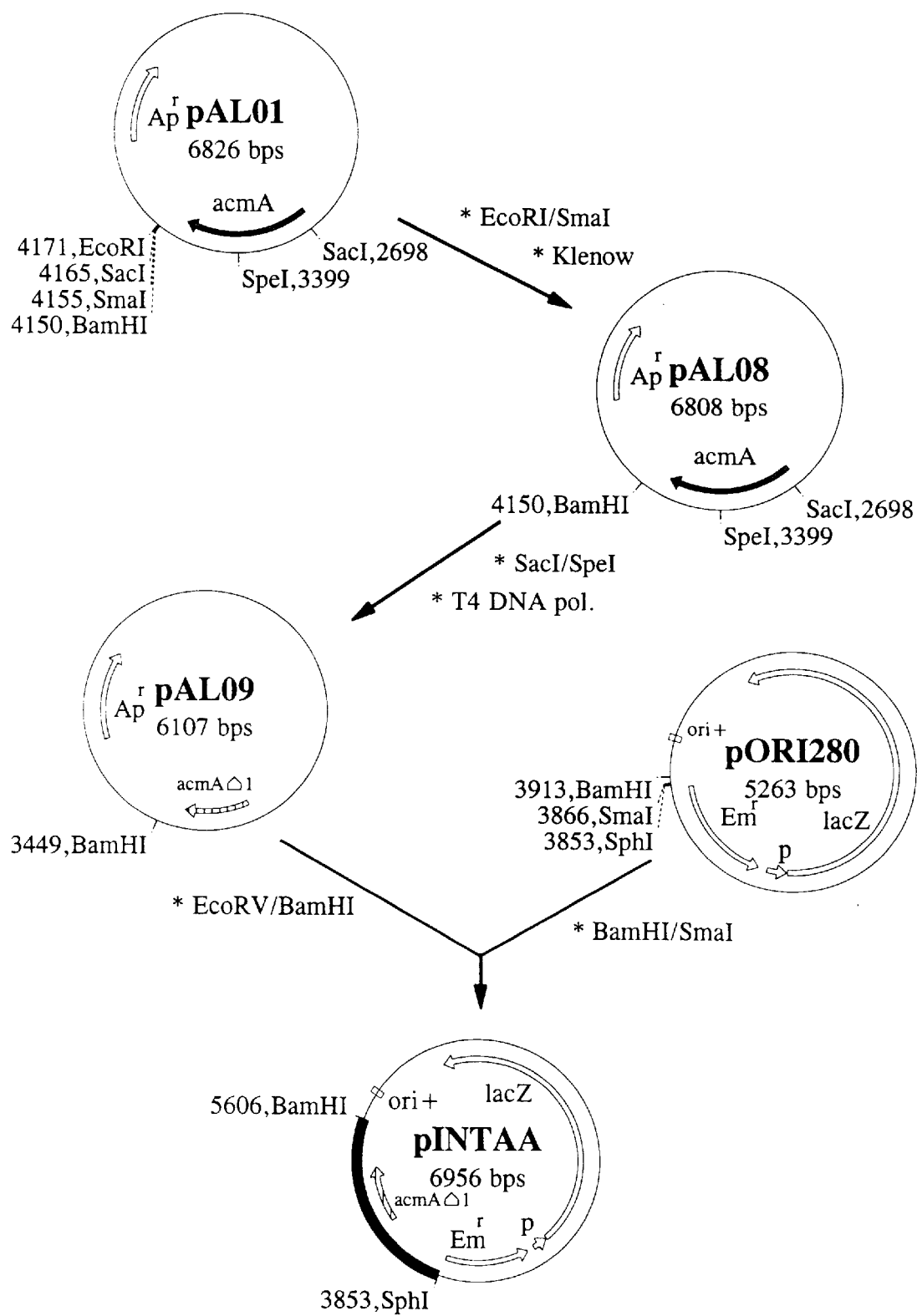

The two HindIII-SacI fragments of 1467 and 1383 bp of pAL01, indicated with (a) and (b) in FIG. 3, were subcloned into the HindIII and SacI sites of pUK21 and the resulting plasmids were designated pAL04 and pAL03, respectively (see FIG. 12.A-1). The insert of pAL04 was subcloned in two fragments using the unique SpeI site: pAL05 was constructed by digestion of pAL03 with SpeI and HindIII and subcloning of the 682-bp fragment into the HindIII and SpeI sites of pBluescript SK+: the other part of the insert of pAL04 was subcloned as a SpeI-SacI fragment of 701 bp into the same sites of pBluescript SK+. This subclone was named pAL06. The 352-bp ScaI-SacI fragment of pAL03 was subcloned as a ScaI-ClaI fragment into the SmaI and ClaI sites of pBluescript SK+, resulting in pAL07 (see FIG. 12.A-2).

Both strands of the inserts of the various subclones were sequenced by the dideoxy-chain-termination method (40) with the T7 sequencing kit (Pharmacia) and double-stranded plasmid templates according to the manufacturer's instructions using universal and reverse pUC primers. The sequence was completed using synthetic DNA primers. Primers were synthesized with an Applied Biosystems 381A DNA Synthesizer (Applied Biosystems, Inc., Foster City, Calif.). DNA nucleotide and amino acid sequences obtained were analyzed with the PC/GENE (version 6.7) sequence analysis program (IntelliGenetics, Inc., Geneva, Switzerland). Protein homology searches were carried out with the data bases SWISSPROT (release 27) and the ATLAS of protein and genomic sequences (March, 1994) by means of the FASTA program (35).

Southern Transfer, DNA Hybridisation, and PCR

After agarose gel electrophoresis DNA was transferred to GENE-SCREEN PLUS membranes (NEN Research Products, Boston, Mass.) by the protocol of Southern, as modified by Chomczynski and Quasba (4). Probe labelling and hybridisation was done with the ECL labelling and detection system according to the instructions of the manufacturer (Amersham International, Amersham, UK).

PCR reactions were carried out with SUPER TAQ DNA-polymerase according to the instructions of the manufacturer (HT BIOTECHNOLOGY LTD, Cambridge, England) on chromosomal DNA using the primers combinations PALA-4 (SEQ ID NO:6)(5'-CTTCAACAGACAAGTCC) and PALA-14 (SEQ ID NO:7)(5'-GATAAATGATICCAAGC), both located within the acmA gene (FIG. 4), or PALA-19 (SEQ ID NO:8)(5'-CAAGGTTAAGTCCACG), which is located upstream of the insert of pINTAA, and BK05AL (SEQ ID No:9)(5'-ATTATTTGATTGGAGTT), which is located in the origin of replication of pORI280, designated with x and y in FIG. 8, respectively.

Construction of an acmA Deletion Strain

A replacement recombination system developed by Leenhouts and Venema (27,29) was used to replace acmA by an acmA gene with an internal deletion on the chromosome of L. lactis MG1363. See FIG. 12.B for a scheme showing the construction of pINTAA. A unique SacI site in acmA was obtained by cutting pAL01 with EcoRI and SmaI. The plasmid DNA was treated with Klenow enzyme, ligated, and used to electrotransform E. coli NM522. The resulting plasmid pAL08 was digested with SacI and SpeI, treated with T4 DNA polymerase, ligated, and used to electrotransform E. coli NM522, giving plasmid pAL09. pAL09 was digested with BamHI and EcoRV, and the DNA fragment containing the deleted acma gene was subcloned into the BamHI and SmaI sites of pORI280. The ligation mixture was used to electrotransform E. coli EC1000. The resulting integration plasmid, named pINTAA, was used to electrotransform L. lactis MG1363. Selection of the second cross-over event was done as described by Leenhouts and Venema (29).

RESULTS

Analysis of Peptidoglycan Hydrolase Activity of L. lactis MG1363

The peptidoglycan hydrolysing activity of GM17 or whey-grown L. lactis MG1363 was examined by SDS-PAGE in the presence of either autoclaved, lyophilized M. lysodeikticus cells, or isolated cell walls of Lactococcus lactis MG1363 as a substrate (FIG. 1). Eleven different clearing bands, corresponding to proteins ranging in size from 29 to 111 kDa, were detected in the supernatant fraction of the whey culture, but only three of these were detectable in this fraction of the GM17 culture when autoclaved M. lysodeikticus cells were used as a substrate. Three activities above the 46 kDa band detected in the supernatant fraction of whey-grown cells were not detectable in the supernatant fraction of cells grown in GM17. With cell walls of L. lactis MG1363, only 3 bands could be detected in the supernatant of the whey-grown cells and only one in the GM17 culture supernatant. In the cell-free extracts of the two cultures only two clear bands were observed, corresponding to 41 and to 46 kDa proteins, when using M. lysodeikticus cells as a substrate. Only the smaller band was found in gels containing isolated lactococcal cell walls. All the activities could be detected when buffered TRITON X-100 ranging from pH 3 to 10 was used in renaturation, but the staining conditions were optimal after renaturation at pH 7. When samples were run on SDS-PAA gels without substrate, protein bands corresponding with the clearing bands could neither be detected in the cell-free extract, nor in the supernatant fraction after staining with Coomassie brilliant blue and subsequent silver staining (results not shown).

Peptidoglycan hydrolytic activity was also detected on GM17 agar plates in which 0.2% (wt/vol) autoclaved, lyophilized M. lysodeikticus cells had been incorporated. Hydrolysis of the cell walls could be seen as zones of clearing around colonies of L. lactis MG1363 after 36 h of incubation at 30° C.

When a proteinase-positive strain of L. lactis MG1363 was examined for peptidoglycan hydrolase activity by SDS-PAGE only a few of the small clearing bands were present in the supernatant fraction. The bands in the cell-free extract were the same as those seen in a proteinase-deficient strain (results not shown).

Cloning of the Gene of the Major Peptidoglycan Hydrolase of L. lactis MG1363

The average insert size of the genomic library of L. lactis MG1363 in PUC19 was 6 kb. Of approximately 8000 colonies tested, 13 produced a halo on TY plates containing M. lysodeikticus cells. Renaturing SDS-PAGE on cell-free extracts of these E. coli clones showed that all produced clearing bands of approximately 46 and 41 kDa (FIG. 2). A 46-kDa band present in E. coli was present in the lactococcal cell fraction only, whereas a 41-kDa band produced by E. coli was observed in both the cell-free extract and supernatant fraction of L. lactis. Furthermore, several faster migrating bands were visible when cell-free extracts of the positive E. coli clones were analyzed. The sizes of the inserts in pUC19 of the 13 E. coli clones ranged from 4.1 to 9 kb. Restriction enzyme analysis showed that the plasmids isolated from all lysin-producing colonies shared a 4.1-kb Sau3A insert. A clone containing only this 4.1-kb fragment showed growth problems. An overnight culture of the strain foamed heavily and flocculation of cells was observed in the culture by visual inspection and by light microscopy. This clone was selected for further experiments and its plasmid was designated pAL01. A restriction map of the insert is presented in FIG. 3. Various restriction enzyme digests of chromosomal DNA of L. lactis MG1363 were analyzed by Southern hybridization using the 4.1-kb Sau3A insert of pAL01 as a probe. No rearrangements were found as judged from a comparison of the restriction map of this fragment and the corresponding chromosomal DNA (results not shown).

The 507-bp EcoRV fragment of pAL01 could be deleted without loss of any of the clearing bands. As the activity band with the highest molecular weight present in the E. coli(pAL02) cell-free extracts was 46 kDa, and because the coding capacity of the smallest of the Sau3A-EcoRV fragments (1201-bp) was too little to encode a protein of 46 kDa, the 2434-bp EcoRV-Sau3A fragment was subcloned and sequenced.

Nucleotide sequence of the lactococcal gene for peptidoglycan hydrolase

The two SacI-HindIII fragments (a) and (b) of pAL01 (see FIG. 3.) were subcloned into pUK21 and several smaller subclones were made using pBluescript SK+ (see FIG. 12.A-1 and 12.A-2). The nucleotide sequence of the 1930-bp SspI-Sau3A fragment pAL01 is presented in FIG. 4 and Sequence id no 1 and shows that it contains two complete open reading frames (ORF's), one of 1311 bp (acmA) and one of 282 bp (ORFA). Upstream of ORFA a part of a third ORF was found suggesting that ORFA is the last ORF of an operon. Both ORFA and acmA are preceded by putative ribosome-binding sites complementary to the 3' end of the lactococcal 16S rRNA (3) and have $\Delta G°$'s of $-9.7$ and $-9.6$ kcal/mol, respectively (43). Also, a possible $-10$ and $-35$ region with a spacing of 23 bp is present upstream of acmA. The putative $-10$ region is preceded by the sequence TGN, which is found in more than 40% of the lactococcal promoters analyzed so far (8). Downstream of this ORF an inverted repeat with a $\Delta G°=-16$ kcal/mol is located that may function as a rho-independent terminator (36). The sequenced fragment has a G+C content of 36.2%. which is in agreement with the G+C content determined for *L. lactis* (38.6%; (32)). The codon usage of acmA and ORFA are in agreement with that calculated by van de Guchte et al.(46) from several sequenced *L. lactis* genes.

Deduced Amino Acid Sequences and Homology Comparisons acmA could encode a protein of 437 amino acids with a deduced molecular weight of 46.564. The first 57 amino acids constitute a putative signal peptide (49) and a membrane spanning domain was identified within this stretch of amino acids (FIG. 5 and sequence id no 3). Cleavage of this putative signal peptide would result in a protein of 40.264 Da. The entire protein has an isoelectric point (PI) of 10.45. The protein without the putative signal sequence has a PI of 10.12.

A high degree of similarity of the N-terminal part of AcmA was found with muramidase-2 of *Enterococcus hirae* (6), and the autolysin of *S. faecalis* (2), and a low degree of similarity was observed with the flagellar protein FlgJ of *Salmonella typhimurium* (19). An identity of approximately 56% was found between AcmA and the autolysins of *Enterococcus hirae* and *S. faecalis* between amino acids 65 and 220 (FIG. 5A and sequence id 2). From these data, combined with the biochemical data available from literature (31,33), and the results presented below, we conclude that we have cloned the gene encoding the major lysozyme (N-acetylmuramidase) of *L. lactis*. Therefore the gene was called acmA.

In the C-terminal part of the protein three repeated regions were present. The regions are 44 amino acids long and are separated by intervening sequences highly enriched for serine, threonine, and asparagine residues. The overall similarity between the repeated regions is approximately 75% (FIG. 6). At the DNA level the homology is only 45%. The repeated regions in the C-terminal part of AcmA have homology with the C-terminal repeated regions of the cell wall hydrolases of *Enterococcus hirae* and *S. faecalis*. The organisation of these repeats in the three enzymes is schematically presented in FIG. 5B. This part of AcmA also shows homology with protein P60 of *Listeria monocytogenes*, which recently has been shown to possess peptidoglycan hydrolase activity (52).

ORFA could encode a protein of 94 amino acids with a molecular size of 11.287 Da. The ORFA product has a homology of 64% (19% identity) with an 11.2 kDa hypothetical protein in the rfah-fre intergenic region of the *E. coli* chromosome (1,7).

Detection of acmA and its Gene Product in Other Lactococcal Strains.

Figure 7:
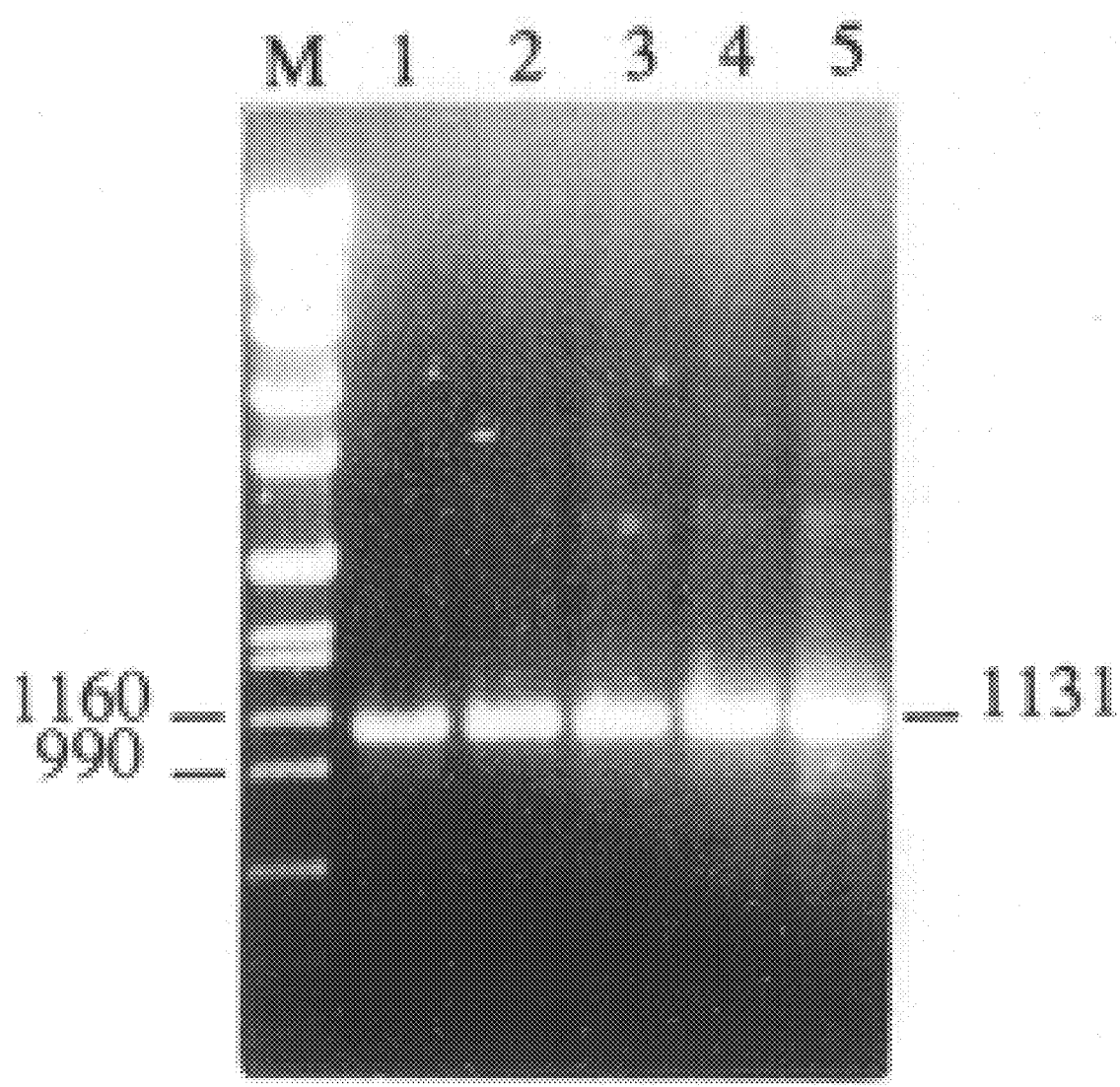
FIG. 7. PCR products formed on chromosomal DNA's of the lactococcal strains MG1363(1); IL1403(2); 18-16s(3); AM1(4) and HP(5). Primers used were PALA-4 and PALA14 shown in FIG. 4. M, molecular weight marker: bacteriophage SPPI DNA cut with EcoRI. Sizes indicated in the margins are in basepairs.

*L. lactis* subsp. *lactis* IL1403, *L. lactis* subsp. *lactis* biovar diacetylactis 18-16S, and the *L. lactis* subsp. *cremoris* strains AM1, HP, and MG1363 were grown in GM17 for 36 hours. Cell-free extracts were prepared and analyzed by renaturing SDS-PAGE using *M. lysodeikticus* cells as a substrate. Major bands of lytic activity at positions corresponding to sizes of 41 and 46 kDa were detected in all strains (results not shown). This result was complemented with PCR using the two sequencing primers PALA-4 and PALA-14 (see FIG. 4) and the data are shown in FIG. 7. From the chromosomal DNA's of all strains the same 1131-bp DNA fragment was amplified. These results indicate that all strains contain the same major peptidoglycan hydrolase activity which, in strain AM1, has been identified as an N-acetylmuramidase (31).

Construction and Analysis of a Chromosomal acmA Deletion Mutant

Figure 9:
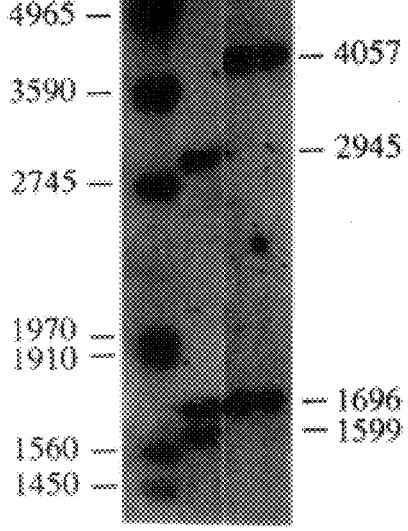
FIG. 9. Southern blot analysis of the mutant strain *L. lactis* MG1363 acmAΔ1. Chromosomal DNA's of MG1363 (1), MG1363 acmAΔ1-a(2), and MG1363 acmAΔ1-b(3) digested with HaeIII were separated on a 0.8% agarose gel, transferred to gene screen-plus membrane, and hybridized to the 4137 bp Sau3A insert of pAL01. M, molecular weight marker: bacteriophage SPPI DNA cut with EcoRI, of which the sites (in bp) are given on the left. The sizes (in bp) of the hybridising bands of the chromosomal DNA's are shown in the right margin.

To investigate the function of AcmA a deletion was introduced in the chromosomal copy of acmA by replacement recombination (27,29), After transformation of *L. lactis* MG1363 with pINTAA, which carries an acmA gene with an internal deletion (FIG. 12.B), the integrants (Em$^r$ and β-galactosidase-producing) were checked by PCR using the primers PALA-19 and BK05AL (x and y in FIG. 8, respectively). Integration via portion 1 of the insert of pINTAA resulted in a PCR product of 2550 bp. integration via portion 2 in a PCR product of 3247 bp. Three quarters of the integrants obtained had integrated via portion 1 (results not shown). One of these integrants was used for further experiments. Excision of the integrated plasmid was established after non-selective growth for 30 to 35 generations in GM17. Cells were plated on GM17 plates containing X-gal and 0.2% (wt/vol) autoclaved, lyophilized *M. lysodeikticus* cells and screened for loss of blue staining and halo formation. The chromosomal DNA's of two such colonies were analyzed by Southern hybridisation to show the loss of the HaeIII site located between the SacI and SpeI sites in acmA (FIG. 8). As expected. in the chromosomes of both strains a fragment of 4057 bp instead of two fragments of 2945 bp and 1599 bp (FIG. 9) was present. This result indicates that acmA is not an essential gene in *L. lactis*.

Figure 10:
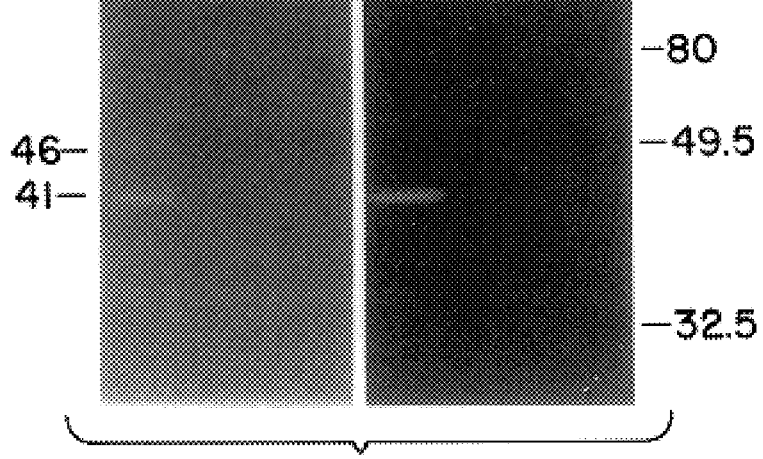
FIG. 10. AcmA activity in *L. lactis* MG1363 (lanes 1,4) and deletion mutants MG1363 acmAΔ1-a (lanes 2,5) and acmAΔ1-b (lanes 3,6) by renaturing (12.5%) SDS-PAGE. The gel contained 0.2% (wt/vol) *M. lysodeikticus* autoclaved cells. Cell-free extracts (lanes 1,2,3) and supernatant fractions (lanes 4,5,6) after growth in GM17 were applied. The amount of sample was equalized according to the optical density of the cultures. Molecular masses of standard proteins are shown on the right and of mature AcmA (46) or its secreted form (41) are shown on the left (all in kilodaltons).

Cell-free extracts and supernatant fractions of the two deletion mutants and MG1363 grown in whey-based medium or GM17 were analyzed on a renaturing SDS-PAA gel containing autoclaved *M. lysodeikticus* cells as a substrate. FIG. 10 shows that in both deletion mutants no cell wall hydrolase activity was present, neither in the cell-free extracts nor in the supernatant fractions in GM17-grown cells. Also after growth in whey-based medium, no clearing bands could be detected (results not shown). The fact that all the clearing bands normally present in cell free extracts and supernatant fractions of *L. lactis* (see FIG. 1) had disappeared after inactivation of acmA shows that all originated from AcmA.

Figure 11A:
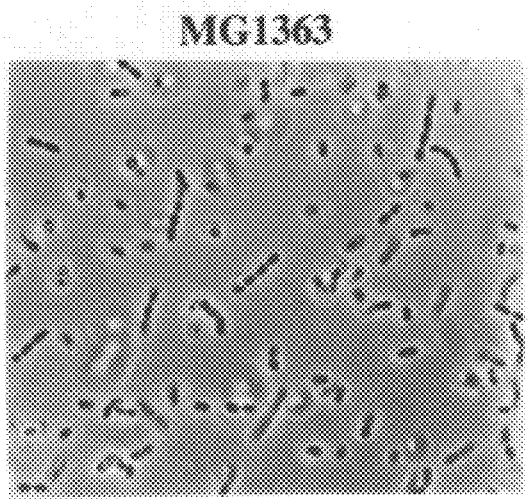
FIG. 11. Light microscopic view of *L. lactis* MG1363 (FIG. 11A), and MG1363 acmAΔ1 (FIG. 11B) at 1000-fold magnification. Both strains were grown overnight in GM17.

After overnight growth in both media precipitation of MG1363acmAΔ1 was observed. The cells of MG1363 and of MG1363acmAΔ1 were examined by light microscopy. MG1363acmAΔ1 formed very long chains as compared to MG1363 (see FIG. 11), indicating that the major lactococcal peptidoglycan hydrolase, AcmA, is needed for cell separation.

The data presented above, conclusively show that *L. lactis* contains only one major peptidoglycan hydrolase, which is a N-acetylmuramidase (lysozyme) needed for cell separation.

DISCUSSION

In this report we present the cloning of the first peptidoglycan hydrolase of the genome of a lactic acid bacterium. The gene encodes the major peptidoglycan hydrolase of *Lactococcus lactis*. Using PCR and denaturing SDS-PAGE the gene was detected in all *L. lactis* strains used and, in fact, in all strains tested so far (unpublished observation). Because the gene was also detected in strain AM1, in which Mou et al. (31) observed only a muramidase activity in the cell wall fraction, we conclude that the cloned gene encodes the lactococcal N-acetylmuramidase, an enzyme hydrolysing the linkages between N-acetylmuramic acid and N-acetylglucosamine moieties and was. Accordingly, the gene was designated acmA. Using a standardized assay to detect autolytic activity in a denaturing polyacrylamide gel, several lytic bands were found in both the cell and supernatant fractions of an *L. lactis* culture using *M. lysodeikticus* cell walls as a substrate, but only a few of these bands were found when cell walls of the host were used. This result indicates that the lytic activities of L. lactis are far better detectable with *M. lysodetkticus* cell walls as a substrate. This has also been observed by Leclerc et al. (26) when they analyzed bacterial extracts of *Clostridium perfringens, Bacillus megaterium* or *S. faecalis*. Comparison of the cell and supernatant fractions of the wild-type lactococcal strain and an acmA deletion mutant revealed that all the lytic bands present in the former originated from AcmA, as all had disappeared in the deletion mutant. As the smallest of the active bands corresponded to a molecular size of approximately 29 kDa, a large part of AcmA can be removed without major loss of activity. As the active site resides, most probably, in the N-terminus (see below) the deletions are thought to occur in the C-terminal repeated region. Degradation of cell wall hydrolases, without loss of activity, has been observed before in *Bacillus licheniformis* (34) and *Bacillus subtilis* (22,23,37). In cell-free extracts of *E. coli* cells expressing acmA, two bands, one of 46 and one of 41 kDa, and several smaller bands were present upon renaturing SDS-PAGE using cell walls of *M. lysodeikticus*. Bands of 41 and 46 kDa were also detected in cell-free extract of *L. lactis* but only the smaller of the two was found in the supernatant fraction of *L. lactis*. acmA encodes a protein of 437 amino acids and the calculated molecular mass of AcmA (46.564 Da) corresponds to the size of the largest clearing band in the lactococcal cell-free extract (46 kDa). Within the deduced amino acid sequence of AcmA a putative signal sequence of 57 amino acids was identified using the rules of von Heijne (49). In contrast to most signal peptides from Gram-positive bacteria, the n-region of this putative signal sequence consists of 29 amino acids with 12 charged amino acid residues instead of eight to twelve (50). This is similar to the signal sequence of muramidase-2 of *Enterococcus hirae* which has 11 charged amino acids within the first 29 amino acids (6). Based on a signal peptide of 57 amino acids, the molecular mass of mature AcmA would be 40.264 Da, which corresponds to the size (41 kDa) of the major clearing band in the culture supernatant of *L. lactis*. Most probably, AcmA is produced as a preprotein and the secreted form is the 41-kDa protein found in the supernatant of an *L. lactis* culture. The 46-kDa preprotein is either produced in lower amounts or has a reduced activity in the assay used, as the corresponding band of activity is always less clear. The 41-kDa protein that is present in the cell-free extract is, most likely, the enzyme that is still attached (with the C-terminal repeat region (see below)) to the whole cell. The deduced amino acid sequence of AcmA shows overall similarity with muramidase-2 of *Enterococcus hirae* (6) and the autolysin of *S. faecalis* (2). The identity was very high in the N-terminal regions of the three proteins which, most probably, encompass the active site (20). Within this region homology was also found with the flagellar protein FlgJ of *Salmonella typhimurium* (19). In the C-terminal part of AcmA, three repeated regions were present separated by nonhomologous sequences rich in serine, threonine, and asparagine residues. Muramidase-2 possesses six of such repeated regions separated by the same kind of nonhomologous sequences as in AcmA. Within the repeats a consensus sequence was postulated by Joris et al. (20). From the homology comparison it is clear that AcmA. muramidase-2, and the autolysin of *S. faecalis* contain 3, 6, and 5 of such consensus sequence, respectively. All three cell wall hydrolases have a repeat at their extreme C-terminus. Similar repeats have also been detected in the *Bacillus subtilis* φPZA lysozyme, the homologous Bacillus gene 15 lysozyme, *Listeria monocytogenes* pathogenicity-associated protein p60, and *Staphylococcus aureus* protein A by Joris et al. (20). and in the sporulation related τ-D-glutamyl-(L)meso-diaminopimelic-acid-hydrolysing peptidase I of *Bacillus sphaericus* by Hourdou et al.(16). We also found this consensus twice in the N-terminal part of DniR of *E. coli*, a protein affecting the anaerobic expression of the hexaheme nitrite reductase (21), of which the second repeat showed some similarity with the first repeat of AcmA. The repeated regions are thought to be involved in substrate recognition and, thus, cell-wall binding (20).

The acmA deletion mutant grows in long chains causing precipitation of the culture after overnight growth. This result proves that AcmA is involved in cell separation as has been found previously by McDonald et al. (30) and confirmed by Langsrud et al. (25). The p60 protein of *Listeria monocytogenes* (52) and muramidase-2 of *Enterococcus hirae* (10) were also found to have an essential role in cell separation. Further analysis of the deletion mutant will reveal whether acmA is the only lactococcal gene encoding a peptidoglycan hydrolase or whether *L. lactis* contains a second muramidase as is the case in *Enterococcus hirae* (42). No halos were present when the deletion mutant was plated on GM17 containing *M. lysodeikticus* cell walls indicating that *L. lactis* does not express hydrolases that would have been missed in the denaturing SDS-PAGE procedure used here. The results obtained with the proteinase positive *L. lactis* strain indicate that the activity of the autolysin is partly regulated by proteolytic degradation, as has been observed in *Bacillus subtilis* (18). The fact that in the supernatant of an *L. lactis* culture no protein could be detected in an SDS-PAA gel corresponding to the lytic bands observed in an activity gel suggests that the expression of the cell wall hydrolase is very low, which is the subject of current research.

Draft Publication 2

AUTOLYSIS OF *L. LACTIS* CAUSED BY INDUCED OVERPRODUCTION OF THE MAJOR AUTOLYSIN AcmA

SUMMARY

Growth analysis of a culture of *Lactococcus lactis* subsp. *cremoris* MG1363 and a mutant of this strain, containing a deletion in the major autolysin gene acmA, showed that autolysis of the mutant strain was almost absent during prolonged stationary growth. In contrast, the optical density of the wild-type strain *L. lactis* MG1363 was reduced to more than 50% in the same period. Complementation studies taught that the acmA promoter was located within a 138 bp SspI-ScaI fragment upstream of the structural gene. An acmA mutant with a plasmid-encoded acmA gene and, thus containing more copies of acmA than the wildtype, lysed to a higher extent than the wildtype strain during prolonged stationary growth. In trans action of AcmA was shown by mixing end-exponential-phase cultures of an acmA deletion mutant and a tripeptidase (pepT) deletion mutant. PepT, produced by the acmA deletion strain, was detected in the culture supernatant of the mixed culture indicating that lysis of the acmA mutant was due to the action of AcmA secreted by the pepT minus cells. A plasmid was constructed in which the lactococcal major autolysin gene, lacking its own promoter, was placed downstream of an inducible promoter/operator region of the temperate bacteriophage RI-t. After induction with mitomycin C of an early exponentially growing culture of *L. lactis* LL302, containing this plasmid, the cells became subject to autolysis, as shown by means of a denaturing SDS-polyacrylamide gel containing *Micrococ-* cus lysodeiktidus cell walls as a substrate and the release of intracellularly located proteins.

INTRODUCTION

Autolysins are potentially lethal enzymes which hydrolyse the peptidoglycan of the cell wall. Recently we succeeded in cloning the major autolysin acmA of *Lactococcus lactis* subsp. *cremoris* MG1363. AcmA is a lysozyme-like enzyme (muramidase) that hydrolyses the N-acetylmuramyl, 1,4,-β-N-acetylglucosamine bonds in the peptidoglycan. AcmA was shown to be required for cell separation (2).

Vagerud et al. (24) and Langsrud et al. (9) have monitored autolysis of group N streptococci for prolonged period and observed different rates of autolysis among the strains tested. Vagerud et al. (24) showed that autolysis of lactococci was maximal in buffered M17-medium with glucose as carbon source. Langsrud et al. (9) showed that the activity of intracellularly located lactate dehydrogenase could be detected in the culture supernatant after autolysis.

The proteolytic activities of lactococci are involved in ripening and in flavour development in fermented milk products, especially cheese (16,22). Lactococci contain several intracellularly located peptidases (18,20). Release of these peptidases after spontaneous lysis of the cells is believed to be involved in cheese maturation and flavour development (29). Maturation is a slow and therefore, a costly process, which might be accelerated by enhanced lysis of cells and thus, the quick release of intracellular peptidases. In this report we show that, in principal enhanced autolysis can be obtained by using the recently characterized promoter/operator region which is controlled by the temperate lactococcal bacteriophage RI-t repressor (14.28).

MATERIALS AND METHODS

Bacterial Strains, Plasmids, and Growth Conditions.

The strains and plasmids used in this study are listed in Table 2. *Lactococcus lactis* was grown in ½*M17 broth (Difco, West Molesey, United Kingdom) at 30° C. or on M17 broth solidified with 1.5% agar, all of which were supplumented with 0.5% glucose. During the growth analysis of the MG1363 and MG1363acmAΔ1, both strains were grown on 1*M17. When needed, 5 μg/ml erythromycin was added (Boehringer GmbH Mannheim, Germany). *Escherichia coli* was grown in TY (Difco laboratories, Detroit, Mich.) medium at 37° C. with vigorous agitation, or on TY medium solidified with 1.5% (wt/vol) agar containing 100 μg of ampicillin (Sigma Chemical Co., St.Louis, Mo.) or 100 μg of erythromycin per ml, when required.

General DNA Techniques and Transformation.

Molecular cloning techniques were performed essentially as described by Sambrook et al. (19). Restriction enzymes, Klenow enzyme, T4 DNA polymerase, T4 DNA ligase and deoxynucleotides were obtained from Boehringer Mannheim and were used according to the instructions of the supplier. *E. coli* and *L. lactis* were transformed by electroporation, using a GENE PULSER™ (Bio-Rad Laboratories, Richmond, Calif.), as described by Zabarovsky and Winberg (10) and Holo and Nes (5) with the modifications suggested by Leenhouts and Venema (11), respectively. Plasmid DNA isolation of *L. lactis* was performed as described by Leenhouts and Venema (11) with some modifications. *L. lactis* was grown on ½*M17 without DL-threonine and the incubation in solution A (without mutanolysin) was done at 55° C. for 15 minutes.

Plasmid Constructions.

Figures 14A, 14B:
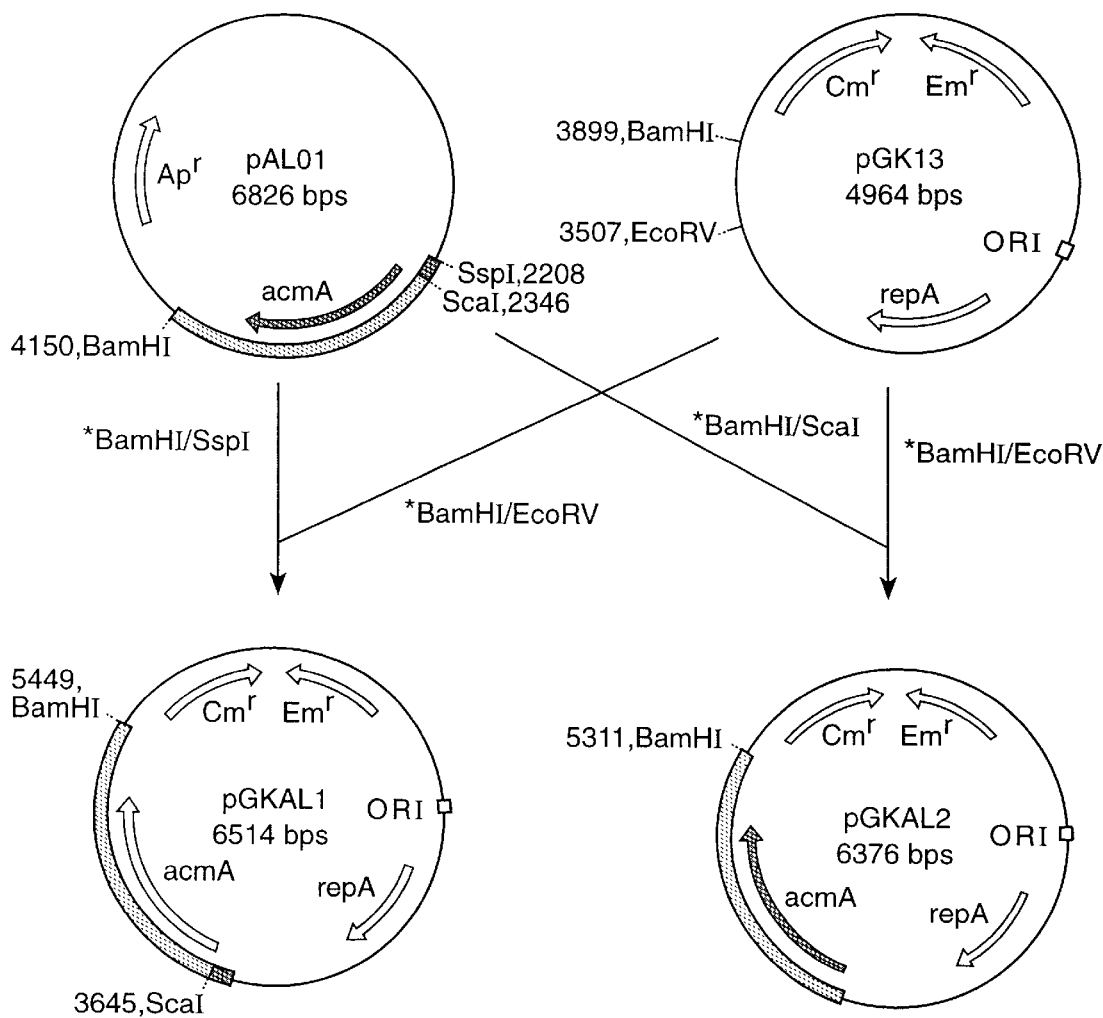
FIGS. 14A and B.(A) Nucleotide sequence (SEQ ID NO:5) of the promoter region of acmA. Putative ribosome binding site (rbs and lower case), −10 and −35 sequences (shaded), startcodon (bold face), and the SspI and ScaI restriction enzyme sites are indicated. (B) Subcloning of acmA, with (pGKAL1) and without (pGKAL2) its own promoter, in pGK13. Ap$^r$, ampicillin resistance gene; EM$^r$, erythromycin resistance gene; Cm$^r$, chloramphenicol resistance gene; ORI(open square), origin of replication of the lactococcal plasmid pWV01; repA, gene encoding the replication protein of plasmid pWV01; acmA, N-acetylmuramidase gene of *L. lactis* subsp. *lactis* MG1363. The ScaI/BamHI fragment containing the acmA gene is dotted and the SspI/ScaI fragment containing the acmA promoter is shown in black. Only relevant restriction enzyme sites are shown.
Figure 15:
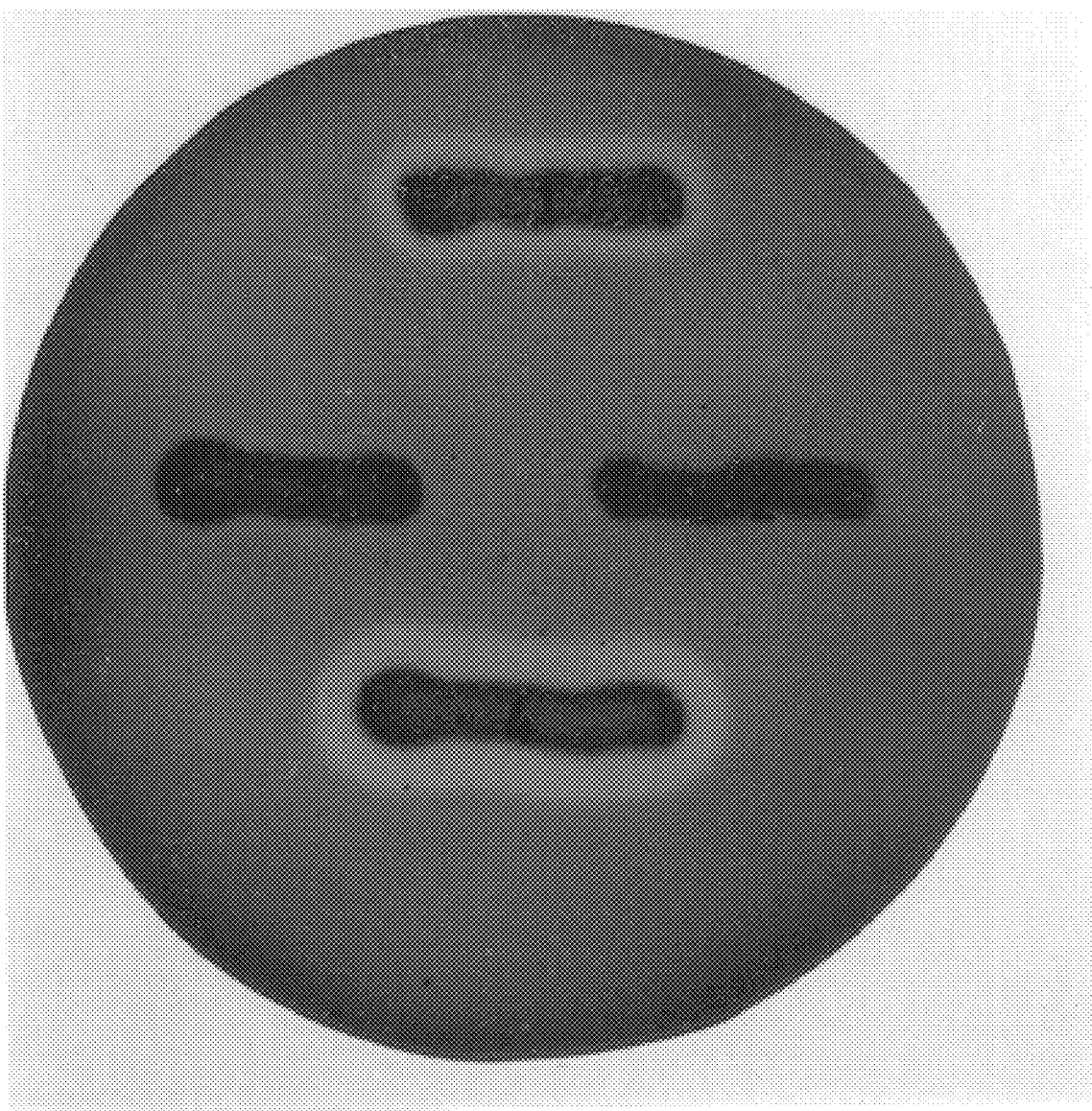
FIG. 15. Analysis of halo formation of *L. lactis* MG1363 containing pGK13 (1), *L. lactis* MG1363acmAΔ1 containing pGK13 (2), pAL2 (3), or pGKAL1 (4) on a GM17 plate containing *M. lysodeikticus* autoclaved cells.

The plasmids pGKAL1 and pGKAL2 were constructed by subcloning of the 1942-bp SspI/BamHI and the 1804-bp ScaI/BamHI fragments of pAL01, respectively, into the EcoRV/BamHI sites of the lactococcal plasmid pGK13 (FIG. 14B). The ligation mixtures and pGK13 were transformed to *L. lactis* MG1363acmAΔ1.

Figure 16:
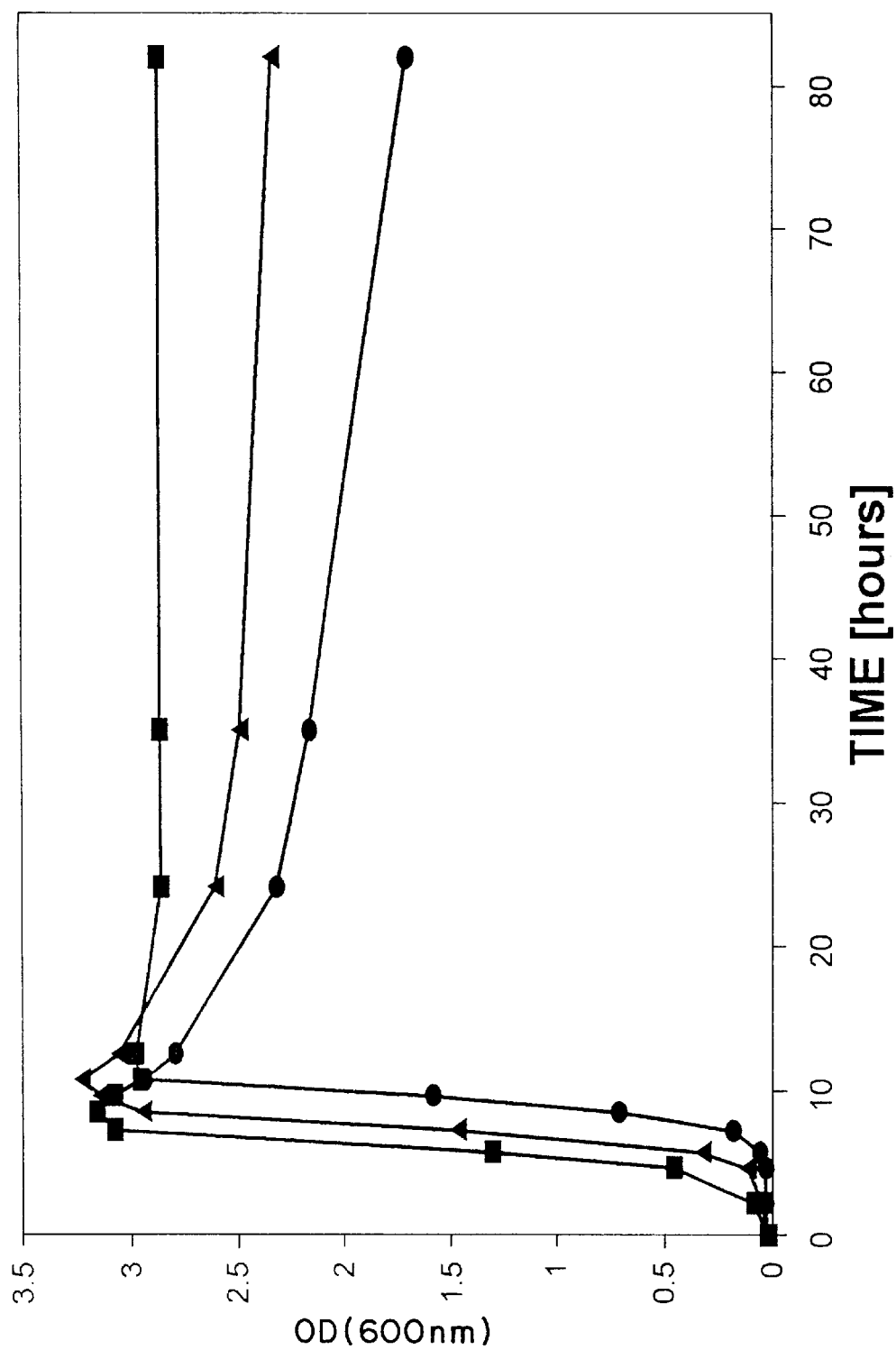
FIG. 16. Analysis of reduction of the optical density measured at 600 nm of *L. lactis* MG1363 containing pGK13 (▲) and *L. lactis* MG1363acmAΔ1 containing pGK13 (■) or pGKAL1 (●).

The construction of pAL12, in which acmA expression is inducible, is schematically presented in FIG. 16. All steps were performed in *E. coli* MC1000 unless stated otherwise. pAL01 is a pUC19 derivative containing a 4137-bp chromosomal DNA fragment from *L. lactis* MG1363 carrying the autolysin gene (acmA). The SacI site present in the multiple cloning site of pAL01 was removed by cutting with EcoRI and SmaI. The plasmid was treated with Klenow enzyme, ligated, and used to electrotransform *E. coli* NM522, resulting in plasmid pAL08. Because *E. coli* grows very poorly when it carries an intact acmA gene (2), acmA was disrupted by cloning into the unique SacI site of pAL08 a 2716-bp SacI fragment originating from the first ORF of the srfA operon of *Bacillus subtilis* (27). This resulted in PAL10.

Plasmid pIR12 contains a segment of DNA of the temperate lactococcal bacteriophage R1-t encompassing the repressor gene (rro), the promoter/operator of rro, tec, the topological equivalent of the *E. coli* lambda cro gene, and ORF29. Expression from the promoter/operator region is induced upon addition of mitomycin C to pIR12-containing cells (14). One unique SacI site present in pIR12 were deleted by replacing the 2750-bp SalI/XhoII fragment by the 1785-bp SalI/BamHI fragment, originating from phage R1-t, of pEF+ (28). The second SacI site in the resulting plasmid, pIR12EF, was removed by digestion with SacI and treatment with T4 DNA polymerase. After self-ligation, pIR1EF was obtained. The 1764-bp EcoRV/XhoII fragment of pIR1EF was replaced by the the 4520-bp ScaI/BamHI fragment of pAL10 containing the interrupted acmA gene. The resulting plasmid, pAL11, was digested with SacI to remove the fragment interrupting acmA. After self-ligation the mixture was used to transform *L. lactis* LL302 and plasmid pAL12 was obtained.

Mitomycin C Induction.

An overnight culture of *L. lactis* was diluted 100-fold in GM17 and grown to an optical density at 600 nm of 0.2. The culture was divided into two portions, to one of which mitomycin C (Sigma) was added to a final concentration of 1 μg/ml, and incubation was continued at 30° C. Optical densities were measured in a Philips PU8720 UW/VIS scanning spectrophotometer (Pye Unicam Ltd. Cambridge, UK) at 600 nm.

SDS-Polyacrylamide Gel Electrophoresis (SDS-PAGE).

For the analysis of in trans action of AcmA two milliliters of culture were subjected to centrifugation. One milliliter of the supernatant fraction was dialysed against several changes of demineralized water, lyophilized, and dissolved in 0.5 ml denaturation buffer (1). The cell pellet was resuspended in 1 ml denaturation buffer and cell-free extracts were prepared as described by van de Guchte et.al. (26). The samples were boiled for 2 min and centrifuged before loading. 30 μl of the mid-exponentional phase samples and 15 μl of the other samples were loaded.

For the analysis of induced lysis one milliliter of sample was treated as described above and the supernatant- and cell fractions were dissolved in 0.2 μl denaturation buffer. The amount of sample loaded was equalized according to the measured optical density. SDS-PAGE was carried out according to Laemmli (8) with the PROTEAN II Minigel System (Bio-Rad). The low range and prestained low and high range SDS-PAGE standards obtained from Bio-Rad were used.

Detection of Lytic Activitiy in SDS-PAA Gels.

Lytic activity was detected in situ by using 12.5% (wt/vol) SDS-PAA gels containing 0.15% (wt/vol) autoclaved, lyophilized M. lysodetkticus ATCC 4698 cells (Sigma). After electrophoresis, the gel was gently shaken at room temperature for 14 h in 200 ml 25 mM Tris-HCl (pH 7) containing 1% (vol/vol) TRITON X-100 to allow protein renaturation (17). Bands of lytic activity were visualised by staining with 1% (wt/vol) Methylene Blue (Sigma) in 0.01% (wt/vol) KOH and destaining with demineralized water (6). SDS-PAA gels without cell walls were stained with Coomassie Brilliant Blue (Bio-Rad).

Western Blotting and Immunodetection

After SDS-PAGE the proteins were transferred to BA85 nitrocellulose membranes (Schleicher and Schull, Dassel, Germany) as described by Towbin et al. (23). Endopeptidase antigen and tripeptidase antigen were detected with polyclonal antiendopeptidase antibodies (12), diluted 1:8000, and polyclonal antitripeptidase antibodies (20), diluted 1:4000, respectively, and alkaline phosphatase-conjugated goat anti-rabbit antibodies (Promega Corporation, Madison, Wis.) using the Western-Light Chemiluminescent detection system of TROPIX (TROPIX, Inc., Bedford, Mass.) according to the manufacturer's instructions.

RESULTS

AcmA is Involved in Autolysis of L. lactis During Stationary Phase.

Figure 13:
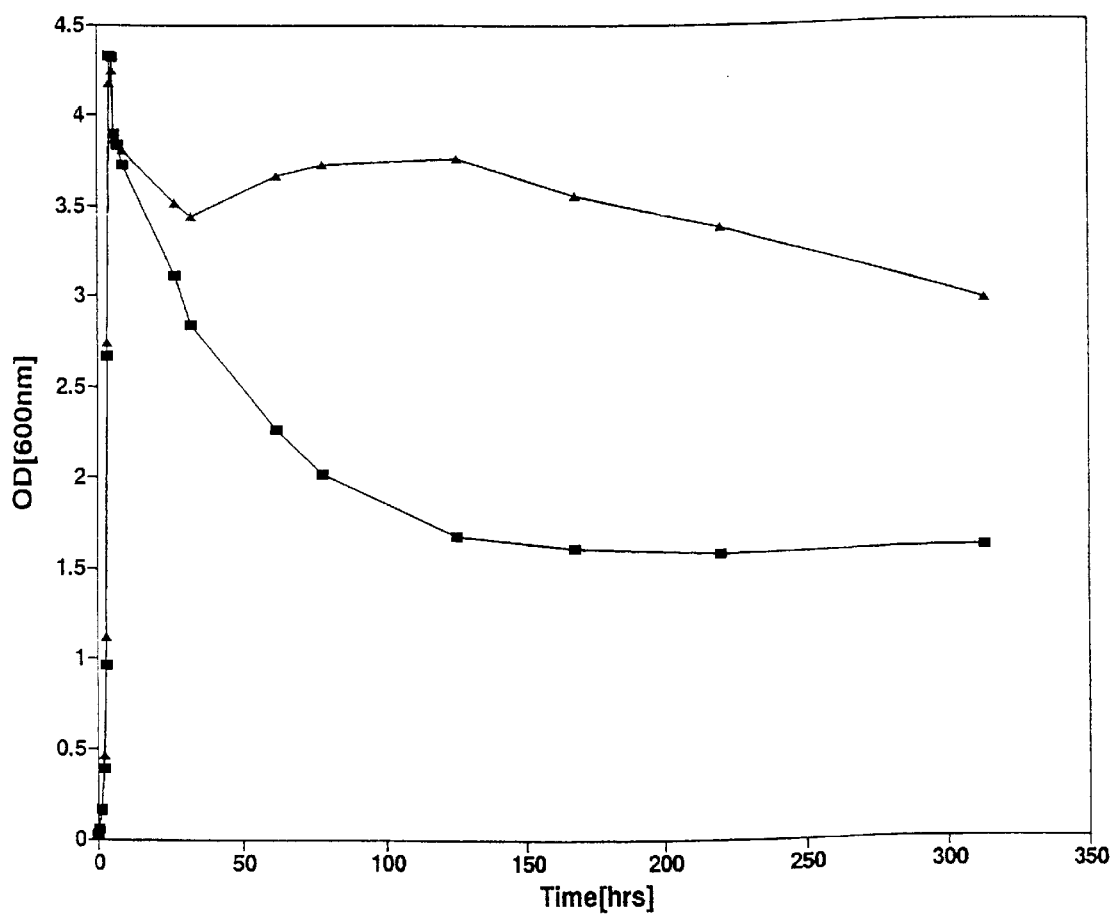
FIG. 13. Growth measured by reading optical density readings at 600 nm of *L. lactis* subsp. *cremoris* strains MG1363 (□) and MG1363acmAΔ1 (▲).

Overnight cultures of L. lactis MG1363 and its acmA deletion mutant MG1363acmAΔ1 (2) were diluted 200-fold in fresh prewarmed M17. During the first 9 hours of growth and hourly sampling, the cultures were gently shaken at 30° C. to prevent settling of MG1363acmAΔ1, which grows as long filaments due to improper cell separation (2). During further incubation, without shaking, samples were taken with larger intervals. FIG. 13 shows the changes in $OD_{600}$ of MG1363 and MG1363acmAΔ1 during 320 hours of incubation. Whereas the wild-type and mutant cells grew equally well, the decrease in $OD_{600}$ of the mutant was much less pronounced than that of the wild-type strain. Apparently. the major autolysin is not only required for cell separation (2), but is also responsible for cell lysis upon prolonged incubation.

Complementation of the acmA Deletion, and Localisation of the acmA Promoter.

To examine wether the 138-bp SspI/ScaI fragment containing a putative −35 and −10 sequence upstream of the startcodon of the acmA gene, was the promoter of this gene, pGKAL1 and pGKAL2 were constructed (FIG. 14B). pGKAL1 contains this putative promoter fragment whereas pGKAL2 lacks this sequence. Strain L. lactis MG1363 containing pGK13 and strain L. lactis MG1363acmAΔ1 containing pGK13, pGKAL1 or pGKAL2 were plated on GM17 plates containing 0.2% Micrococcus lysodeikticus autoclaved cells and incubated for 36 hours at 30° C. The results are presented in FIG. 3 and shows that no halo was obseved around the cells containing pGKAL2, but that a large halo was present around the cells containing pGKAL1. The halo was even larger than the one formed by L. lactis MG1363. This result indicates that the 138-bp SspI-ScaI fragment is required for acmA expression, most likely because it contains the −35 and −10 promoter-specific sequences shaded in FIG. 14A (corresponding to Sequence id no 5).

Increasing the Copy Number of acmA Results in More Autolysis.

Overnight cultures of strains MG1363 containing pGK13 and MG1363acmAΔ1 containing the plasmids pGK13 or pGKAL1 were diluted 100-fold in fresh medium. During the exponentional growth phase the strains grew equally fast (see FIG. 16). In the following 70 hours of incubation, the reduction in optical density of MG1363acmAΔ1 (pGKAL1) was much higher than that of MG1363 (pGK13). As expected during the same period of growth nearly no reduction in $OD_{600}$ was observed with the deletion mutant containing pGK13.

Secreted AcmA Can Act in Trans.

Figure 17:
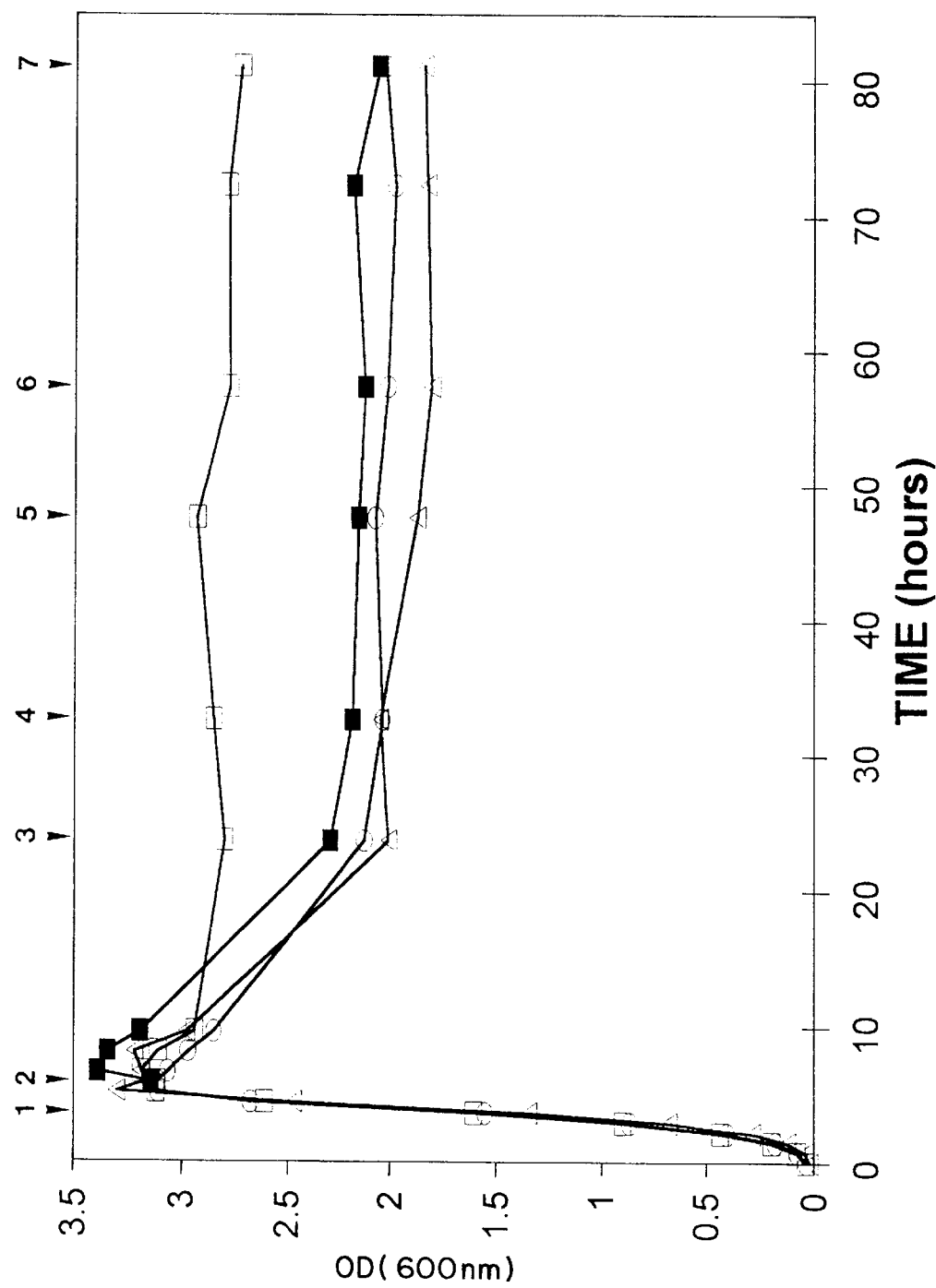
FIG. 17. Analysis of reduction of the optical density measured at 600 nm of *L. lactis* MG1363 (○), *L. lactis* MG1363pepT (Δ), *L. lactis* MG1363acmAΔ1 (□) and an end-exponentional phase mixed culture of *L. lactis* MG1363pepT and *L. lactis* MG1363acmAΔ1 (■). The numbers on top of the graph indicate the time points at which samples were taken from the cultures.

Overnight cultures of MG1363acmAΔ1 and MG1363pepT were diluted 100-fold in fresh medium. At the end of the exponentional phase of growth equal fractions of both strains were mixed and incubated at 30° C. The optical density was followed for 70 hours and samples were taken at various time points to analyze AcmA activity, the presence of PepT, and the release into the culture medium of intracellular proteins. The reduction of $OD_{600}$ during prolonged stationary phase of the mixed culture is nearly equal to that of the cultures of MG1363 and the pepT deletion mutant (see FIG. 17), indicating that the degree of autolysis is nearly the same in these three cultures. Also the average chainlenght in the mixed culture was equal to that of the lenght of the chains of MG1363 and MG1363pepT. FIGS. 18 (A,B,C) and Table 3 show the analysis of AcmA activity and the presence of PepT in the cell and supernatant fractions while the release of intracellular proteins into the culture medium is presented in FIG. 18B. From these results it can be concluded that in the control strain MG1363 AcmA is produced, secreted and causes autolysis of cells from the moment the culture enters the stationary growth phase. Autolysis results in the release of intracellular proteins into the culture medium, see FIG. 18B, of which one, PepT, was visualized using specific antibodies (see FIG. 18C). Also in MG1363pepT autolysis and subsequent release of intracellular proteins occurs, as expected no PepT was detected in the supernatant fraction. MG1363acmAΔ1 produces PepT but no autolysis occurs and, therefore, no PepT or other intracellular proteins are released (FIG. 18B and 18C).

Induced Expression of AcmA.

To examine whether overexpression of AcmA would lead to cell lysis, the acmA gene lacking its native promoter but retaining its own RBS (2) was cloned in pIR12 (15), resulting in plasmid pAL12 (FIG. 19). pAL12 contains rro, tec, and the promoter/operator of the repressor protein Rro of the L. lactis subsp. cremoris bacteriophage R1-t. The expression of genes cloned downstream of tec is repressed by the Rro repressor (15) but is induced upon addition of mitomycin C. Plasmid pAL12 was transformed to L. lactis subsp. cremoris LL302 which contains a copy of the pWV01 repA gene on the chromosome to ensure efficient replication. Mitomycin C (1 μg/ml) was added to L. lactis MG1363 containing pGK13 and L. lactis LL302 containing pIR12, pAL12, or pIR1PR, in which β-galactosidase, AcmA, and LytP and LytR are expressed, respectively. With intervals of one hour the optical density at 600 nm was measured. The results are presented in FIG. 20 and show that, starting at approximately 2 to 3 hours after the addition of mitomycin C, the optical density of strain LL302(pAL12) gradually and steadily decreased. The strain carrying the bacteriophage R1-t lysis cassette LytP/LytR also showed a distinct reduction in $OD_{600}$ upon addition of mitomycin C, as shown by Nauta et al. (14). In contrast. strain MG1363(pGK13) and LL302(pIR12), which produces *E. coli* β-galactosidase from the same promoter/operator cassette, did not show detectable lysis in this assay. The data presented in FIG. 20 clearly shows that addition of 1 μg/ml of mitomycin C resulted in a severe inhibition of growth of the cells. Taken together, the results presented in FIG. 16 strongly suggest that overproduction of AcmA by the addition of mitomycin C to exponentially growing *L. lactis* LL302(pAL12) causes lysis of the cells.

Figure 21:
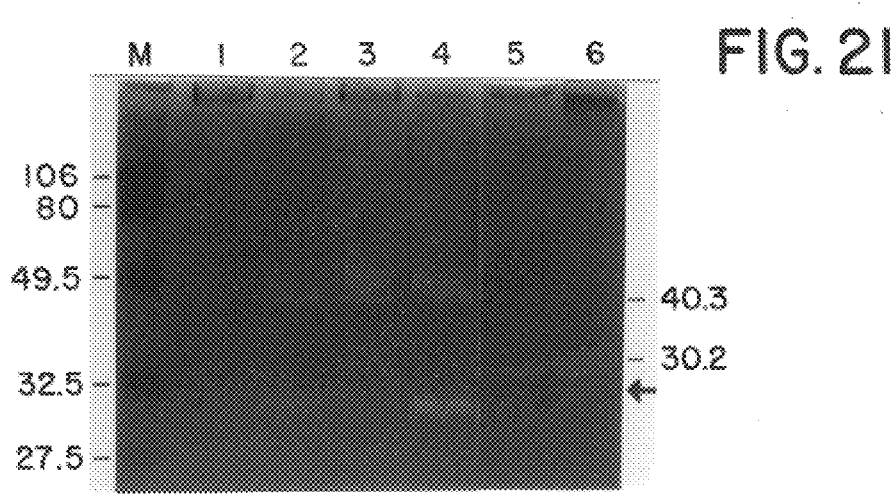
FIG. 21. Renaturing SDS-PAGE analysis of the autolysin activity of *L. lactis* LL302 containing pIR12 (lanes 1,2), pIR1PR (lanes 5,6) or pAL12 (lanes 3,4). Samples of 1 ml were taken four hours after the addition of mitomycin C to exponentially growing cells (see FIG. 15). Cell-free extracts (1,3,5) and supernatant fractions (2,4,6) were loaded on PAA gels containing 0.2% (wt/vol) *M. lysodeikticus* autoclaved cells. Molecular masses of standard proteins (M) are shown on the left and on the right the clearing bands due to AcmA (40.3) and LytR (30.2) activity are shown (all in kilodaltons (kDa). A clearing band caused by a degradation product of AcmA is indicated with an arrow (←).

To examine whether under the conditions employed, production of AcmA was indeed induced, samples were taken four hours after mitomycin C addition and inspected by renaturing SDS-PAGE for lytic activity in the cell-free and supernatant fractions. The results are presented in FIG. 21 and show that increased activity of AcmA was present in an *L. lactis* LL302(pAL12) cell-free extract as compared to cell-free extracts of *L. Lactis* LL302(pIR12) and *L. lactis* LL302(pIR1PR). Qualitatively, the same applied to the supernatant fractions of the three strains: only *L. lactis* LL302(pAL12) produced an excess of a clearing band at a position corresponding to a protein of 30 kDa, which has been shown to be an active degradation product of AcmA (2). Both in the cell-free extract and the supernatant of strain LL302(pIR1PR) the phage lysin specified by pIR1PR was present, together with the lytically active breakdown products of AcmA produced from the chromosome of the strain. We conclude from these data that the synthesis of AcmA was increased upon induction with mitomycin C.

Cytoplasmic Proteins are Released in the Culture Medium Upon Induction of AcmA Overexpression.

Figure 19:
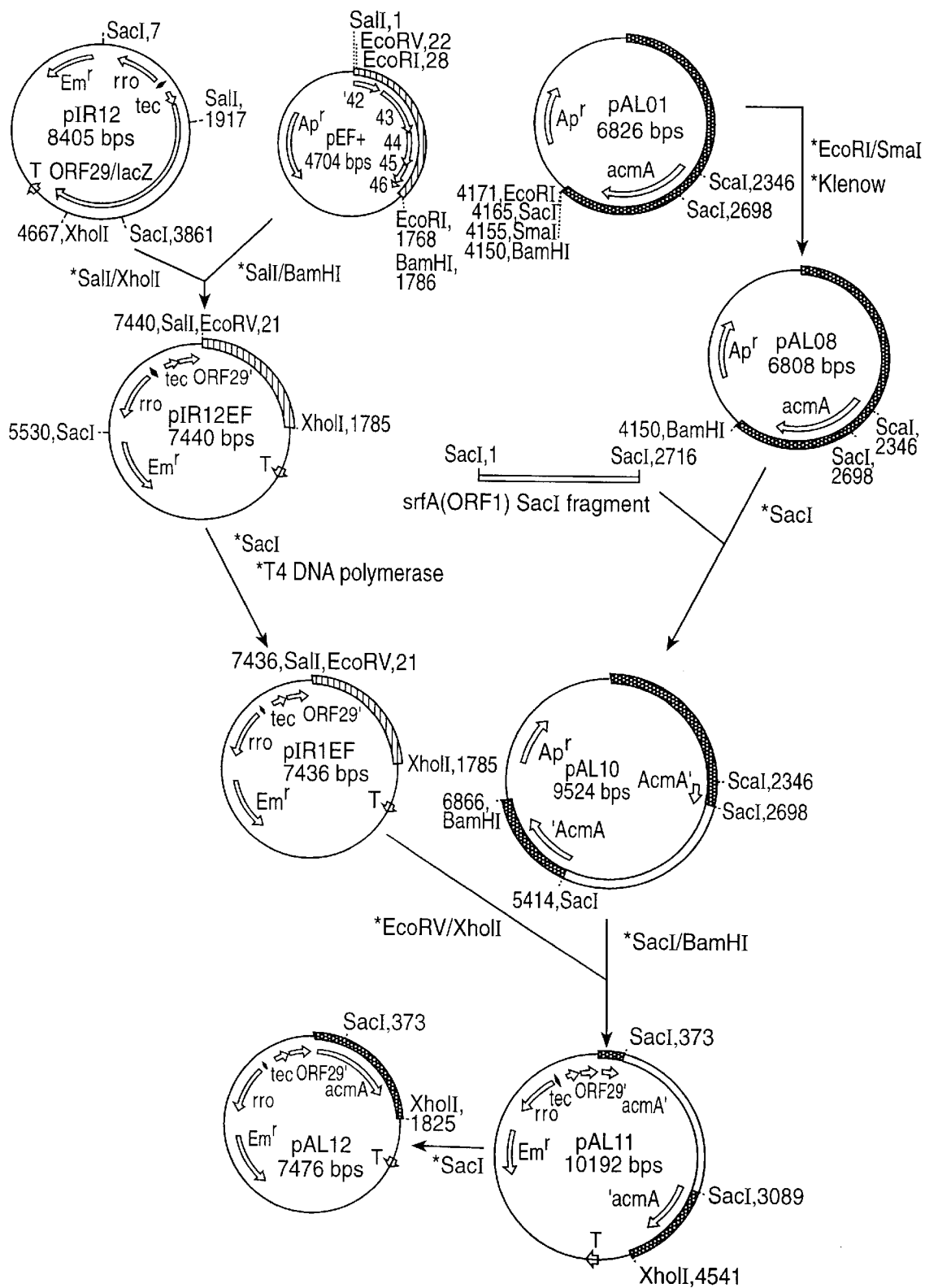
FIG. 19. Cloning scheme for the construction of pAL12, in which AcmA production is inducible. ◀▶, promoters from bacteriophage R1-t; Em$^r$, erythromycin resistance gene; Ap$^r$, ampicillin resistance gene; lacZ, β-galactosidase gene of *E. coli*; T, transcription terminator of prtP; rro, R1-t repressor gene; tec, topological equivalent of lambda cro; ORF29', N-terminal part of ORF29 of phage R1-t; ORF29/ lacZ, transcriptional fusion of ORF29 and lacZ; SacI fragment, a 2716-bp SacI fragment of ORF1 of the srfA locus of *Bacillus subtilis*; acmA, N-acetylmuramidase gene of *L. lactis*; 42',43,44,45,46', indicating the ORF's of phage RI-t which are located on the EcoRI fragment ofpEF+. Only relevant restriction enzyme sites are shown.
Figure 20:
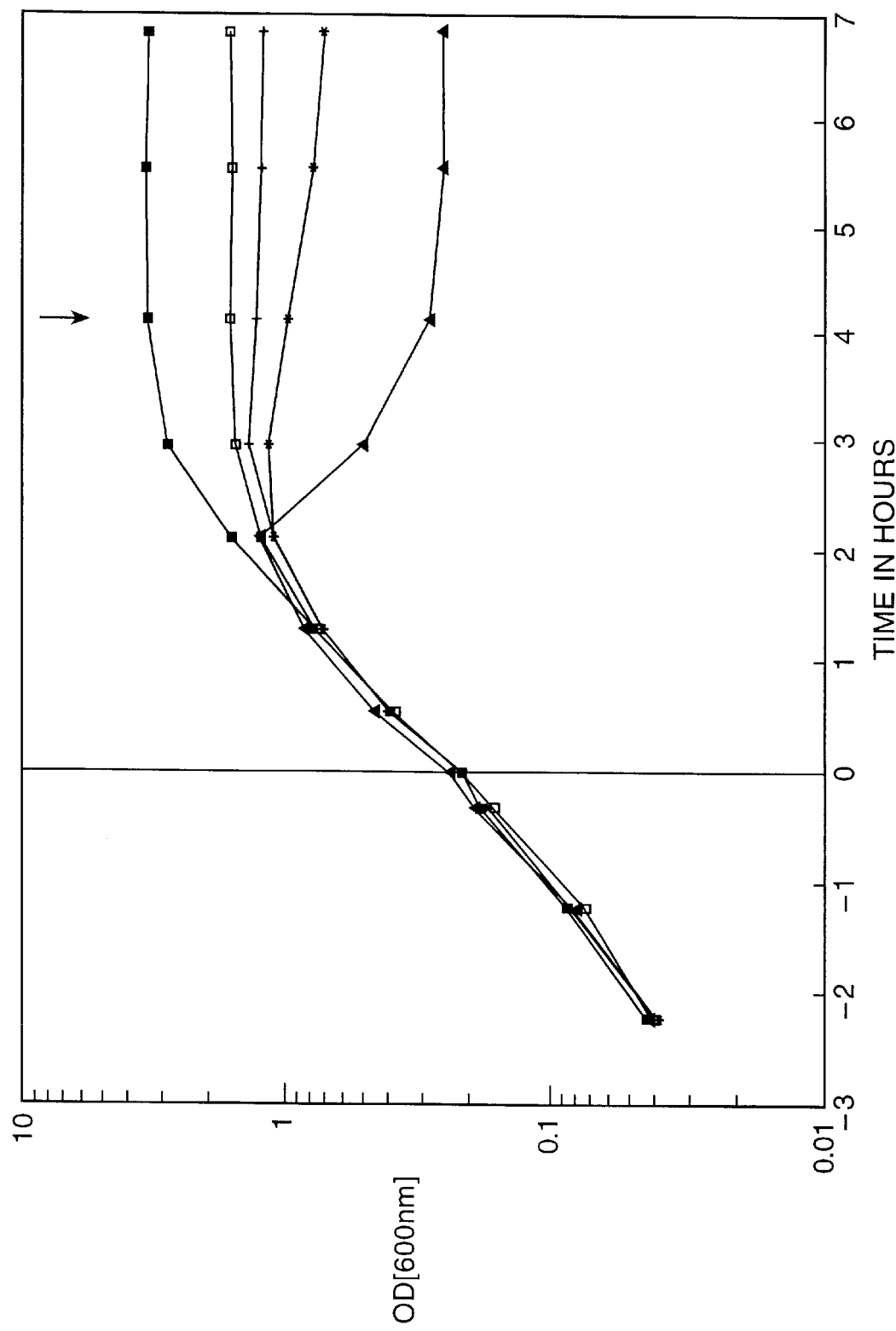
FIG. 20. Effect of mitomycin C on $OD_{600}$ of *L. lactis* MG1363 containing pGK13 (□) and *L. lactis* LL302 strains containing pIR12 (+), pIR1PR (▲) and pAL12 (*). The culture of *L. lactis* LL302 cotaining pAL12 (■) was not induced. The cultures were induced with 1 μg/ml mitomycin C at time zero (dotted line). The arrow (↓) indicates the time at which 1 ml samples were taken and processed for the analysis of AcmA activity (FIG. 21) and protein and peptidase analysis (FIGS. 22 and 23, respectively).
Figure 22:
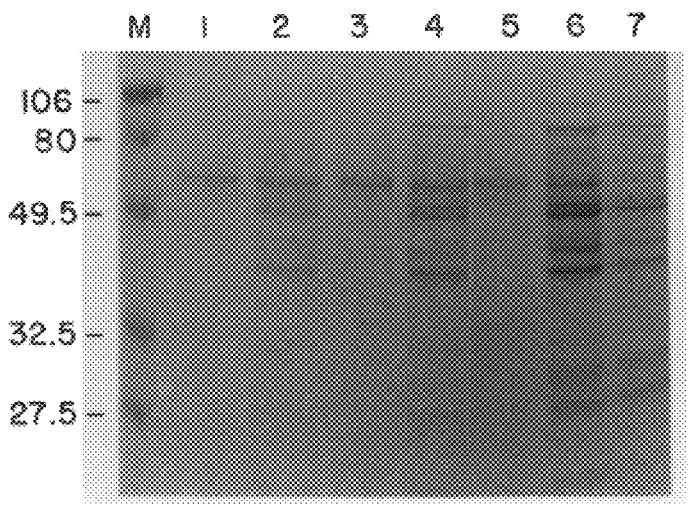
FIG. 22. Liberation of proteins in the culture supernatant of induced (lanes 2,4,6) and non-induced (lanes 1,3,5) *L. lactis* LL302 containing pIR12 (1,2). pAL12 (3,4). or pIR1PR (5.6). Lane 9: cell-free extract of non-induced *L. lactis* LL302(pIR12). Molecular masses (in kDa) of standard proteins (M) are shown on the left.
Figure 23:
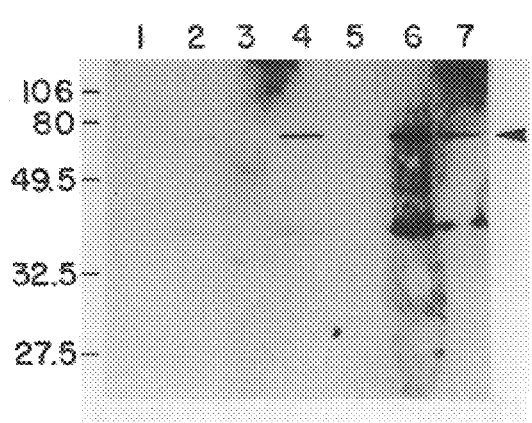
FIG. 23. Western blot analysis of the gel shown in FIG. 22 using polyclonal antibodies raised against the lactococcal endopeptidase PepO. The arrowhead indicates the position of the endopeptidase. The order of the samples is identical to the order in FIG. 22.

Although AcmA production was clearly induced, the OD measurements did not conclusively show that increased production of the autolysin resulted in lysis of the host cells. To examine this in a more direct way, the supernatant fractions of induced cultures were assayed for the presence of intracellular proteins by SDS-PAGE. The results, presented in FIG. 22, show that in uninduced cultures only one protein is present. Most probably, this protein is the previously described Usp45 (25). Upon induction, proteins normally present in the cell-free extracts only, are extruded into the culture medium, especially in *L. lactis*(pIR1PR), overexpressing the bacteriophage lysis cassette LytP/LytR (FIG. 19 lane 6). To a considerable extent this also applies to *L. lactis*(pAL12), overexpressing acmA (FIG. 22, lane 4). To a lesser extent, *L. lactis*(pIR12) extruded proteins into the supernatant, indicating that, as has been observed before (14), the presence of mitomycin C and/or the overproduction of high amounts of β-galactosidase, caused some lysis. To ascertain that cytoplasmic proteins were extruded into the culture medium after mitomycin C induction, immunoblots were performed on supernatants of cells carrying the various plasmids. The results in FIG. 20 show that antibodies raised against the cy oplasmic lactococcal peptidase PepO (13) gave a strong signal with the supernatant of *L. lactis*(pAL12) and only a weak one with that fraction of *L. lactis*(pIR12).

DISCUSSION

The observation that nearly no cell lysis was observed in a culture of the *Lactococcus lactis* MG1363acmAΔ1 during prolonged stationary growth, indicates that AcmA, is, in addition to cell separation (2), also responsible for autolysis. This result also shows that no other major autolysin activity, resulting in autolysis, is present in *L. lactis* MG1363. No halo could be detected, not even after one week of incubation at 30° C. (result not shown), when *L. lactis* MG1363acmAΔ1 was plated on a GM17 plate containing *Micrococcus lysodeikticus* cell walls as a substrate, showing that no other major autolysin is present. In contrast, when this mutant strain contained plasmid pGKAL1 a large halo was produced, but no halo was formed when it contained pGKAL2. This result shows that the acmA promoter is located within the 138-bp SspI-ScaI fragment upstream of acmA. When the mutant strain contained pGKAL1 this led to a higher reduction of the optical density as compared to the wildtype strain, indicating that a higher expression of AcmA, because of the presence of more copies of the gene in this strain, results in more cell lysis.

The acmA gene, lacking its own promoter, downstream of the promoter/operator region of the temperate lactococcal bacteriophage RI-t was subcloned. In this plasmid the expression of acmA was inducible upon addition of mitomycin C, which was shown in a denaturing SDS-PAA gel containing *M. lysodeikticus* cell-walls as a substrate. Four hours after induction increased expression of AcmA was observed in the lactococcal strain containing pAL12 while a natural level of expression was found in the strain containing either pGK13, pIR12, or pIR1PR. Growth analysis of these strain showed that the overproduction of AcmA leads to a cell lysis. Although limited lysis of cells was observed in the strain overexpressing β-galactosidase, which might be due to the high level of mytomicin C used, a higher level of reduction of the optical density was observed in cultures of the strain overexpressing AcmA. Cells containing pIR1PR lysed more readily upon induction than cells containing pAL12 (FIG. 20). Although other conclusions cannot be excluded, this difference may be caused by a higher lytic activity of LytR than that of AcmA. From the growth analyses it is clear that mitomycin C inhibits the growth of cells. To circumvent this undesirable side effect of this DNA-damaging substance, research was focussed on the isolation of a temperature sensitive repressor (Rro) mutation, so that the system can be made temperature-inducible. The promoter is present on plasmid pIR14 deposited at the Centraal Bureau voor Schimmelcultures in Baarn, The Netherlands in accordance with the Budapest Treaty on May 11, 1995 with accession number CBS 327.95. Release of the intracellularly located lactococcal endopeptidase, which might well be involved in flavour development during cheese maturation, was demonstrated using antibodies against this protein. Strong signals were found in samples of the culture supernatant of the two strains that lysed upon induction, viz. LL302(pIR1PR) and LL302(pAL12).

In trans action of AcmA was shown by analysing a mixed culture of acmA and pepT minus cells during prolonged incubation in stationary phase. Release of PepT, expressed by acmA minus cells, into the culture medium was shown to occur as a result of the expression and secretion of AcmA by pepT minus cells.

From these data we conclude that we have succeeded in the development of a system in which the expression of the major autolysin AcmA of *L. Lactis* was made inducible, and that the production of AcmA leads to lysis of *L. lactis* with concomitant release of intracellular proteins and enzymes in the culture medium.

TABLE 2

Bacterial strains and plasmids

| Strain or plasmid | Relevant phenotype or genotype | Source or reference |
|---|---|---|
| Strains | | |
| *L. lactis* subsp. cremoris | | |
| MG1363 | Plasmid-free strain | (4) |
| MG1363acmAΔ1 | MG1363 derivative containing a 701 bp SacI/SpI chromosomal deletion in the acmA gene | (2) |
| MG1363pepT | MG1363 derivative containing a deletion in the pepT gene | (12) |
| LL302 | MG1363 carrying the pWV01 repA gene on the chromosome | Culture Collection RU Groningen |
| *E. coli* | | |
| NM522 | supE, thi, Δ(lac-proAB), Δhsd5(r-, m-) [F', proAB, lacI$^q$ZM15] | Stratagene (La Jolla, CA.) |
| MC1000 | araD139, lacx74, (ara, leu)7697, galU, galK, strA | (3) |
| Plasmids | | |
| pAL01 | Ap$^r$, pUC19 carrying a 4137 bp lactococcal chromosomal DNA insert with the peptidoglycan hydrolase gene acmA | (2) |
| pAL08 | Ap$^r$, pAL01 with a SmaI/EcoRI deletion | (2) |
| pAL10 | Ap$^r$, pAL08 containing a 2716-bp SacI fragment of ORF1 of the srfA operon of *B. subtilis*. | This work |
| pAL11 | Em$^r$, SK+ with a 710 bp SacI/SpeI fragment of pAL03 | This work |
| pAL12 | Em$^r$, SK+ with a 477 bp ScaI/ClaI fragment of pAL04 | This work |
| pIR12 | Em$^r$, carrying the regulatory region of phage R1-t | (15) |
| pEF+ | Ap$^r$, SK+ containing a 1740-bp EcoRI fragment of phage R1 | Plasmid Collection RU Groningen |
| pIR12EF | Em$^r$, pIR12 containing a 1785-bp SalI/BamHI fragment of pEF+ | This work |
| pIR1EF | Em$^r$, pIR12EF with a deleted SacI site | This work |
| pIR1PR | Em$^r$, pIR12 derivative carrying the lytP and lytR gene of R1-t | (14) |
| pGK13 | Em$^r$, Cm$^r$, pWV01 based lactococcal plasmid. | (7) |
| pGKAL1 | Em$^r$, Cm$^r$, pGK13 containing the 1942 bp SspI/BamHI fragment of PAL01 | This work |
| pGKAL2 | Em$^r$, Cm$^r$, pGK13 containing the 1804 bp ScaIBamHI fragment od pAL01 | This work |

List of References
1. WO 90/00599 (AGRICULTURAL & FOOD RESEARCH COUNCIL; M. J. Gasson) published Jan. 25, 1990; Uses of viral enzymes
2. C. A. Shearman, K. Jury & M. J. Gasson (AFRC); Biotechnology 10 (Febuary 1992) 196–199; Autolytic *Lactococcus lactis* expressing a lactococcal bacteriophage lysin gene
3. C. Platteeuw and W. M. de Vos (NIZO); Gene 118 (1992) 115–120; Location, characterization and expression of lytic enzyme-encoding gene, lytA, of *Lactococcus lactis* bacteriophage φUS3
4. R. Young; Microbiol. Reviews 56 (1992) 430–481; Bacteriophage Lysis: Mechanism and Regulation; esp. pages 468–472: Lysis in Phage Infections of Gram-Positive Hosts, and Perspectives
5. C. Shearman, H. Underwood, K. Jury, and M. Gasson (AFRC); Mol. Gen. Genet. 218 (1989) 214–221; Cloning and DNA sequence analysis of a Lactococcus bacteriophage lysin gene
6. L. J. H. Ward, T. P. J. Beresford, M. W. Lubbers, B. D. W. Jarvis and A. W. Jarvis; Can. J. Microbiol. 39 (1993) 767–774; Sequence analysis of the lysin gene region of the prolate lactococcal bacteriophage c2
7. EP-A2-0 510 907 (AGRICULTURAL & FOOD RESEARCH COUNCIL; M. J. Gasson) published Oct. 28, 1992; Bacteriophage lysins and their applications in destroying and testing for bacteria Literature References of Draft Publication 1

1. Bailey, M. J. A., V. Koronakis, T. Schmoll, and C. Hughes. 1992. *Escherichia coli* HlyT protein, a transcriptional activator of haemolysin synthesis and secretion, is encoded by the rfaH(sfrB) locus required for expression of sex factor and lipopolysaccharide genes. Mol. Microbiol. 6:1003–1012.
2. Beliveau, C., C. Potvin, J. Trudel, A. Asselin, and G. Bellemare. 1991. Cloning, sequencing and expression in *Escherichia coli* of a *Streptococcus faecalis* autolysin. J. Bacteriol. 173:5619–5623.
3. Chiaruttini, C. and M. Milet. 1993. Gene organization, primary structure and RNA processing analysis of a ribosomal RNA operon in *Lactococcus lactis*. J. Mol. Biol 230:57–76.
4. Chomczynski, P. and P. K. Quasba. 1984. Alkaline transfer of DNA to plastic membrane. Biochem. Biophys. Res. Commun. 122:340–344.
5. Chopin, A., M. -C. Chopin, A. Moillo-Batt, and P. Langella. 1984. Two plasmid-determined restriction and modification systems in *Streptococcus lactis*. Plasmid 11:260–263.
6. Chu, C. -P., R. Kariyama, L. Daneo-Moore, and G. D. Shockman. 1992. Cloning and sequence analysis of the muramidase-2 gene from *Enterococcus hirae*. J. Bacteriol. 174:1619–1625.
7. Daniels, D. L., G. Plunkett III, V. Burland, and F. R. Blattner. 1992. Analysis of the *Escherichia coli* genome: DNA sequence of the region from 84.5 to 86.5 minutes. Science 257:771–778.
8. de VOS, W. M. and G. F. M. Simons. 1993. Gene cloning and expression systems in lactococci, p. 52–105. In M. J. Gasson and W. M. de Vos (eds.), Genetics and Biotechnology of Lactic Acid Bacteria.
9. de VOS, W. M., P. Vos, H. de Haard, and I. Boerrigter. 1989. Cloning and expression of the *Lactococcus lactis* subsp. *cremoris* SK11 gene encoding an extracellular serine proteinase. Gene 85:169–176.
10. Del Mar Lleo, M., P. Canepari, and G. Satta. 1993. Thermosensitive cell growth mutants of *Enterococcus hirae* that elongate at non-permissive temperature are stimulated to divide by parental autolytic enzymes. J. Gen. Microbiol. 139:3099–3107.
11. Doyle, R. J., J. Chaloupka, and V. Vinter. 1988. Turnover of cell walls in microorganisms. Microbiol. Rev. 52:554–567.
12. Exterkate, F. A. 1976. Comparison of strains of *Streptococcus cremoris* for proteolytic activities associated with the cell wall. Neth. Milk Dairy J. 30:95–105.
13. Gasson, M. J. 1983. Plasmid complements of *Streptococcus lactis* NCDO 712 and other lactic Streptococci after protoplast-induced curing. J. Bacteriol. 154:1–9.
14. Hill, C., C. Daly, and G. F. Fitzgerald. 1985. Conjugative transfer of the transposon Tn919 to lactic acid bacteria. FEMS Microbiol. Lett. 30:115–119.
15. Holo, H. and I. F. Nes. 1989. High-frequency transformation, by electroporation, of *Lactococcus lactis* subsp. *cremoris* grown with glycine in osmotically stabilized media. Appl. Environ. Microbiol. 55:3119–3123.
16. Hourdou, M.-L., M. Guinand, M. -J. Vacheron, G. Michel, L. Denoroy, C. Duez, S. Englebert, B. Joris, C. Weber, and J. -M. Ghuysen. 1993. Characterization of the sporulation-related τ-D-glutamyl-(L)meso-diaminopimelic-acid-hydrolysing peptidase I of *Bacillus sphaericus* NCTC 9602 as a member of the metallo(zinc) carboxypeptidase A family (Modular design of the protein). Biochem. J. 292:563–570.
17. Jayaswal, R. K., Y. -I. Lee, and B. J. Wilkinson. 1990. Cloning and expression of a *Staphylococcus aureus* gene encoding a peptidoglycan hydrolase activity. J. Bacteriol. 172:5783–5788.
18. Jolliffe, L. K., R. J. Doyle, and U. N. Streips. 1980. Extracellular proteases modify cell wall turnover in *Bacillus subtilis*. J. Bacteriol. 141:1199–1208.
19. Jones, C. J., M. Homma, and R. M. Macnab. 1989. L-, P-, and M-ring proteins of the flagellar basal body of *Salmonella typhimurlum*: gene sequences and deduced protein sequences. J. Bacteriol. 171:3890–3900.
20. Joris, B., S. Englebert, C. -P. Chu, R. Kariyama, L. Daneo-Moore, G. D. Shockman, and J. -M. Ghuysen. 1992. Modular design of the *Enterococcus hirae* muramidase-2 and *Streptococcus faecalis* autolysin. FEMS Microbiol. Lett. 91:257–264.
21. Kaije, S. -I., R. Ideta, I. Yamato, and Y. Anraku. 1991. Molecular cloning and DNA sequence of dniR a gene affecting anaerobic expression of the *Escherichia coli* hexaheme nitrite reductase. FEMS Microbiol. Lett. 83:205–212.
22. Kuroda, A. and J. Sekiguchi. 1990. Cloning, sequencing and genetic mapping of a *Bacillus subtilis* cell wall hydrolase gene. J. Gen. Microbiol. 136:2209–2216.
23. Kuroda, A. and J. Sekiguchi. 1991. Molecular cloning and sequencing of a major *Bacillus subtilis* autolysin gene. J. Bacteriol. 173:7304–7312.
24. Laemili, U. K. 1970. Cleavage of structural proteins during the assembly of the head of bacteriophage T4. Nature(London) 227:680–685.
25. Langsrud, T., A. Landaas, and H. B. Castberg. 1987. Autolytic properties of different strains of group N streptococci. Milchwissenschaft 42:556–560.
26. Leclerc, D. and A. Asselin. 1989. Detection of bacterial cell wall hydrolases after denaturing polyacrylamide gel electrophoresis. Can. J. Microbiol. 35:749–753.
27. Leenhouts, K. and G. Venema. 1992. Molecular cloning and expression in Lactococcus. Med. Fac. Landbouww. Univ. Gent. 57:2031–2043.
28. Leenhouts, K. J., J. Kok, and G. Venema. 1990. Stability of integrated plasmids in the chromosome of *Lactococcus lactis*. Appl. Environ. Microbiol. 56:2726–2735.
29. Leenhouts, K. J. and G. Venema. 1993. Lactococcal plasmid vectors, p. 65–94. In K. G. Hardy (ed.), Plasmids, a practical approach. Oxford University Press, Oxford.
30. McDonald, I. J. 1971. Filamentous forms of *Streptococcus cremoris* and *Streptococcus lactis*. Observations on structure and susceptibility to lysis. Can. J. Microbiol. 17:897–902.
31. Mou, L., J. J. Sullivan, and G. R. Jago. 1976. Autolysis of *Streptococcus cremoris*. J. Dairy. Res. 43:275–282.
32. Mundt, J. O. 1986. Lactic acid streptococci, p. 1065–1066. In P. H. A. Sneath, N. S. Mair, M. E. Sharpe, and J. G. Holt (eds.), Bergey's manual of systematic bacteriology, vol.2. Williams and Wilkins, Baltimore.
33. Niskasaari, K. 1989. Characteristics of the autolysis of variants of *Lactococcus lactis* subsp. *cremoris*. J. Dairy. Res. 56:639–649.
34. Oda, Y., R. Nakayama, A. Kuroda, and J. Sekiguchi. 1993. Molecular cloning, sequence analysis, and characterization of a new cell wall hydrolase, CwlL, of *Bacillus licheniformis*. Mol. Gen. Genet. 241:380–388.
35. Pearson, W. R. and D. J. Lipman. 1988. Improved tools for biological sequence comparison. Proc. Natl. Sci. USA 85:2444–2448.
36. Platt, T. 1986. Transcription termination and the regulation of gene expression. Ann. Rev. Biochem. 55:339–372.
37. Potvin, C., D. Leclerc, G. Tremblay, A. Asselin, and G. Bellemare. 1988. Cloning, sequencing and expression of a Bacillus bacteriolytic enzyme in *Escherichia coli*. Mol. Gen. Genet. 214:241–248.
38. Rogers, H. J. 1979. The function of bacterial autolysins, p. 237–268. In R. C. W. Berkeley, G. W. Gooday, and D. C. Ellwood (eds.), Microbial polysaccharides and polysaccharidases. Academic Press, Inc.(London),Ltd., London.
39. Sambrook, J., E. F. Fritsch, and T. Maniatis. 1989. Molecular cloning a laboratory manual. Cold Spring Harbor Laboratory Press, Cold Spring Harbor, N.Y.
40. Sanger, F., S. Nicklen, and A. R. Coulson. 1977. DNA sequencing with chain-terminating inhibitors. Proc. Natl. Acad. Sci. USA 74:5463–5467.
41. Seegers, J. F. M. L., S. Bron, C. M. Franke, G. Venema, and R. Kiewit. 1994. The majority of lactococcal plasmids carry a highly related replicon. Microbiol. (in press):
42. Shockman, G. D. 1992. The autolytic ('suicidase') system of *Enterococcus hirae*: From lysine depletion autolysis to biochemical and molecular studies of the two muramidases of *Enterococcus hirae* ATCC9790. FEMS Microbiol. Lett. 100:261–268.
43. Tinoco, jun. I., P. N. Borer, B. Dengler, M. D. Levine, O. C. Uhlenbeck, D. M. Crothers, and J. Gralla. 1973. Improved estimation of secondary structure in ribonucleic acids. Nature New Biol. 246:40–41.
44. Tomasz, A. 1984. Building and breaking of bonds in the cell wall of bacteria-the role for autolysins, p. 3–12. In C. Nombela (ed.), Microbial cell wall synthesis and autolysis. Elsevier Science Publishers, Amsterdam.
45. van de Guchte, M., J. Kodde, J. M. B. M. van der Vossen, J. Kok, and G. Venema. 1990. Heterologous gene expression in *Lactococcus lactis* subsp. *lactis*: synthesis, secretion, and processing of the Bacillus subtilis neutral protease. Appl. Environ. Microbiol. 56:2606–2611.

46. van de Guchte, M., J. Kok, and G. Venema. 1992. Gene expression in *Lactococcus lactis*. FEMS Microbiol. Rev. 88:73–92.
47. Vieira, J. and J. Messing. 1991. New pUC-derived cloning vectors with different selectable markers and DNA replication origins. Gene 100:189–194.
48. Visser, F. M. W. 1977. Contribution of enzymes from rennet, starter bacteria and milk to proteolysis and flavour development in Gouda cheese. 2. Development of bitterness and cheese flavour. Neth. Milk Dairy J. 31:188–209.
49. Von Heijne, G. 1986. A new method for predicting signal peptide cleavage sites. Nucl. Acids Res. 14:4683–4690.
50. Von Heijne, G. and L. Abrahms'n. 1989. Species-specific variation in signal peptide design; Implications for protein secretion in foreign hosts. FEBS Letters 244:439–446.
51. Ward, J. B. and R. Williamson. 1984. Bacterial autolysins: specificity and function. p. 159–175. In C. Nombela (ed.), Microbial cell wall synthesis and autolysis. Elsevier Science Publishers, Amsterdam.
52. Wuenscher, M. D., S. Kbhler, A. Bubert, U. Gerike, and W. Goebel. 1993. The Zap gene of *Listeria monocytogenes* is essential for cell viability, and its gene product, p60, has bacteriolytic activity. J. Bacteriol. 175:3491–3501.
53. Yanish-Perron, C., J. Vieira, and J. Messing. 1985. Improved M13 phage cloning vectors and host strains: nucleotide sequences of the M13mp18 and pUC19 vectors. Gene 33:103–119.
54. Zabarovsky, E. R. and R. L. Allikmets. 1986. An improved technique for efficient construction of gene libraries by partial filling-in of cohesive ends. Gene 42:119–123.
55. Zabarovsky, E. R. and G. Winberg. 1990. High efficiency electroporation of ligated DNA into bacteria. Nucl. Acid Res. 18:5912.

LITERATURE OF DRAFT PUBLICATION 2

1. Beliveau, C., C. Potvin, J. Trudel, A. Asselin, and G. Bellemare. 1991. Cloning, sequencing and expression in *Escherichia coli* of a *Streptococcus faecalis* autolysin. J. Bacteriol. 173:5619–5623.
2. Buist, G., J. Kok, K. J. Leenhouts, M. Dabrowska, G. Venema, and A. J. Haandrikman. 1995. Molecular cloning and nucleotide sequence of the gene encoding the major petidoglycan hydrolase of *Lactococcus lactis*, a muramidase neede for cell separation. J. Bacteriol 177:1554–1563.
3. Casadaban, M. J. and S. N. Cohen. 1980. Analysis of gene control signals by DNA fusion and cloning in *Escherichia coli*. J. Mol. Biol. 138:179–207.
4. Gasson, M. J. 1983. Plasmid complements of *Streptococcus lactis* NCDO 712 and other lactic Streptococci after protoplast-induced curing. J. Bacteriol. 154:1–9.
5. Holo, H. and I. F. Nes. 1989. High-frequency transformation, by electroporation, of *Lactococcus lactis* subsp. *cremoris* grown with glycine in osmotically stabilized media. Appl. Environ. Microbiol. 55:3119–3123.
6. Jayaswal, R. K., Y. -I. Lee, and B. J. Wilkinson. 1990. Cloning and expression of a *Staphylococcus aureus* gene encoding a peptidoglycan hydrolase activity. J. Bacteriol. 172:5783–5788.
7. Kok, J. 1992. Special-purpose vectors for lactococci, p. 97–102. In G. Dunny, P. P. Cleary, and L. L. McKay (eds.), Genetics and molecular biology of Streptococci, Lactococci, and Enterococci. American Society for Microbiology, Washington, D.C.
8. Laemmli, U. K. 1970. Cleavage of structural proteins during the assembly of the head of bacteriophage T4. Nature(London) 227:680–685.
9. Langsrud. T., A. Landaas, and H. B. Castberg. 1987. Autolytic properties of different strains of group N streptococci. Milchwissenschaft 42:556–560.
10. Zabarovsky, E. R. and G. Winberg. 1990. High efficiency electroporation of ligated DNA into bacteria. Nucl. Acid Res. 18:5912.
11. Leenhouts, K. J. and G. Venema. 1993. Lactococcal plasmid vectors, p. 65–94. In K. G. Hardy (ed.), Plasmids, a practical approach. Oxford University Press, Oxford.
12 Mierau, I., A. J. Haandrikman, O. Velterop, P. S. T. Tan, K. J. Leenhouts, W. N. Konings, G. Venema, and J. Kok. 1994. Tripeptidase gene (pepT) of *Lactococcus lactis*: molecular cloning and nucleotide sequencing of pepT and construction of a chromosomal deletion mutant. J. Bacteriol 176:2854–2861.
13. Mierau, I., P. S. T. Tan, A. J. Haandrikman. J. Kok, K. J. Leenhouts, W. N. Konings, and C. Venema. 1993. Cloning and sequencing of the gene for a lactococcal endopeptidase. an enzyme with sequence similarity to mammalian enkephalinase. J. Bacteriol 175:2087–2096.
14. Nauta, A., D. Van Sinderen, H. A. Karsens, J. Kok, and G. Venema. 1994. Inducible lysis of *Lactococcus lactis* mediated by the *Lactococcus lactis* subsp. *cremoris* bacteriophage R1-t functions. (EP 94201353.3)
15. Nauta, A., D. Van Sinderen, J. Kok, and G. Venema. 1994. Inducible gene expression mediated by a repressor-operator system isolated from *Lactococcus lactis* subsp. *cremoris* bacteriophage R1-t. (EP 94201353.3)
16. Olson, N. F. 1990. The impact of lactic acid bacteria on cheese flavour. FEMS Microbiol. Rev. 87:131–148.
17. Potvin, C., D. Leclerc, G. Tremblay, A. Asselin, and C. Bellemare. 1988. Cloning, sequencing and expression of a Bacillus bacteriolytic enzyme in *Escherichia coli*. Mol. Gen. Genet. 214:241–248.
18. Pritchard, G. G. and T. Coolbear. 1993. The physiology and biochemistry of the proteolytic system in lactic acid bacteria. FEMS Microbiol. Rev. 12:179–206.
19. Sambrook, J., E. F. Fritsch, and T. Maniatis. 1989. Molecular cloning—a laboratory manual. Cold Spring Harbor Laboratory Press, Cold Spring Harbor, N.Y.
20. Tan, P. S. T., M.-P. Chapot-Chartier, K. M. Pos, M. Rousseau, C.-Y. Boquien, J.-C. Gripon, and W. N. Konings. 1992. Localization of peptidases in lactococci. Appl. Environ. Microbiol. 58:285–290.
21. Tan, P. S. T., B. Poolman, and W. N. Konings. 1993. Proteolytic enzymes of *Lactococcus lactis*. J. Dairy Res. 60:269–286.
22. Thomas, T. D. and G. G. Pritchard. 1987. Proteolytic enzymes of dairy starter cultures. FEMS Microbiol. Rev. 46:245–268.
23. Towbin, H., T. Staechelin, and J. Gordon. 1979. Electrophoretic transfer of proteins from polyacrylamide gels to nitrocellulose sheets: procedure and some applications. Proc. Natl. Acad. Sci. USA 76:4350–4354.
24. Vagerud, G., H. B. Castberg, and T. Langsrud. 1983. Autolysis of group N Streptococci. Effects of media composition and temperature. J. Dairy. Sci 66:2294–2302.
25. Van Asseldonk, M., G. Rutten, M. Oteman, R. J. Siezen, W. M. de VOS, and C. Simons. 1990. Cloning of usp45, a gene encoding a secreted protein from *Lactococcus lactis* subsp. *lactis* MG1363. Gene 95:155–160.
26. van de Guchte, M., J. Kodde, J. M. B. M. van der Vossen, J. Kok, and G. Venema. 1990. Heterologous gene expression in *Lactococcus lactis* subsp. *lactis*: synthesis, secretion, and processing of the *Bacillus subtilis* neutral protease. Appl. Environ. Microbiol. 56:2606–2611.

27. Van Sinderen, D., G. Galli, P. Cosmina, F. De Ferra, S. Withoff, G. Venema, and G. Grandi. 1993. Characterization of the srfA locus of *Bacillus subtilis*: only the valine-activating domain of srfA is involved in the establishment of genetic competence. Mol. Microbiol. 8:833–841.
28. Van Sinderen, D., H. A. Karsens, G. Venema, and A. Nauta. 1994. (unpublished results).
29. Visser, F. M. W. 1977. Contribution of enzymes from rennet, starter bacteria and milk to proteolysis and flavour development in Gouda cheese. 2. Development of bitterness and cheese flavour. Neth. Milk Dairy J. 31:188–209.

SEQUENCE LISTING

Sequence id no 1 is the nucleotide sequence of FIG. 4.

Sequence id no 2 is the amino acid sequence of the lysin of FIG. 4 and also corresponds to the lysin of *L. lactis* amino acid sequence of FIG. 5A.

Sequence id no 3 is the membrane spanning domain identified within the stretch of amino acids forming lysin of FIG. 5.

Sequence id no 4 is an amino acid sequence comprising the 3 direct repeats of FIG. 6.

Sequence id no 5 is the nucleotide sequence of the promoter region of acmA as in FIG. 14.

Sequence id no 6–9 are primers or probes.

Sequence id no 10 is the amino acid sequence of ORF A.

Sequence id no 11 is the nucleic acid sequence of FIG. 4-ORF B nt 1823–1928.

We claim:

1. A process for the lysis of a culture of lactic acid bacteria by means of a lysin, which comprises the in situ production of a homologous or a heterologous autolysin obtained from food grade Gram-positive lactic acid bacteria, or active fragments of such autolysin to achieve an enhanced lysis during fermentation or before 12 hours in the stationary phase have lapsed, in which a gene encoding said autolysin or active fragment thereof is under control of a regulatable promoter, said enhanced lysis being due to enhanced total autolysin activity compared with natural autolysin activity, after induction of said regulatable promoter, said regulatable promoter not being the native promoter of said autolysin encoding gene;

wherein a homologous autolysin comprises an autolysin obtained from the same species of lactic acid bacteria used in the culture process and a heterologous autolysin comprises an autolysin obtained from a species of bacteria distinct from that used in the culture process;

wherein the lysis of a culture of lactic acid bacteria is deemed to be enhanced when the optical density (OD) value of the culture is lower than cultures of lactic acid bacteria lacking in situ expression of homologous or heterologous autolysin activity and lactic acid bacteria having native, constitutively expressed autolysin activity; and wherein an active fragment of a gene encoding said autolysin is defined to be a fragment of the gene, which upon expression, exhibits the activity of the autolysin, as determined by a hydrolase activity test.

2. Process according to claim 1, in which said regulatable promoter is regulatable by food-grade ingredients or parameters.

3. Process according to claim 1, in which the autolysin is first produced and subsequently used as a bactericidal agent against spoiling bacteria or pathogenic bacteria.

4. Process according to claim 1, in which enhanced lysis is achieved before 4 hours in the stationary phase have elapsed.

5. Process according to claim 1, in which the gene encoding said autolysin encodes homologous autolysin.

6. Process according to claim 1, in which the culture of lactic acid bacteria is part of a product containing such culture.

7. Process according to claim 6, in which the lactic acid bacteria culture is used for producing a fermented food product obtainable by the fermentative action of the lactic acid bacteria and subsequently the lactic acid bacteria in the fermented food product are lysed.

8. Process according to claim 7, in which the fermented food product is a cheese product.

9. A process according to claim 7, wherein the fermented food product obtained by the fermentative action of the lactic acid bacteria is a cheese product, and the lactic acid bacteria in the cheese product undergo lysis subsequent to fermentation; whereby at least some intracellular proteolytic enzymes leave the lysed bacteria and change the composition of the cheese product, further ripening the cheese product.

10. Process for improving the shelf life of a consumer product, in which a product obtained by a process as claimed in claim 1 and containing free autolysin is incorporated into said consumer product in such amount that in the resulting consumer product the growth of spoiling bacteria or pathogenic bacteria is inhibited or that their viability is strongly reduced.

11. A process according to claim 10, in which the consumer product is selected from the group consisting of edible products, cosmetic products, products for cleaning fabrics, products for cleaning hard surfaces and products for cleansing human skin.

12. Process for modifying a mixture of peptides, which comprises treating a mixture of peptides obtained by proteolysis of proteins with a lysed culture obtained by a process according to claim 1.

13. A process for modifying a mixture of peptides, in which a mixture of peptides obtained by proteolysis of proteins is combined with a culture of lactic acid bacteria containing a lactic acid bacterium autolysin gene under control of a regulatable promoter and subsequently the steps according to the process as defined in claim 1 are carried out, such that the promoter is induced to achieve production of autolysin in such amount that the lactic acid bacteria are lysed and the released contents of the lysed cells, including peptidases, modify the composition of the mixture of peptides.

14. Process according to claim 13 or 12, in which the proteins comprise milk proteins or vegetable proteins, or both.

15. A nucleotide sequence encoding a lysin obtained from a lactobacillus, said lysin having N-acetylmuramidase activity.

16. A nucleotide sequence according to claim 15, said nucleotide sequence encoding an amino acid sequence according to SEQ ID NO:2.

17. A nucleotide sequence according to claim 15 encoding an N-terminal amino acid sequence which comprises amino acids 65–220 of SEQ ID NO:2.

18. A nucleotide sequence according to claim 15 comprising at least nucleic acid sequences encoding 3 direct repeats according to SEQ ID NO:4.

19. A nucleotide sequence according to claim 15 comprising at least a nucleic acid sequence encoding a membrane spanning domain according to SEQ ID NO:3.

20. A recombinant vector comprising a nucleotide sequence according to claim 15, said nucleotide sequence being under control of a promoter other than the native promoter of the lysin encoding nucleotide sequence, wherein said promoter is obtained from a food-grade organsim.

21. A method of producing an autolysin or an active fragment thereof comprising:
obtaining a recombinant vector according to claim 20 and expressing said recombinant vector in a host cell.

22. A recombinant host cell comprising a recombinant vector according to claim 20, said nucleotide sequence being under control of a promoter other than that naturally occurring with the lysin gene.

23. A recombinant host cell according to claim 22, said host cell being foodgrade grampositive such as a lactic acid bacterium.

24. A recombinant host cell according to claims 22 or 23 further comprising a native autolysin gene under control of its native promoter such that autolysin production during the exponential growth phase of said cell is sufficient to ensure separation of said cell from other cells within a culture.

25. A nucleotide sequence encoding a polypeptide or protein having lytic activity, said sequence being obtained from a lactobacillus.

26. A nucleotide sequence according to claims 15 or 25, said nucleotide sequence being a sequence according to SEQ ID NO:1 or a variant nucleotide sequence encoding a functional equivalent of an amino acid sequence encoded by SEQ ID NO:1.

27. A nucleotide sequence according to claims 15 or 25 which hybridizes to a nucleic acid sequence according to SEQ ID NO:1 under normal to stringent conditions.

* * * * *

```
                        SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 1930 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Lactococcus lactis
         (B) STRAIN: MG1363

(vii) IMMEDIATE SOURCE:
          (B) CLONE: Fig.4 (publ.1)-acmA and ORFA (ix) FEATURE:
         (A) NAME/KEY: CDS
         (B) LOCATION: 178..1489

(ix) FEATURE:
         (A) NAME/KEY: CDS
         (B) LOCATION: complement (1542..1824)

(xi) SEQUENCE DESCRIPTION: SEQ ID NO: 1:

ATTTTTGTTT TAAATCAGAT TTTTTAGATT AAAGGCAAAA AGTTTTTACA AATATGAATC          60

CTTAACGGAA AAACGTTTAC AAACCGCCAC CAAATTGACA TCTTTTTTTA GCTTGAGGCG        120

TGGTAGAATA AAGATAGTAC TTATTATATT TTGTAATCTT TAGAAAGGTA ATTATTT          177

ATG CCA GTA TCA CGT GTT AAA GTT AAA AAT AGA CAT TTA AAA AAG AAA          225
Met Pro Val Ser Arg Val Lys Val Lys Asn Arg His Leu Lys Lys Lys
  1               5                  10                  15

ACT AAA AAA CCA CTC GCT TTT TAT AAA CCA GCC ACA AAA TTT GCT GGC          273
Thr Lys Lys Pro Leu Ala Phe Tyr Lys Pro Ala Thr Lys Phe Ala Gly
             20                  25                  30

GCT GTT CTT ATT GCC GGA ACA TTG ACA ACC ACA CAT GAA CTT CTT CTT          321
Ala Val Leu Ile Ala Gly Thr Leu Thr Thr Thr His Glu Leu Leu Leu
         35                  40                  45

CAA CAG ACA AGT CCA ATG GTT CAA GCA GCG ACT AAC TCA TCA GAG GTT          369
Gln Gln Thr Ser Pro Met Val Gln Ala Ala Thr Asn Ser Ser Glu Val
     50                  55                  60

TTT ATT GAA AGT ATT GCC GCA TCA GCA AAA CCT GTG GCA GAT GCT AAT          417
Phe Ile Glu Ser Ile Ala Ala Ser Ala Lys Pro Val Ala Asp Ala Asn
 65                  70                  75                  80
```

```
GGC TTA TAT CCT TCG GTC ATG ATT GCC CAA GCT ATT TTG GAA AGC AAC       465
Gly Leu Tyr Pro Ser Val Met Ile Ala Gln Ala Ile Leu Glu Ser Asn
                 85                  90                  95

TGG GGC TCA AGT CAG CTT TCA CGA GCT CCC TAT TAT AAT TTA TTT GGT       513
Trp Gly Ser Ser Gln Leu Ser Arg Ala Pro Tyr Tyr Asn Leu Phe Gly
                100                 105                 110

ATT CAA GGT ACT TAT CAA GGA AAG AGC GTC GTA TTT AAA ACT CAA GAG       561
Ile Gln Gly Thr Tyr Gln Gly Lys Ser Val Val Phe Lys Thr Gln Glu
            115                 120                 125

TAT CTC AAT GGT AAA TGG GTG ACT AAA GAT ATG CCC TTT AGG GTC TAT       609
Tyr Leu Asn Gly Lys Trp Val Thr Lys Asp Met Pro Phe Arg Val Tyr
            130                 135                 140

CCT TCC TTT AAT CAA AGT TTT CAA GAC AAT GCT TAT GTT CTA AAA ACA       657
Pro Ser Phe Asn Gln Ser Phe Gln Asp Asn Ala Tyr Val Leu Lys Thr
145                 150                 155                 160

ACA AAC TTT GGG AAT GGT CCC TAT TAC GCT AAG GCT TGG CGG GCC AAT       705
Thr Asn Phe Gly Asn Gly Pro Tyr Tyr Ala Lys Ala Trp Arg Ala Asn
                165                 170                 175

GCT GCC ACC TAT CAA GAC GCT ACT GCT GCT TTG ACG GGC AGA TAT GCT       753
Ala Ala Thr Tyr Gln Asp Ala Thr Ala Ala Leu Thr Gly Arg Tyr Ala
            180                 185                 190

ACC GAC CCA AGT TAT GGC GCT TCA CTG AAT CGC ATT ATT TCT CAA TAT       801
Thr Asp Pro Ser Tyr Gly Ala Ser Leu Asn Arg Ile Ile Ser Gln Tyr
            195                 200                 205

AAT TTG ACT CGT TTT GAC GGA GCT TCT TCA GCT GGA AAT ACT AAT TCT       849
Asn Leu Thr Arg Phe Asp Gly Ala Ser Ser Ala Gly Asn Thr Asn Ser
210                 215                 220

GGT GGC TCG ACA ACC ACA ATT ACG AAT AAT AAT TCT GGA ACC AAT AGC       897
Gly Gly Ser Thr Thr Thr Ile Thr Asn Asn Asn Ser Gly Thr Asn Ser
225                 230                 235                 240

AGT TCA ACT ACT TAT ACC GTC AAA TCT GGT GAT ACT CTT TGG GGA ATC       945
Ser Ser Thr Thr Tyr Thr Val Lys Ser Gly Asp Thr Leu Trp Gly Ile
                245                 250                 255

TCA CAA AGA TAT GGA ATT AGT GTC GCT CAA ATT CAA AGT GCG AAT AAT       993
Ser Gln Arg Tyr Gly Ile Ser Val Ala Gln Ile Gln Ser Ala Asn Asn
            260                 265                 270

CTT AAA AGT ACC ATT ATC TAC ATT GGT CAA AAA CTT GTA CTG ACA GGT      1041
Leu Lys Ser Thr Ile Ile Tyr Ile Gly Gln Lys Leu Val Leu Thr Gly
            275                 280                 285

TCA GCT TCT TCT ACA AAT TCA GGT GGT TCA AAC AAT TCC GCA AGC ACT      1089
Ser Ala Ser Ser Thr Asn Ser Gly Gly Ser Asn Asn Ser Ala Ser Thr
290                 295                 300

ACT CCA ACC ACT TCT GTG ACA CCT GCA AAA CCA ACT TCA CAA ACA ACT      1137
Thr Pro Thr Thr Ser Val Thr Pro Ala Lys Pro Thr Ser Gln Thr Thr
305                 310                 315                 320

GTT AAG GTT AAA TCC GGA GAT ACC CTT TGG GCG CTA TCA GTA AAA TAT      1185
Val Lys Val Lys Ser Gly Asp Thr Leu Trp Ala Leu Ser Val Lys Tyr
                325                 330                 335

AAA ACT AGT ATT GCT CAA TTG AAA AGT TGG AAT CAT TTA AGT TCA GAT      1233
Lys Thr Ser Ile Ala Gln Leu Lys Ser Trp Asn His Leu Ser Ser Asp
            340                 345                 350

ACC ATT TAT ATT GGT CAA AAT CTT ATT GTT TCA CAA TCT GCT GCT GCT      1281
Thr Ile Tyr Ile Gly Gln Asn Leu Ile Val Ser Gln Ser Ala Ala Ala
            355                 360                 365

TCA AAT CCT TCG ACA GGT TCA GGC TCA ACT GCT ACC AAT AAC TCA AAC      1329
Ser Asn Pro Ser Thr Gly Ser Gly Ser Thr Ala Thr Asn Asn Ser Asn
370                 375                 380

TCG ACT TCT TCT AAC TCA AAT GCC TCA ATT CAT AAG GTC GTT AAA GGA      1377
Ser Thr Ser Ser Asn Ser Asn Ala Ser Ile His Lys Val Val Lys Gly
385                 390                 395                 400
```

```
GAT ACT CTC TGG GGA CTT TCG CAA AAA TCT GGC AGC CCA ATT GCT TCA    1425
Asp Thr Leu Trp Gly Leu Ser Gln Lys Ser Gly Ser Pro Ile Ala Ser
                405                 410                 415

ATC AAG GCT TGG AAT CAT TTA TCT AGC GAT ACT ATT TTA ATT GGT CAG    1473
Ile Lys Ala Trp Asn His Leu Ser Ser Asp Thr Ile Leu Ile Gly Gln
        420                 425                 430

TAT CTA CGA ATA AAA T AAATTATTAT TAATGAACTT TTAGTTAATA AAAAAGAAT   1529
Tyr Leu Arg Ile Lys
            435

GAAATTCAAT TCATTCTTTT TTTAATTCTT GTAAAACCGC TTGAAGATGG ATAGAACGGG  1589

TCGGTTCTGA CATTCCAACA GTCATTTCCC AAGGAGTTGT TTCTTTTTCA AGAGCCAATT  1649

CAAGAAAAAC ACGTTGAAAT GAAGTTAATT CTTCACAGTT CGTTAAATAG TCAATCTCTT  1709

TTTTAGAGAG CAAAATTTTG TCACGTTGAA TCACTTTGTT TAGGTAGCGA ACCCAAAGTT  1769

CTAAATTCCA TTTGGATTTT TGGGCAGCCT GCAAGAGATA TTCAATCCAC GTCATTGTAA  1829

TAACCTCAGT ATTTTTGGAT TTTTTCGTAA ATAATTTTTT AAAGCTTCTT CACCATAAGC  1889

CAAACTATAA GCTTCTAAAA TAACCGCTGG GTCTGCCGAT C                     1930
```

(2) INFORMATION FOR SEQ ID NO: 2:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Pro Val Ser Arg Val Lys Val Lys Asn Arg His Leu Lys Lys Lys
  1               5                  10                  15

Thr Lys Lys Pro Leu Ala Phe Tyr Lys Pro Ala Thr Lys Phe Ala Gly
             20                  25                  30

Ala Val Leu Ile Ala Gly Thr Leu Thr Thr His Glu Leu Leu Leu
         35                  40                  45

Gln Gln Thr Ser Pro Met Val Gln Ala Ala Thr Asn Ser Ser Glu Val
     50                  55                  60

Phe Ile Glu Ser Ile Ala Ala Ser Ala Lys Pro Val Ala Asp Ala Asn
 65                  70                  75                  80

Gly Leu Tyr Pro Ser Val Met Ile Ala Gln Ala Ile Leu Glu Ser Asn
                 85                  90                  95

Trp Gly Ser Ser Gln Leu Ser Arg Ala Pro Tyr Tyr Asn Leu Phe Gly
                100                 105                 110

Ile Gln Gly Thr Tyr Gln Gly Lys Ser Val Val Phe Lys Thr Gln Glu
            115                 120                 125

Tyr Leu Asn Gly Lys Trp Val Thr Lys Asp Met Pro Phe Arg Val Tyr
    130                 135                 140

Pro Ser Phe Asn Gln Ser Phe Gln Asp Asn Ala Tyr Val Leu Lys Thr
145                 150                 155                 160

Thr Asn Phe Gly Asn Gly Pro Tyr Tyr Ala Lys Ala Trp Arg Ala Asn
                165                 170                 175

Ala Ala Thr Tyr Gln Asp Ala Thr Ala Ala Leu Thr Gly Arg Tyr Ala
            180                 185                 190

Thr Asp Pro Ser Tyr Gly Ala Ser Leu Asn Arg Ile Ile Ser Gln Tyr
        195                 200                 205

Asn Leu Thr Arg Phe Asp Gly Ala Ser Ser Ala Gly Asn Thr Asn Ser
    210                 215                 220
```

```
Gly Gly Ser Thr Thr Thr Ile Thr Asn Asn Ser Gly Thr Asn Ser
225                 230                 235                 240

Ser Ser Thr Thr Tyr Thr Val Lys Ser Gly Asp Thr Leu Trp Gly Ile
            245                 250                 255

Ser Gln Arg Tyr Gly Ile Ser Val Ala Gln Ile Gln Ser Ala Asn Asn
            260                 265                 270

Leu Lys Ser Thr Ile Ile Tyr Ile Gly Gln Lys Leu Val Leu Thr Gly
        275                 280                 285

Ser Ala Ser Ser Thr Asn Ser Gly Gly Ser Asn Asn Ser Ala Ser Thr
        290                 295                 300

Thr Pro Thr Thr Ser Val Thr Pro Ala Lys Pro Thr Ser Gln Thr Thr
305                 310                 315                 320

Val Lys Val Lys Ser Gly Asp Thr Leu Trp Ala Leu Ser Val Lys Tyr
                325                 330                 335

Lys Thr Ser Ile Ala Gln Leu Lys Ser Trp Asn His Leu Ser Ser Asp
                340                 345                 350

Thr Ile Tyr Ile Gly Gln Asn Leu Ile Val Ser Gln Ser Ala Ala Ala
                355                 360                 365

Ser Asn Pro Ser Thr Gly Ser Gly Ser Thr Ala Thr Asn Asn Ser Asn
370                 375                 380

Ser Thr Ser Ser Asn Ser Asn Ala Ser Ile His Lys Val Val Lys Gly
385                 390                 395                 400

Asp Thr Leu Trp Gly Leu Ser Gln Lys Ser Gly Ser Pro Ile Ala Ser
                405                 410                 415

Ile Lys Ala Trp Asn His Leu Ser Ser Asp Thr Ile Leu Ile Gly Gln
                420                 425                 430

Tyr Leu Arg Ile Lys
        435

(2) INFORMATION FOR SEQ ID NO: 3:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 3:

Phe Ala Gly Ala Val Leu Ile Ala Gly Thr Leu Thr Thr Thr
1               5                   10                  15

(2) INFORMATION FOR SEQ ID NO: 4:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO: 4:

Thr Asn Ser Gly Gly Ser Thr Thr Thr Ile Thr Asn Asn Ser Gly
1               5                   10                  15

Thr Asn Ser Ser Ser Thr Thr Tyr Thr Val Lys Ser Gly Asp Thr Leu
                20                  25                  30

Trp Gly Ile Ser Gln Arg Tyr Gly Ile Ser Val Ala Gln Ile Gln Ser
            35                  40                  45

Ala Asn Asn Leu Lys Ser Thr Ile Ile Tyr Ile Gly Gln Lys Leu Val
```

```
                  50                55                60
Leu Thr Gly Ser Ala Ser Ser Thr Asn Ser Gly Gly Ser Asn Asn Ser
 65                 70                 75                 80

Ala Ser Thr Thr Pro Thr Thr Ser Val Thr Pro Ala Lys Pro Thr Ser
                85                 90                 95

Gln Thr Thr Val Lys Val Lys Ser Gly Asp Thr Leu Trp Ala Leu Ser
               100                105                110

Val Lys Tyr Lys Thr Ser Ile Ala Gln Leu Lys Ser Trp Asn His Leu
           115                120                125

Ser Ser Asp Thr Ile Tyr Ile Gly Gln Asn Leu Ile Val Ser Gln Ser
130                135                140

Ala Ala Ala Ser Asn Pro Ser Thr Gly Ser Gly Ser Thr Ala Thr Asn
145                150                155                160

Asn Ser Asn Ser Thr Ser Ser Asn Ser Asn Ala Ser Ile His Lys Val
               165                170                175

Val Lys Gly Asp Thr Leu Trp Gly Leu Ser Gln Lys Ser Gly Ser Pro
               180                185                190

Ile Ala Ser Ile Lys Ala Trp Asn His Leu Ser Ser Asp Thr Ile Leu
           195                200                205

Ile Gly Gln Tyr Leu Arg Ile Lys
210                215
```

(2) INFORMATION FOR SEQ ID NO: 5:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Lactococcus lactis
        (B) STRAIN: MG1363

(vii) IMMEDIATE SOURCE:
        (B) CLONE: Fig.14a acmA promoter region (xi) SEQUENCE DESCRIPTION: SEQ ID NO: 5:

```
AATATTTTTG TTTTAAATCA GATTTTTTAG ATTAAAGGCA AAAAGTTTTT ACAAATATGA    60

ATCCTTAACG GAAAAACGTT TACAAACCGC CACCAAATTG ACATCTTTTT TTAGCTTGAG   120

GCGTGGTAGA ATAAAGATAG TACTTATTAT ATTTTGTAAT CTTTAGAAAG GTAATTATTT   180

ATG                                                                183
```

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Lactococcus lactis
        (B) STRAIN: MG1363

(vii) IMMEDIATE SOURCE:
        (B) CLONE: primer PALA-4

(xi) SEQUENCE DESCRIPTION: SEQ ID NO: 6:

CTTCAACAGA CAAGTCC                                                              17

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Lactococcus lactis
        (B) STRAIN: MG1363

(vii) IMMEDIATE SOURCE:
        (B) CLONE: primer PALA-14

(xi) SEQUENCE DESCRIPTION: SEQ ID NO: 7:

GATAAATGAT TCCAAGC                                                              17

(2) INFORMATION FOR SEQ ID NO: 8:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Lactococcus lactis
        (B) STRAIN: MG1363

(vii) IMMEDIATE SOURCE:
        (B) CLONE: PALA-19

(xi) SEQUENCE DESCRIPTION: SEQ ID NO: 8:

CAAGGTTAAG TCCACG                                                               16

(2) INFORMATION FOR SEQ ID NO: 9:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Lactococcus lactis
        (B) STRAIN: MG1363

(vii) IMMEDIATE SOURCE:
        (B) CLONE: primer BK05AL (xi) SEQUENCE DESCRIPTION: SEQ ID NO: 9:

ATTATTTGAT TGGAGTT                                                              17

(2) INFORMATION FOR SEQ ID NO: 10:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Thr Trp Ile Glu Tyr Leu Leu Gln Ala Ala Gln Lys Ser Lys Trp
 1               5                  10                  15

Asn Leu Glu Leu Trp Val Arg Tyr Leu Asn Lys Val Ile Gln Arg Asp
                20                  25                  30

Lys Ile Leu Leu Ser Lys Lys Glu Ile Asp Tyr Leu Thr Asn Cys Glu
                35                  40                  45

Glu Leu Thr Ser Phe Gln Arg Val Phe Leu Glu Leu Ala Leu Glu Lys
        50                  55                  60

Glu Thr Thr Pro Trp Glu Met Thr Val Gly Met Ser Glu Pro Thr Arg
 65              70                  75                  80

Ser Ile His Leu Gln Ala Val Leu Gln Glu Leu Lys Lys Glu
                85                  90
```

(2) INFORMATION FOR SEQ ID NO: 11:

(i) SEQUENCE CHARACTERISTICS:
        (A) LENGTH: 1930 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Lactococcus lactis
        (B) STRAIN: MG1363

(vii) IMMEDIATE SOURCE:
        (B) CLONE: Fig.4 - ORFB (ix) FEATURE:
        (A) NAME/KEY: CDS
        (B) LOCATION: complement (1823..1928)

(xi) SEQUENCE DESCRIPTION: SEQ ID NO: 11:

```
ATTTTTGTTT TAAATCAGAT TTTTTAGATT AAAGGCAAAA AGTTTTTACA AATATGAATC    60

CTTAACGGAA AAACGTTTAC AAACCGCCAC CAAATTGACA TCTTTTTTTA GCTTGAGGCG   120

TGGTAGAATA AAGATAGTAC TTATTATATT TTGTAATCTT TAGAAAGGTA ATTATTTATG   180

CCAGTATCAC GTGTTAAAGT TAAAAATAGA CATTTAAAAA AGAAAACTAA AAAACCACTC   240

GCTTTTTATA AACCAGCCAC AAAATTTGCT GGCGCTGTTC TTATTGCCGG AACATTGACA   300

ACCACACATG AACTTCTTCT TCAACAGACA AGTCCAATGG TTCAAGCAGC GACTAACTCA   360

TCAGAGGTTT TTATTGAAAG TATTGCCGCA TCAGCAAAAC CTGTGGCAGA TGCTAATGGC   420

TTATATCCTT CGGTCATGAT TGCCCAAGCT ATTTTGGAAA GCAACTGGGG CTCAAGTCAG   480

CTTTCACGAG CTCCCTATTA TAATTTATTT GGTATTCAAG GTACTTATCA AGGAAAGAGC   540

GTCGTATTTA AAACTCAAGA GTATCTCAAT GGTAAATGGG TGACTAAAGA TATGCCCTTT   600

AGGGTCTATC CTTCCTTTAA TCAAAGTTTT CAAGACAATG CTTATGTTCT AAAAACAACA   660

AACTTTGGGA ATGGTCCCTA TTACGCTAAG GCTTGGCGGG CCAATGCTGC CACCTATCAA   720

GACGCTACTG CTGCTTTGAC GGGCAGATAT GCTACCGACC CAAGTTATGG CGCTTCACTG   780

AATCGCATTA TTTCTCAATA TAATTTGACT CGTTTTGACG GAGCTTCTTC AGCTGGAAAT   840

ACTAATTCTG GTGGCTCGAC AACCACAATT ACGAATAATA ATTCTGGAAC CAATAGCAGT   900

TCAACTACTT ATACCGTCAA ATCTGGTGAT ACTCTTTGGG GAATCTCACA AAGATATGGA   960

ATTAGTGTCG CTCAAATTCA AAGTGCGAAT AATCTTAAAA GTACCATTAT CTACATTGGT  1020

CAAAAACTTG TACTGACAGG TTCAGCTTCT TCTACAAATT CAGGTGGTTC AAACAATTCC  1080

GCAAGCACTA CTCCAACCAC TTCTGTGACA CCTGCAAAAC CAACTTCACA AACAACTGTT  1140
```

-continued

```
AAGGTTAAAT CCGGAGATAC CCTTTGGGCG CTATCAGTAA AATATAAAAC TAGTATTGCT      1200

CAATTGAAAA GTTGGAATCA TTTAAGTTCA GATACCATTT ATATTGGTCA AAATCTTATT      1260

GTTTCACAAT CTGCTGCTGC TTCAAATCCT TCGACAGGTT CAGGCTCAAC TGCTACCAAT      1320

AACTCAAACT CGACTTCTTC TAACTCAAAT GCCTCAATTC ATAAGGTCGT TAAAGGAGAT      1380

ACTCTCTGGG GACTTTCGCA AAAATCTGGC AGCCCAATTG CTTCAATCAA GGCTTGGAAT      1440

CATTTATCTA GCGATACTAT TTTAATTGGT CAGTATCTAC GAATAAAATA AATTATTATT      1500

AATGAACTTT TAGTTAATAA AAAAAGAATG AAATTCAATT CATTCTTTTT TTAATTCTTG      1560

TAAAACCGCT TGAAGATGGA TAGAACGGGT CGGTTCTGAC ATTCCAACAG TCATTTCCCA      1620

AGGAGTTGTT TCTTTTTCAA GAGCCAATTC AAGAAAAACA CGTTGAAATG AAGTTAATTC      1680

TTCACAGTTC GTTAAATAGT CAATCTCTTT TTTAGAGAGC AAAATTTTGT CACGTTGAAT      1740

CACTTTGTTT AGGTAGCGAA CCCAAAGTTC TAAATTCCAT TTGGATTTTT GGGCAGCCTG      1800

CAAGAGATAT TCAATCCACG TCATTGTAAT AACCTCAGTA TTTTTGGATT TTTTCGTAAA      1860

TAATTTTTTA AAGCTTCTTC ACCATAAGCC AAACTATAAG CTTCTAAAAT AACCGCTGGG      1920

TCTGCCGATC                                                            1930
```

(2) INFORMATION FOR SEQ ID NO: 12:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO: 12:

```
Ser Ala Asp Pro Ala Val Ile Leu Glu Ala Tyr Ser Leu Ala Tyr Gly
 1               5                  10                  15

Glu Glu Ala Leu Lys Asn Tyr Leu Arg Lys Asn Pro Lys Ile Leu Arg
            20                  25                  30

Leu Leu Gln
        35
```

(2) INFORMATION FOR SEQ ID NO: 13:

(i) SEQUENCE CHARACTERISTICS:
        (A) LENGTH: 671 amino acids
        (B) TYPE: amino acid
        (D) TOPOLOGY: linear (ii) MOLECULE TYPE: protein (vi) ORIGINAL SOURCE:
        (A) ORGANISM: Streptococcus faecalis (vii) IMMEDIATE SOURCE:
        (B) CLONE: Fig.5a (S. faecalis)

(xi) SEQUENCE DESCRIPTION: SEQ ID NO: 13:

```
    Met Lys Lys Glu Ser Met Ser Arg Ile Glu Arg Arg Lys Ala Gln Gln
     1               5                  10                  15

Arg Lys Lys Thr Pro Val Gln Trp Lys Lys Ser Thr Thr Leu Phe Ser
                    20                  25                  30

Ser Ala Leu Ile Val Ser Ser Val Gly Thr Pro Val Ala Leu Leu Pro
                35                  40                  45

Val Thr Ala Glu Ala Thr Glu Glu Gln Pro Thr Asn Ala Glu Val Ala
            50                  55                  60

Gln Ala Pro Thr Thr Glu Thr Gly Leu Val Glu Thr Pro Thr Thr Glu
```

```
             65                  70                  75                  80
        Thr Thr Pro Gly Ile Thr Glu Gln Pro Thr Asp Ser Ser Thr Thr
                            85                  90                  95
        Thr Glu Ser Thr Thr Glu Ser Ser Lys Glu Thr Pro Thr Pro Ser
                           100                 105                 110
        Thr Glu Gln Pro Thr Val Asp Ser Thr Pro Val Glu Ser Gly Thr
                           115                 120                 125
        Thr Asp Ser Ser Val Ala Glu Ile Thr Pro Val Ala Pro Ser Thr Thr
                           130                 135                 140
        Glu Ser Glu Ala Ala Pro Ala Val Thr Pro Asp Asp Glu Val Lys Val
        145                 150                 155                 160
        Pro Glu Ala Arg Val Ala Ser Ala Gln Thr Phe Ser Ala Leu Ser Pro
                           165                 170                 175
        Thr Gln Ser Pro Ser Glu Phe Ile Ala Glu Leu Ala Arg Cys Ala Gln
                           180                 185                 190
        Pro Ile Ala Gln Ala Asn Asp Leu Tyr Ala Ser Val Met Met Ala Gln
                           195                 200                 205
        Ala Ile Val Glu Ser Gly Trp Gly Ala Ser Thr Leu Ser Lys Ala Pro
                           210                 215                 220
        Asn Tyr Asn Leu Phe Gly Ile Lys Gly Ser Tyr Asn Gly Gln Ser Val
        225                 230                 235                 240
        Tyr Met Asp Thr Trp Glu Tyr Leu Asn Gly Lys Trp Leu Val Lys Lys
                           245                 250                 255
        Glu Pro Phe Arg Lys Tyr Pro Ser Tyr Met Glu Ser Phe Gln Asp Asn
                           260                 265                 270
        Ala His Val Leu Lys Thr Thr Ser Phe Gln Ala Gly Val Tyr Tyr Tyr
                           275                 280                 285
        Ala Gly Ala Trp Lys Ser Asn Thr Ser Ser Tyr Arg Asp Ala Thr Ala
                           290                 295                 300
        Trp Leu Thr Gly Arg Tyr Ala Thr Asp Pro Ser Tyr Asn Ala Lys Leu
        305                 310                 315                 320
        Asn Asn Val Ile Thr Ala Tyr Asn Leu Thr Gln Tyr Asp Thr Pro Ser
                           325                 330                 335
        Ser Gly Gly Asn Thr Gly Gly Gly Thr Val Asn Pro Gly Thr Gly Gly
                           340                 345                 350
        Ser Asn Asn Gln Ser Gly Thr Asn Thr Tyr Tyr Thr Val Lys Ser Gly
                           355                 360                 365
        Asp Thr Leu Asn Lys Ile Ala Ala Gln Tyr Gly Val Ser Val Ala Asn
                           370                 375                 380
        Leu Arg Ser Trp Asn Gly Ile Ser Gly Asp Leu Ile Phe Val Gly Gln
        385                 390                 395                 400
        Lys Leu Ile Val Lys Lys Gly Ala Ser Gly Asn Thr Gly Gly Ser Gly
                           405                 410                 415
        Asn Gly Gly Ser Asn Asn Gln Ser Gly Thr Asn Thr Tyr Tyr Thr
                           420                 425                 430
        Val Lys Ser Gly Asp Thr Leu Asn Lys Ile Ala Ala Gln Tyr Gly Val
                           435                 440                 445
        Thr Val Ala Asn Leu Arg Ser Trp Asn Gly Ile Ser Gly Asp Leu Ile
                           450                 455                 460
        Phe Val Gly Gln Lys Leu Ile Val Lys Lys Gly Thr Ser Gly Asn Thr
        465                 470                 475                 480
        Gly Gly Ser Ser Asn Gly Gly Ser Asn Asn Gln Ser Gly Thr Asn
                           485                 490                 495
```

```
            Thr Tyr Tyr Thr Ile Lys Ser Gly Asp Thr Leu Asn Lys Ile Ala Ala
                        500                 505                 510

Gln Tyr Gly Val Ser Val Ala Asn Leu Arg Ser Trp Asn Gly Ile Ser
                        515                 520                 525

Gly Asp Leu Ile Phe Ala Gly Gln Lys Ile Ile Val Lys Lys Gly Thr
                        530                 535                 540

Ser Gly Asn Thr Gly Ser Ser Asn Gly Gly Ser Asn Asn Asn Gln
            545                 550                 555                 560

Ser Gly Thr Asn Thr Tyr Tyr Thr Ile Lys Ser Gly Asp Thr Leu Asn
                        565                 570                 575

Lys Ile Ser Ala Gln Phe Gly Val Ser Val Ala Asn Leu Arg Ser Trp
                        580                 585                 590

Asn Gly Ile Lys Gly Asp Leu Ile Phe Ala Gly Gln Thr Ile Ile Val
                        595                 600                 605

Lys Lys Gly Ala Ser Ala Gly Gly Asn Ala Ser Ser Thr Asn Ser Ala
                        610                 615                 620

Ser Gly Lys Arg His Thr Val Lys Ser Gly Asp Ser Leu Trp Gly Leu
            625                 630                 635                 640

Ser Met Gln Tyr Gly Ile Ser Ile Gln Lys Ile Lys Gln Leu Asn Gly
                        645                 650                 655

Leu Ser Gly Asp Thr Ile Tyr Ile Gly Gln Thr Leu Lys Val Gly
                        660                 665                 670

(2) INFORMATION FOR SEQ ID NO: 14:

(i) SEQUENCE CHARACTERISTICS:
        (A) LENGTH: 666 amino acids
        (B) TYPE: amino acid
        (D) TOPOLOGY: linear (ii) MOLECULE TYPE: protein (vi) ORIGINAL SOURCE:
         (A) ORGANISM: Enterococcus hirae (vii) IMMEDIATE SOURCE:
          (B) CLONE: Fig.5a (E. hirae)

(xi) SEQUENCE DESCRIPTION: SEQ ID NO: 14:

Met Glu Asn Ile Ala Arg Lys Glu Arg Arg Leu Asn Glu Thr Lys
    1               5                   10                  15

Arg Phe Arg Lys Val Lys Arg Ser Ala Ala Leu Val Gly Thr Ala Met
                    20                  25                  30

Val Gly Cys Ser Val Ala Ala Pro Leu Ile Gln Pro Val Gln Val Asp
                    35                  40                  45

Ala Asp Gln Thr Pro Thr Gln Phe Gly Ala Arg Ile Asn Thr Ala Ala
                50                  55                  60

Phe Ile Ala Glu Ile Ala Thr Tyr Ala Gln Pro Ile Ala Gln Ala Asn
    65                  70                  75                  80

Asp Leu Tyr Ala Ser Val Met Ile Ala Gln Ala Val Val Glu Ser Gly
                    85                  90                  95

Trp Gly Ser Ser Ala Leu Ser Gln Ala Pro Tyr Tyr Asn Leu Phe Gly
                    100                 105                 110

Ile Lys Gly Ser Tyr Gln Gly Gln Thr Val Tyr Met Asp Thr Leu Glu
                    115                 120                 125

Tyr Leu Asn Asn Lys Trp Val Ser Lys Lys Glu Pro Phe Arg Gln Tyr
                    130                 135                 140

Pro Ser Phe Ala Glu Ser Phe Asn Asp Asn Ala Tyr Val Leu Arg Asn
    145                 150                 155                 160
```

-continued

```
Thr Ser Phe Gly Asn Gly Tyr Tyr Ala Gly Thr Trp Lys Ser Asn
            165                 170                 175
Thr Lys Ser Tyr Thr Asp Ala Thr Ala Cys Leu Thr Gly Arg Tyr Ala
            180                 185                 190
Thr Asp Pro Gly Tyr Ala Gly Lys Leu Asn Asn Ile Ile Thr Thr Tyr
            195                 200                 205
Gly Leu Thr Lys Tyr Asp Thr Pro Ala Ser Gly Asn Ala Gly Gly Gly
            210                 215                 220
Val Thr Ile Gly Asn Gly Gly Asn Thr Gly Asn Thr Ser Asn Ser Gly
225                 230                 235                 240
Ser Thr Ser Gly Asn Ser Gly Gly Ser Ala Thr Thr Gly Thr Thr
                245                 250                 255
Tyr Thr Val Lys Ser Gly Asp Ser Val Trp Gly Ile Ser His Ser Phe
                260                 265                 270
Gly Ile Thr Met Ala Gln Leu Ile Glu Trp Asn Asn Ile Lys Asn Asn
            275                 280                 285
Phe Ile Tyr Pro Gly Gln Lys Leu Thr Ile Lys Gly Gly Gln Ser Ala
            290                 295                 300
Gly Ser Ser Thr Thr Asn Thr Gly Asn Asn Ala Ser Ser Gly Asn Thr
305                 310                 315                 320
Ser Gly Asn Thr Asn Thr Ser Gly Ser Thr Gln Ala Thr Gly Ala
                325                 330                 335
Lys Tyr Thr Val Lys Ser Gly Asp Ser Val Trp Lys Ile Ala Asn Asp
            340                 345                 350
His Gly Ile Ser Met Asn Gln Leu Ile Glu Trp Asn Asn Ile Lys Asn
            355                 360                 365
Asn Phe Val Tyr Pro Gly Gln Gln Leu Val Val Ser Lys Gly Ser Ser
            370                 375                 380
Ser Ala Ser Gly Ser Thr Ser Asn Thr Ser Thr Gly Asn Thr Ser Ser
385                 390                 395                 400
Asn Thr Ala Asn Thr Gly Ser Thr Thr Ser Gly Ser Thr Tyr Thr Val
                405                 410                 415
Lys Ala Gly Glu Ser Val Trp Ser Val Ser Asn Lys Phe Gly Ile Ser
                420                 425                 430
Met Asn Gln Leu Ile Gln Trp Asn Asn Ile Lys Asn Asn Phe Ile Tyr
            435                 440                 445
Pro Gly Gln Lys Leu Ile Val Lys Gly Gly Ser Ser Ser Ser Asn Ala
            450                 455                 460
Ser Thr Ser Thr Ala Asn Asn Lys Asn Thr Ala Ser Ser Asn Thr Ser
465                 470                 475                 480
Ser Thr Ala Thr Gly Gln Ala Thr Tyr Thr Val Lys Ala Gly Glu Ser
                485                 490                 495
Val Trp Gly Val Ala Asn Lys Asn Gly Ile Ser Met Asn Gln Leu Ile
                500                 505                 510
Glu Trp Asn Asn Ile Lys Asn Asn Phe Ile Tyr Pro Gly Gln Lys Leu
            515                 520                 525
Ile Val Lys Gly Gly Ser Ser Lys Ala Ser Ala Thr Ala Thr Ile Lys
            530                 535                 540
Pro Thr Ala Ser Thr Pro Ala Ser Thr Thr Pro Thr Ala Ser Ser Thr
545                 550                 555                 560
Gly Asp Thr Lys Tyr Thr Val Lys Ala Gly Glu Ser Val Trp Gly Val
                565                 570                 575
Ala Asn Lys His His Ile Thr Met Asp Gln Leu Ile Glu Trp Asn Asn
```

```
                      580                 585                 590
    Ile Lys Asn Asn Phe Ile Tyr Pro Gly Gln Glu Val Ile Val Lys Lys
                595                 600                 605

Gly Thr Ala Gln Ser Thr Pro Ala Lys Ser Asp Glu Lys Thr Tyr Thr
        610                 615                 620

Val Lys Ala Gly Glu Ser Val Trp Gly Val Ala Asp Ser His Gly Ile
    625                 630                 635                 640

Thr Met Asn Gln Leu Ile Glu Trp Asn Asn Ile Lys Asn Asn Phe Ile
                    645                 650                 655

Tyr Pro Gly Gln Gln Leu Ile Val Lys Lys
                660                 665
```

(2) INFORMATION FOR SEQ ID NO: 15:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: DNA (genomic)

Figure 11B:
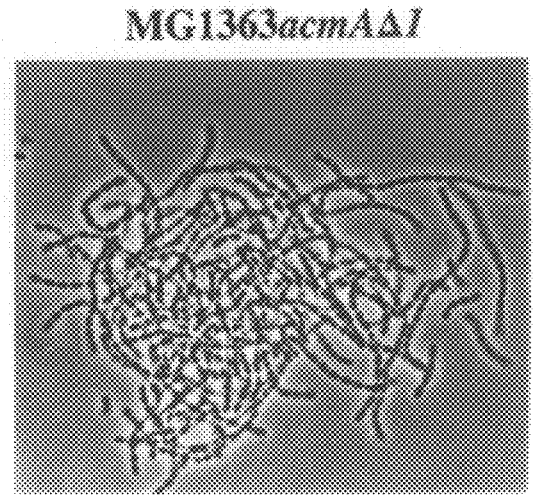

(vi) ORIGINAL SOURCE:
        (A) ORGANISM: Lactococcus lactis phage R1-t (vii) IMMEDIATE SOURCE:
        (B) CLONE: Fig.11b (publ.2) fusionpoint orf29 and lacZ
            gene (ix) FEATURE:
        (A) NAME/KEY: CDS
        (B) LOCATION: 1..93

(xi) SEQUENCE DESCRIPTION: SEQ ID NO: 15:

```
ACA ATC CGA AGC ACG GAG TAC ATG ACG GAT GCG AAG CTT GCA TGC CTG          48
Thr Ile Arg Ser Thr Glu Tyr Met Thr Asp Ala Lys Leu Ala Cys Leu
  1               5                  10                  15

CAG GTC GAC TCT AGA GTC GGG GCC GTC GTT TTA CAA CGT CGT GAC              93
Gln Val Asp Ser Arg Val Gly Ala Val Val Leu Gln Arg Arg Asp
             20                  25                  30
```

(2) INFORMATION FOR SEQ ID NO: 16:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO: 16:

```
Thr Ile Arg Ser Thr Glu Tyr Met Thr Asp Ala Lys Leu Ala Cys Leu
  1               5                  10                  15

Gln Val Asp Ser Arg Val Gly Ala Val Val Leu Gln Arg Arg Asp
             20                  25                  30
```